(12) United States Patent
Markland et al.

(10) Patent No.: US 7,628,983 B2
(45) Date of Patent: Dec. 8, 2009

(54) KALLIKREIN-BINDING "KUNITZ DOMAIN" PROTEINS AND ANALOGUES THEREOF

(75) Inventors: William Markland, Southborough, MA (US); Robert C. Ladner, Ijamsville, MD (US)

(73) Assignee: Dyax Corp., Cambridge, MA (US)

( * ) Notice: Subject to any disclaimer, the term of this patent is extended or adjusted under 35 U.S.C. 154(b) by 156 days.

(21) Appl. No.: 11/365,438

(22) Filed: Mar. 1, 2006

(65) Prior Publication Data
US 2006/0264603 A1 Nov. 23, 2006

Related U.S. Application Data

(60) Continuation of application No. 10/016,329, filed on Oct. 26, 2001, now abandoned, which is a division of application No. 09/421,097, filed on Oct. 19, 1999, now Pat. No. 6,333,402, which is a division of application No. 08/208,264, filed on Mar. 10, 1994, now Pat. No. 6,057,287, which is a continuation-in-part of application No. 08/179,964, filed on Jan. 11, 1994, now abandoned.

(51) Int. Cl.
A61K 38/43 (2006.01)
A61K 38/00 (2006.01)
A01N 37/18 (2006.01)
C12Q 1/00 (2006.01)
C12P 21/04 (2006.01)

(52) U.S. Cl. .................... 424/94.1; 530/300; 514/2; 514/12; 435/4; 435/69.1; 435/71.1

(58) Field of Classification Search .................. None
See application file for complete search history.

(56) References Cited

U.S. PATENT DOCUMENTS

| | | | |
|---|---|---|---|
| 3,682,776 A | 8/1972 | Ekkehard et al. | |
| 3,691,016 A | 9/1972 | Patel | 435/181 |
| 3,969,287 A | 7/1976 | Jaworek et al. | 526/238.1 |
| 4,118,481 A | 10/1978 | Schnabel et al. | |
| 4,153,687 A | 5/1979 | Schnabel et al. | |
| 4,179,337 A | 12/1979 | Davis et al. | 435/181 |
| 4,195,128 A | 3/1980 | Hildebrand et al. | 435/178 |
| 4,229,537 A | 10/1980 | Hodgins et al. | 435/177 |
| 4,247,642 A | 1/1981 | Hirohara et al. | 435/178 |
| 4,330,440 A | 5/1982 | Ayers et al. | 525/54.31 |
| 4,595,674 A | 6/1986 | Tschesche et al. | |
| 4,609,725 A | 9/1986 | Brady et al. | 530/324 |
| 4,657,893 A | 4/1987 | Krantz et al. | |
| 4,845,242 A | 7/1989 | Powers et al. | |
| 5,118,668 A | 6/1992 | Auerswald et al. | |
| 5,223,409 A | 6/1993 | Ladner et al. | 435/67.7 |
| 5,372,933 A * | 12/1994 | Zamarron et al. | 435/7.21 |
| 5,407,915 A | 4/1995 | Fritz et al. | |
| 5,409,895 A | 4/1995 | Morishita et al. | |
| 5,426,224 A | 6/1995 | Lee et al. | |
| 5,441,931 A | 8/1995 | Sprecher et al. | |
| 5,576,294 A | 11/1996 | Norris et al. | |
| 5,677,146 A | 10/1997 | Sprecher et al. | |
| 5,719,041 A | 2/1998 | Lazarus et al. | |
| 5,747,449 A | 5/1998 | Lasters et al. | |
| 5,770,568 A | 6/1998 | Auerswald et al. | |
| 5,780,265 A | 7/1998 | Dennis et al. | |
| 5,786,328 A | 7/1998 | Dennis et al. | |
| 5,795,865 A * | 8/1998 | Markland et al. | 514/12 |
| 5,795,954 A | 8/1998 | Lazarus et al. | |
| 5,800,385 A | 9/1998 | Demopulos et al. | |
| 5,834,244 A | 11/1998 | Dennis et al. | |
| 5,843,895 A | 12/1998 | Lazarus et al. | |
| 5,863,893 A | 1/1999 | Dennis et al. | |
| 5,874,407 A | 2/1999 | Kelley et al. | |
| 5,880,256 A | 3/1999 | Dennis et al. | |
| 5,962,266 A | 10/1999 | White et al. | |
| 5,994,125 A | 11/1999 | Markland et al. | |
| 6,010,880 A | 1/2000 | Markland et al. | |
| 6,013,763 A | 1/2000 | Braisted et al. | |
| 6,057,287 A * | 5/2000 | Markland et al. | 514/2 |
| 6,071,723 A | 6/2000 | Markland et al. | |
| 6,087,473 A | 7/2000 | Conklin et al. | |
| 6,090,916 A | 7/2000 | Vlasuk et al. | |
| 6,103,499 A | 8/2000 | Markland et al. | |
| 6,113,896 A | 9/2000 | Lazarus et al. | |
| 6,159,938 A | 12/2000 | Gyorkos et al. | |
| 6,180,607 B1 | 1/2001 | Davies et al. | |
| 6,261,279 B1 | 7/2001 | Demopulos et al. | |
| 6,306,884 B1 | 10/2001 | Buckman et al. | |
| 6,333,402 B1 | 12/2001 | Markland et al. | |
| 6,423,498 B1 | 7/2002 | Markland et al. | |
| 7,064,107 B2 | 6/2006 | Ladner et al. | |
| 7,067,144 B2 | 6/2006 | Demopulos et al. | |
| 7,153,829 B2 | 12/2006 | Ladner et al. | |
| 7,235,530 B2 | 6/2007 | Blair et al. | |
| 7,276,480 B1 | 10/2007 | Ladner et al. | |
| 2001/0027180 A1 | 10/2001 | Isaacs | |
| 2004/0038893 A1 | 2/2004 | Ladner et al. | |
| 2004/0053206 A1 | 3/2004 | Cicardi et al. | |
| 2004/0171794 A1 | 9/2004 | Ladner et al. | |

(Continued)

FOREIGN PATENT DOCUMENTS

AT    E275583 T1    1/2005

(Continued)

OTHER PUBLICATIONS

Adelman et al., Blood, 68(6):1280-1284 (1986).

(Continued)

*Primary Examiner*—Yong D Pak
(74) *Attorney, Agent, or Firm*—Lando & Anastasi, LLP

(57) ABSTRACT

This invention provides: novel protein homologous of a Kunitz domain, which are capable of binding kallikrein; polynucleotides that encode such novel proteins; and vectors and transformed host cells containing these polynucleotides.

13 Claims, 15 Drawing Sheets

U.S. PATENT DOCUMENTS

| | | | |
|---|---|---|---|
| 2005/0089515 A1 | 4/2005 | Ley et al. |
| 2005/0164928 A1 | 7/2005 | Ladner et al. |
| 2005/0075665 A1 | 8/2005 | Golz et al. |
| 2006/0069020 A1 | 3/2006 | Blair et al. |
| 2007/0049522 A1 | 3/2007 | Ladner et al. |
| 2007/0079096 A1 | 7/2007 | Ladner |
| 2007/0213275 A1 | 9/2007 | Clark et al. |
| 2007/0249807 A1 | 10/2007 | Ladner et al. |
| 2008/0064637 A1 | 3/2008 | Ladner et al. |
| 2008/0076712 A1 | 3/2008 | Ladner et al. |
| 2008/0131426 A1 | 6/2008 | Ladner et al. |
| 2008/0139473 A1 | 6/2008 | Ladner et al. |
| 2008/0152656 A1 | 6/2008 | Ladner et al. |
| 2008/0188409 A1 | 8/2008 | Blair et al. |
| 2008/0200646 A1 | 8/2008 | Ladner et al. |
| 2008/0221031 A1 | 9/2008 | Blair et al. |
| 2008/0226655 A1 | 9/2008 | Ladner et al. |
| 2008/0260752 A1 | 10/2008 | Ladner et al. |

FOREIGN PATENT DOCUMENTS

| | | |
|---|---|---|
| CA | 2180950 | 3/2005 |
| DE | 69533472 T2 | 1/2006 |
| EP | 0 132 732 A2 | 2/1985 |
| EP | 0255011 A | 2/1988 |
| EP | 0 285 123 A2 | 10/1988 |
| EP | 0 307 592 A2 | 3/1989 |
| EP | 0 401 508 A2 | 12/1990 |
| EP | 0401508 A | 12/1990 |
| EP | 0 486 001 A1 | 5/1992 |
| EP | 0 621 870 B1 | 5/1997 |
| EP | 0 621 871 B1 | 7/1997 |
| EP | 1484339 | 8/2004 |
| EP | 0739355 | 9/2004 |
| WO | WO 89/10374 | 11/1989 |
| WO | WO 90/02809 | 3/1990 |
| WO | WO9206111 A1 | 4/1992 |
| WO | WO9309233 A2 | 5/1993 |
| WO | WO 93/14120 | 7/1993 |
| WO | WO 93/14121 | 7/1993 |
| WO | WO93/14122 | 7/1993 |
| WO | WO 93/14122 | 7/1993 |
| WO | WO 95/18830 | 7/1995 |
| WO | WO9518830 A2 | 7/1995 |
| WO | WO 95/21601 | 8/1995 |
| WO | WO0179480 A1 | 10/2001 |
| WO | WO03066824 A1 | 8/2003 |
| WO | WO03103475 A2 | 12/2003 |
| WO | WO2004019968 A1 | 3/2004 |

OTHER PUBLICATIONS

Albrecht et al., Hoppe-Seyler's Z Physiol. Chem., 364:1697-1702 (1983).
Albrecht et al., Hoppe-Seyler's Z Physiol. Chem., 364:1703-1708 (1983).
Anba et al., Biochimie, 70(6):727-733 (1988).
Angliker et al., Biochem. J., 241(3):871-875 (1987).
Atherton et al., J. Chem. Soc. Perkin Trans., 1:538-546 (1981).
Auerswald et al., Bio. Chem. Hoppe-Seyler, 369(Suppl):27-35 (1988).
Balduyck et al., Biol. Chem. Hoppe-Seyler, 366:9-14 (1985).
Baneyx & Georgiou, J. Bacteriol., 173(8):2696-2703 (1991).
Baneyx and Georgiou, J. Bacteriol., 172(1):491-494 (1990).
Berndt et al., Biochemistry, 32(17):4564-4570 (1993).
Bhoola et al., Pharmacological Reviews, 44(1):1-80 (1992).
Browne et al., GeneBank, Accession No. M74220 (1991).
Broze et al., Biochemistry, 29(33):7539-7546 (1990).
Budavari, ed., Merck Index, eleventh ed., ISBN 911910-28-X, entries 923,1745,2740,7425 (1989).
Carey and Sundberg, Advanced Organic Chemistry, Third ed., ISBN 0-306-43456-3, pp. 678-686 (1990).
Chung et al., GenBank, Accession #P03952 (1995).
Colman et al., Hemostasis and Thrombosis, Second Edition (Colman et al., eds; ISBN 0-397-50679-1) Chap. 1, pp. 3-17 (1987).
Currie et al., Tetrahedron, 49(17):3489-3500 (1993).
Dennis and Lazarus, J. Biological Chem., 269(35):22129-22136 (1994).
Dennis and Lazarus, J. Biological Chem., 269(35):22137-22144 (1994).
Diaz et al., Tetrahedron, 49(17):3533-3545 (1993).
DiMaio et al., FEBS Lett. 282(1):47-52 (1991).
Eigenbrot et al., Protein Engineering, 3(7):591-598 (1990).
Ellis et al., Ann. NY Acad. Sci., 667:13-31 (1992).
Fidler and Ellis, Cell, 79:185-188 (1994).
Fields and Noble, Int. J. Peptide Protein Res., 35:161-214 (1990).
Fraedrich et al., Thorac. Cardiovasc. Surg., 37(2):89-91 (1989).
Freidinger et al., J. Org. Chem. 47(1):104-109 (1982).
Gardell, Toxicol. Pathol., 21(2):190-198 (1993).
Girard et al., J. Biol. Chem., 266(8):5036-5041 (1991).
Girard et al., Nature, 338:518-20 (1989).
Hoover et al., Biochemistry, 32:10936-10943 (1993).
Hortin and Trimpe, J. Biol. Chem., 266(11):6866-6871 (1991).
Hynes et al., Biochemistry, 29:10018-10022 (1990).
Kemp and Bowen, Tetrahedron Letts., 29(40):5077-5080. (1988).
Kido et al., Biochem. & Biophys. Res. Comm., 167(2):716-721 (1990).
Kido et al., J. Biol. Chem., 263(34):18104-18107 (1988).
Kline et al., Biochem. Biophys. Res. Commun., 177(3):1049-1055 (1991).
Laskowski and Kato, Ann. Rev. Biochem., 49:593-626 (1980).
Leatherbarrow and Salacinski, Biochemistry, 30(44):1071710721 (1991).
Lohmann and Marshall, Refract. Corneal. Surg. 9(4):300-302 (1993).
Lucas et al., J. Biological Chem., 258(7):4249-4256 (1983).
McConnell et al., J. Med. Chem. 33(1):86-93 (1990).
Mann and Lundblad, Hemostasis and Thrombosis, Second Edition (Colman et al., eds; ISBN 0-397-50679-1) Chap 10, pp. 148-161 (1987).
March, Advanced Organic Chemistry, Third Edition (ISBN 0-471-88841-9) pp. 396-398;1057-1060;1099-1100 (1985).
Merrifield, Science, 232:341-347 (1986).
Merrifield, J. Amer. Chem. Soc.,85:2149-2154 (1963).
Miyajima et al., Gene, 37:155-161 (1985).
Nagai et al., Tetrahedron., 49(17):3577-3592 (1993).
Nagai and Sato, Tetrahedron Lett., 26(5):647-650 (1985).
Neuhaus et al., Lancet, 2(8668)924-925 (1989).
Novotny et al, J. Biol. Chem., 264(31):18832-18837 (1989).
Park and Tulinsky, Biochemistry, 25(14):3977-3982 (1986).
Putterman, Acta Chir. Scand., 155(6-7:)367 (1989).
Robbins, Hemostasis and Thrombosis, Second Edition (Colman et al., eds; ISBN 0-397-50679-1), Chap. 21, pp. 340-357 (1987).
Scatchard, Ann. N.Y. Acad. Sci., 51:660-672 (1949).
Schechter and Berger, Biochem. Biophys. Res. Commun. 32(5):898-902 (1968).
Schechter and Berger, Biochem. Biophys. Res. Commun., 27(2):157-162 (1967).
Schmaier et al., Hemostasis and Thrombosis, Second Edition (Colman et al., eds; ISBN 0-397-50679-1), Chap.2, pp. 18-38 (1987).
Schmidt et al., Swiss-Prot, Accession #P11424 (1992).
Schnabel et al., Biol. Chem. Hoppe-Seyler, 367:1167-1176 (1986).
Sheppard and Williams, Int. J. Peptide Protein Res., 20:451-454 (1982).
Sheridan et al., Dis. Colon Rectum, 32(6):505-508 (1989).
Tian et al., Int. J. Peptide Protein Res., 40(2):119-126 (1992).
Van der Logt et al., Biochemistry, 30(6):1571-1577 (1991).
Van Dijl et al., EMBO J., 11(8):2819-2828 (1992).
Varadi and Patthy, Biochemistry, 23(9):2108-2112 (1984).
Varadi and Patthy, Biochemistry, 22(10):2440-2446 (1983).
Wade et al., Biopolymers, 25:S21-37 (1986).
Wilson et al., Tetrahedron, 49(17):3655-3663 (1993).
Wun et al., J. Biol. Chem. 263(13):6001-6004 (1988).

Brus, E., et al., "Disease Severity is Correlated With Plasma Clotting and Fibrinolytic and Kinin-Kallikrein Activity in Neonatal Respiratory Distress Syndrome," *Pediatr. Res.*, 41(1):120-127 (1997).

Cumming, A.D., and Nimmo, G.R., "Hemodynamic, Renal, and Hormonal Actions of Aprotinin in an Ovine Model of Septic Shock," *Crit. Care Med.*, 20(8):1134-1139 (1992).

DeLa Cadena, R.A., et al., "Inhibition of Plasma Kallikrein Prevents Peptidoglycan-Induced Arthirtis in the Lewis Rat," *FASEB J.*, 9:446-452 (1995).

DeLa Cadena, R.A., et al., "Role of Kallikrein-Kinin System in the Pathogenesis of Bacterial Cell Wall-Induced Inflammation and Enterocolitis," *Transact. Assoc. Am. Physicians*, 105:229-237 (1992).

Dennis, M.S., et al., "Potent and Selective Kunitz Domain Inhibitors of Plasma Kallikrein Designed by Phage Display," *J. Biol. Chem* 270(43):25411-25417 (1995).

Hostomsky', Z., et al., "Solid-Phase Assembly of Cow Colostrum Trypsin Inhibitor Gene," *Nucleic Acids Res.*, 15(12):4849-4856 (1987).

Kirchhoff, C., et al., "A Major Human Epididymis-Specific cDNA Encodes a Protein With Sequence Homology to Extracellular Proteinase Inhibitors," *Biol. Reprod.*, 45:350-357 (1991).

Kurjan, J., and Herskowitz, I., Structure of a Yeast Pheromone Gene (MFα): A Putative α-Factor Precursor Contains Four Tandem Copies of Mature α-Factor, *Cell*, 30:933-943 (1982).

MacGilchrist, A., et al., "Effects of the Serine Protease Inhibitor, Aprotinin, on Systemic Haemodynamics and Renal Function in Patients with Hepatic Cirrhosis and Ascites," *Clin. Sci.*, 87:329-335 (1994).

Monteseiŕin, J., et al., "Plasma Kallikrein Amidolytic Activity in Bronchial Asthma," *Allergol. Immunopathol. (Madr)*, 20(5):211-214 (1992).

Naess, F., et al., "Effects of a Combined Drug Regimen on Tumour Necrosis Factor and Plasma Kallikrein Activity in Experimental Endotoxaemia," *Eur. J. Surg.*, 160:77-86 (1994).

Okamoto, S., et al., "A Finding of Highly Selective Synthetic Inhibitor of Plasma Kallikrein; Its Action to Bradykinin Generation, Intrinsic Coagulation and Experimental DIC," *Agents Actions Suppl.*, 38(I):198-205 (1992).

O'Reilly, M.S., et al., "Angiostatin: A Novel Angiogenesis Inhibitor That Mediates the Suppression of Metastases by a Lewis Lung Carcinoma," *Cell*, 79:317-328 (1994).

Sprecher, C.A., et al., "Molecular Cloning, Expression, and Partial Characterization of a Second Human Tissue-Factor-Pathway Inhibitor," *Proc. Natl., Acad. Sci. USA*, 91:3353-3357 (1994).

Stadnicki, A., et al., "Activation of the Kallikrein-Kinin System in Indomethacin-Induced Enterocolitis in Genetically Susceptible Rats," *J. Invest. Med.*, 44(3):229A (1996).

Vedvick, T., et al, "High-Level Secretion of Biologically Active Aprotinin From the Yeast *Pichia pastoris*," *J. Ind. Microbiol.*, 7(3):197-201 (1991).

Wagner, S.L., et al., "High Level Expression, Purification, and Characterization of the Kunitz-Type Protease Inhibitor Domain of Protease Nexin-2/Amyloid β-Protein Precursor," *Biochem. Biophys. Res. Comm.*, 186(2):1138-1145 (1992).

Sartor, R.B., et al., "Selective Kallikrein-Kinin System Activation in Inbred Rats Differentially Susceptible to Granulomatous Enterocolitis," *Gastroenterology* 110(5):1467-1481 (1996).

Stadnicki, A., et al., "Selective Plasma Kallikrein Inhibitor Attenuates Acute Intestinal Inflammation in Lewis Rat," *Dig. Dis. Sci.*, 41(5):912-920 (1996).

Colman, R.W., et al., "Activation of the Kallikrein-Kinen System in Arthritis and Enterocolitis in Genetically Susceptible Rats: Modulation by a Selective Plasma Kallikrein Inhibitor," *Proc. Assoc. Am. Physicians*, 109(1):10-22 (1997).

Ley, A.C., et al., "Obtaining a Family of High-Affinity, High-Specificity Protein Inhibitors of Plasmin and Plasma Kallikrein," *Molecular Diversity* 2:119-124 (1996).

Markland, W., et al., "Selection for Protease Inhibitors Using Bacteriophage Display,"*Methods Enzymol.*, 267, Combinatorial Chemistry, ed. J.N. Abelson, Academic Press, pp. 28-51 (1996).

Markland, W., et al., "Iterative Optimization of High-Affinity Protease Inhibitors Using Phage Display. 1. Plasmin," *Biochemistry* 35(24):8045-8057 (1996).

Markland, W., et al., "Iterative Optimization of High-Affinity Protease Inhibitors Using Phage Display. 2. Plasma Kallikrein and Thrombin," *Biochemistry* 35(24):8058-8067 (1996).

Baba, M, et al., "States of Tyrosyl Residues and Circular Dichroism of Kunitz Trypsin Inhibitor," *J. Biochem. (Tokyo)*, 65(1):113-121 (1969).

Chen, C., et al., "Solution Structure of a Kunitz-type Chymotrypsin Inhibitor Isolated from the Elapid Snake *Bungarus fasciatus*," *J. Biol. Chem.*, 276:45079-45087 (2001).

Mathews, C. K., et al., *Biochemistry*, The Benjamin/Cummings Publishing Co., Inc., Redwood City, CA., pp. 208-212 (1990).

Beckmann, J., et al., "Preparation of Chemically 'Mutated' Aprotinin Homologues by Semisynthesis: $P_1$ Substitutions Change Inhibitory Specificity," *Eur. J. Biochem.*, 176: 675-682 (1988).

Brinkmann, T., and Tschesche, H., "Design of an Aprotinin Variant With Inhibitory Activity Against Chymotrypsin and Cathepsin G by Recombinant DNA Technology," *Biol. Chem. Hoppe-Seyler*, 371: 43-52 (1990).

Dufton, M.J., "Proteinase Inhibitors and Dendrotoxins," *Eur. J. Biochem.*, 153:647-654 (1985).

Goldenberg, D.P., and Creighton, T.E., "Circular and Circularly Permuted Forms of Bovine Pancreatic Trypsin Inhibitor," *J. Mol. Biol.*, 165: 407-13 (1983).

Tschesche, H., et al., "Semisynthetic Engineering of Proteinase Inhibitor Homologues," *Biochim. Biophys. Acta*, 913:97-101 (1987).

Markland, B.L., et al., "Selection for Protease Inhibitors Using the Bacteriophage-Display Technology," Keystone Symposium on Structural and Molecular Biology of Protease Function and Inhibition, Santa Fe, New Mexico, USA, Mar. 5-12, 1994, *J. Cell. Biochem. Supp. O* 18D: 157, Abstract S 331 (1994).

Roberts, B.L., et al., "Protease Inhibitor Display M13 Phage: Selection of High-affinity Neutrophil Elastase Inhibitors," *Gene*, 121:9-15 (1992).

Roberts, B.L., et al., "Directed Evolution of a Protein: Selection of Potent Neutrophil Elastase Inhibitor Displayed on M13 Fusion Phage," *Proc. Natl. Acad. Sci USA.*, 89:2429-2433 (1992).

Schwarz, H., et al., "Stability Studies on Derivatives of the Bovine Pancreatic Trypsin Inhibitor," *Biochemistry.*, 26:3544-51(1987).

Communication received in EP Application No. 04019920.0, dated Sep. 29, 2005.

PCT International Preliminary Report on Patentability dated Jul. 21, 2008 and issued in PCT/US05/34335.

PCT Written Opinion dated Jul. 21, 2008 and issued in PCT/US05/34335.

Attwood, The Babel of Bioinformatics; Science, vol. 290, pp. 471-473 (2000).

Skolnick and Fetrow, From Genes to Protein Structure and Function: Novel Applications of Computational Approaches in the Genomic Era; Trends in Biotechnology, vol. 18, pp. 34-39 (2000).

Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).

The Merck Index: pp. 145, 263,427, 428, 1183, and 1184, (1989).

Lumry et al, Interim Results of EDEMA2, A Multicenter, Open-Label, Repeat-Dosing Study of Intravenous and Subcutaneous Administration of Ecallantide (DX-88) in Hereditory Angioedema. J. Allergy and Clinical Immunology 117(2)(Suppl. 1):S179 Abstract 699 (2006).

International Search Report received in PCT/US07/63703, dated Dec. 21, 2007.

Han, Eun D. Reversal of the Increased Vascular Permeability in C1 Inhibitor Deficient Mice: Therapeutic Approaches, International Immunopharmacology 2(9):1315 Abstract 176 (2002).

Han, Eun D. et al., Increased Vascular Permeability in C1 Inhibitor-Deficient Mice Mediated by the Bradykinin Type 2 Receptor, J. Clinical Investigation 109(8):1057-1063 (2002).

Gonzalez-Quevedo, T. et al., The Synthetic Kunitz Domain Protein DX88 to Treat Angioedema in Patients with Hereditary Angioedema, International Immunopharmacology 2(9):1318 Abstract 205 (2002).

Rossi, E. et al., The Synthetic Peptide DX88 Binds to Endothelial Cells In Vitro and Retains the Inhibitory Activity on Kallikrein, International Immunopharmacology 2(9):1313, Abstract 142 (2002).

Communication received in EP Patent Application 03757339.1, dated Apr. 23, 2008.

Pan et al. Neuroradiology 2007, 49:93-102.

Siebeck et al. J. Trauma, 1993 34:193-198.

Communication received in EP Patent Application 03791557.6, dated Nov. 27, 2008.

McCarty, "Crystal-Induced Inflamation of the joints", Annual Reviews of Medicine, vol. 21 pp. 357-366, (1970).

International Search Report including Written Opinion received in PCT/US08/74061, dated Dec. 28, 2008.

International Search Report including Written Opinion received in PCT/US08/73665, dated Feb. 5, 2008.

Pitt et al., Rabbitt monoarticular arthritis as a model for intra-articular drug injections. The local action of administered cortisol and alpha-1 proteinase inhibitor. Agents and Actions, Dec. 1984, vol. 15, No. 5-6, abstract online, retrieved from internet <URL:http://www.springerlink.com/content/j82860503948741p/>.

Extended European Search Report dated Apr. 1, 2009, which includes the European Search Report and the European Search Opinion.

* cited by examiner

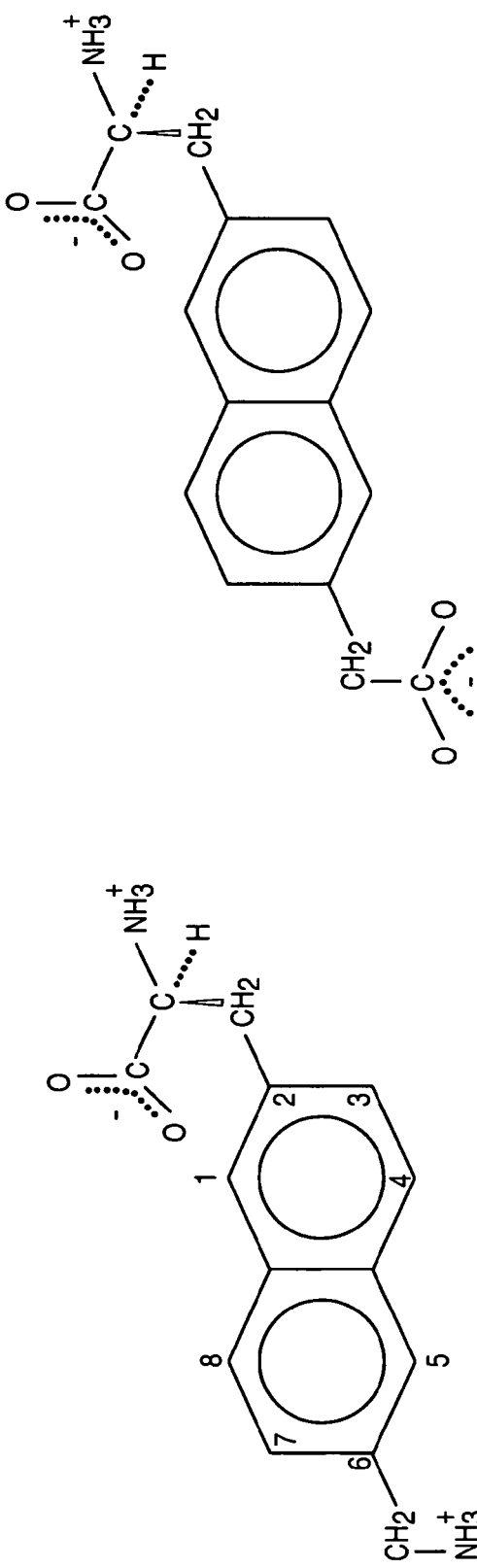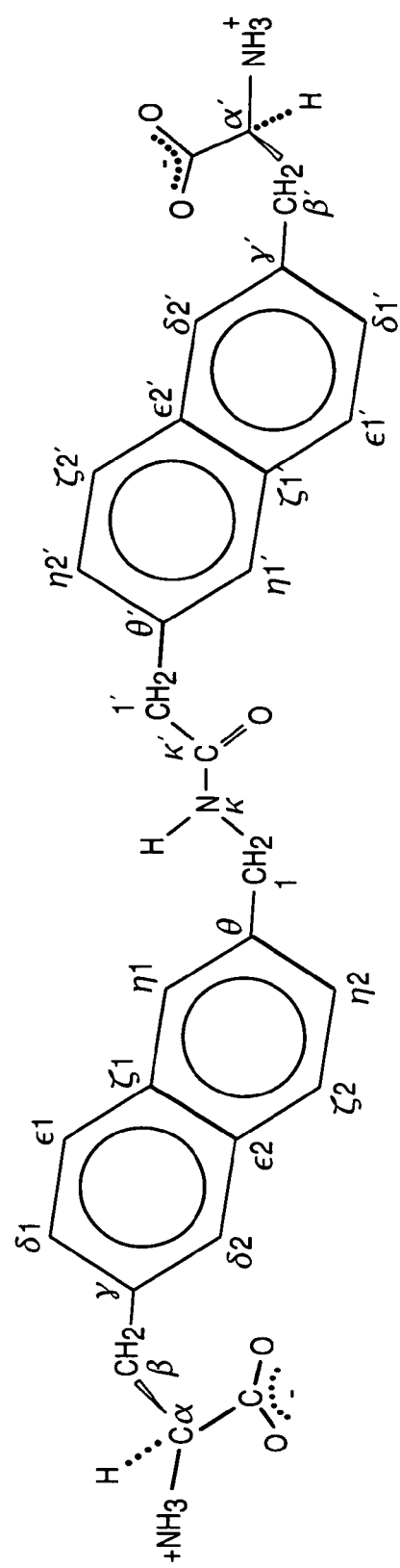
FIG. 3A
FIG. 3B
FIG. 3C

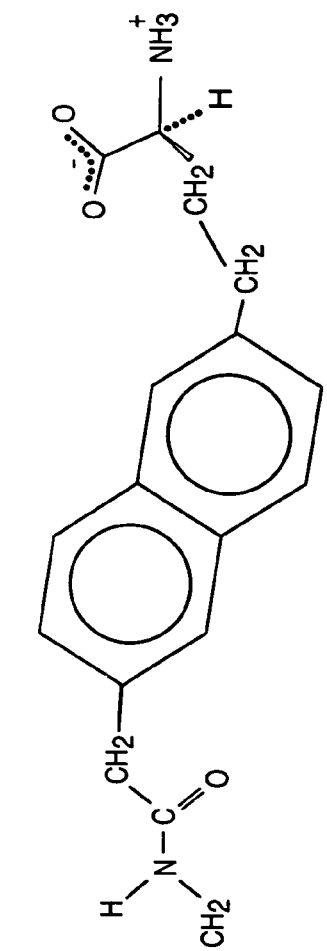
FIG. 3E
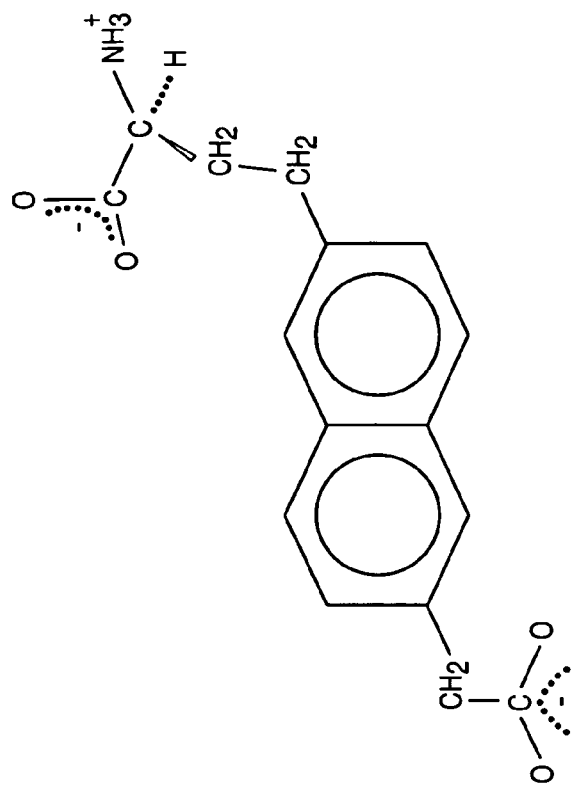
FIG. 3D
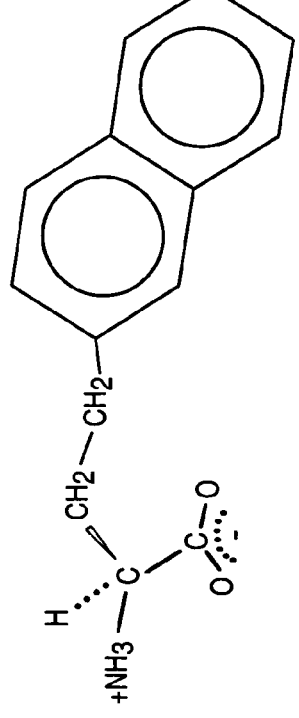
FIG. 3F
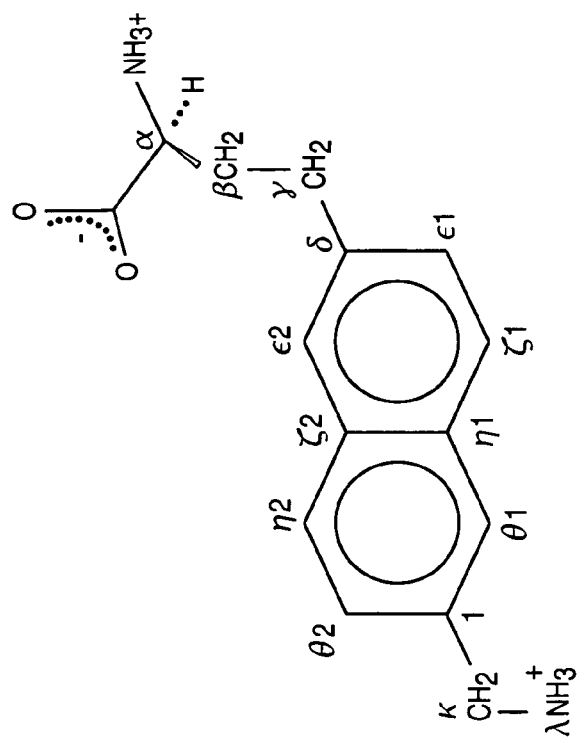

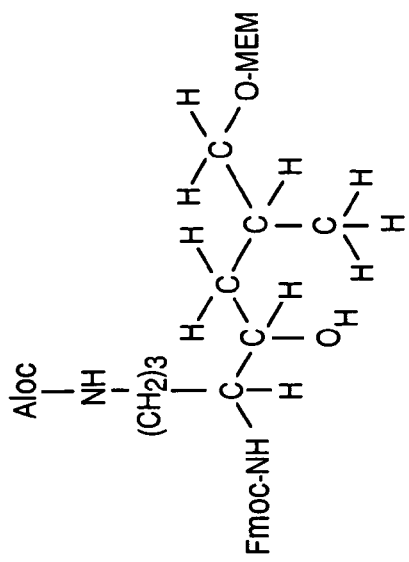
FIG. 5A
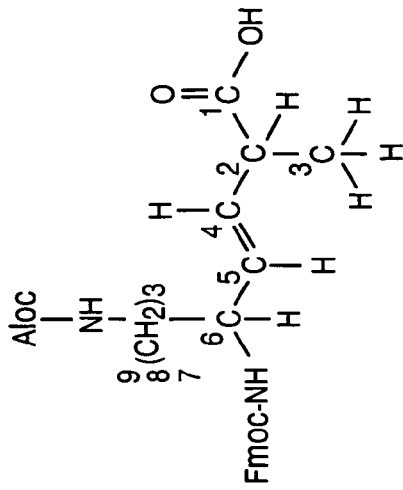
FIG. 5B
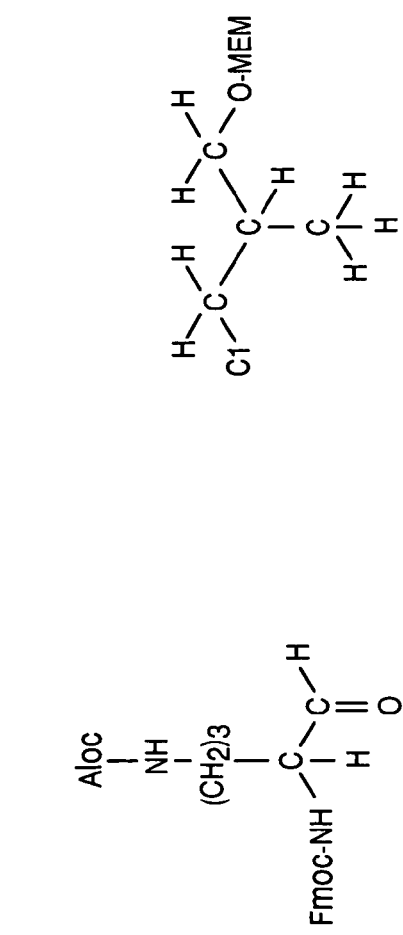
FIG. 5C
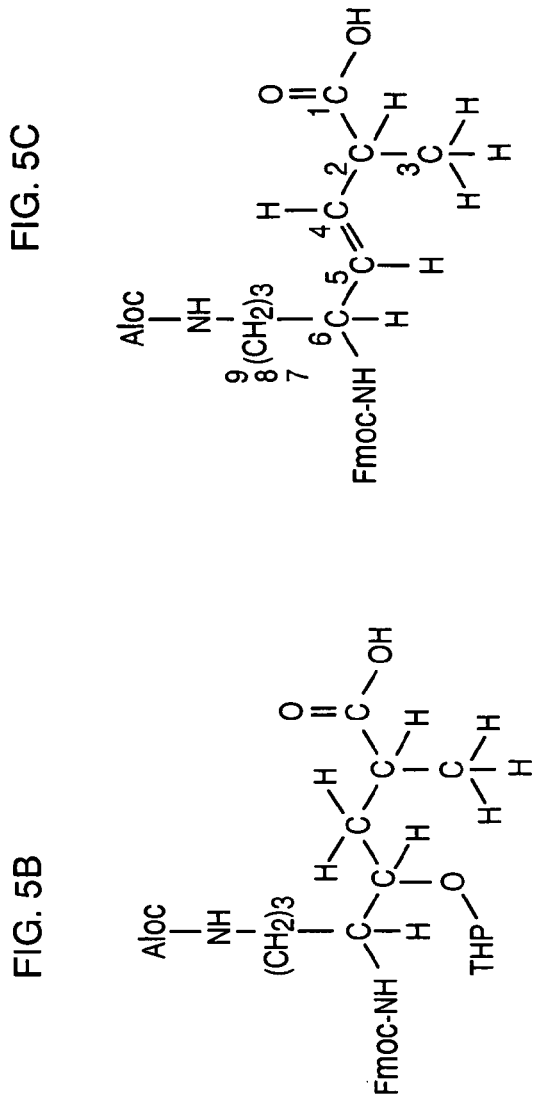
FIG. 5D
FIG. 5E
FIG. 5F

KALLIKREIN-BINDING "KUNITZ DOMAIN" PROTEINS AND ANALOGUES THEREOF

RELATED APPLICATIONS

This application is a continuation of U.S. Ser. No. 10/016,329, filed Oct. 26, 2001 now abandoned, which is a division of U.S. application Ser. No. 09/421,097, filed Oct. 19, 1999, now U.S. Pat. No. 6,333,402; which is a division of U.S. application Ser. No. 08/208,264, filed Mar. 10, 1994, now U.S. Pat. No. 6,057,287; which is a continuation-in-part of U.S. application Ser. No. 08/179,964, filed Jan. 11, 1994, now abandoned, the entirety of which are hereby incorporated by reference.

BACKGROUND OF THE INVENTION

1. Field of the Invention

The present invention relates to novel classes of proteins and protein analogues which bind to and may inhibit kallikrein.

2. Description of the Background Art

Kallikreins are serine proteases found in both tissues and plasma. Plasma kallikrein is involved in contact-activated (intrinsic pathway) coagulation, fibrinolysis, hypotension, and inflammation. (See Bhoola, et al. (BHOO92)). These effects of kallikrein are mediated through the activities of three distinct physiological substrates:

i) Factor XII (coagulation),
ii) Pro-urokinase/plasminogen (fibrinolysis), and
iii) Kininogens (hypotension and inflammation).

Kallikrein cleavage of kininogens results in the production of kinins, small highly potent bioactive peptides. The kinins act through cell surface receptors, designated BK-1 and BK-2, present on a variety of cell types including endothelia, epithelia, smooth muscle, neural, glandular and hematopoietic. Intracellular heterotrimeric G-proteins link the kinin receptors to second messenger pathways including nitric oxide, adenyl cyclase, phospholipase $A_2$ and phospholipase C. Among the significant physiological activities of kinins are: (i) increased vascular permeability; (ii) vasodilation; (iii) bronchospasm; and (iv) pain induction. Thus, kinins mediate the life-threatening vascular shock and edema associated with bacteremia (sepsis) or trauma, the edema and airway hyperreactivity of asthma, and both inflammatory and neurogenic pain associated with tissue injury. The consequences of inappropriate plasma kallikrein activity and resultant kinin production are dramatically illustrated in patients with hereditary angioedema (HA). HA is due to a genetic deficiency of C1-inhibitor, the principal endogenous inhibitor of plasma kallikrein. Symptoms of HA include edema of the skin, subcutaneous tissues and gastrointestinal tract, and abdominal pain and vomiting. Nearly one-third of HA patients die by suffocation due to edema of the larynx and upper respiratory tract. Kallikrein is secreted as a zymogen (prekallikrein) that circulates as an inactive molecule until activated by a proteolytic event. Genebank entry P03952 shows Human Plasma Prekallikrein.

Mature plasma Kallikrein contains 619 amino acids. Hydrolysis of a single Arg-Ile bond (at positions 371-372) results in the formation of a two-chain proteinase molecule held together by a disulfide bond. The heavy chain (371 amino acids) comprises four domains arranged in sequential tandems of 90-91 residues. Each of the four domains is bridged by 6 half-cysteine residues, except the last one, which carries two additional half-cysteine residues to link together the heavy and light chains. These domains are similar in sequence to factor XI. The light chain (248 residues) carries the catalytic site, and the catalytic triad of His-415, Asp-464 and Ser-559 is especially noteworthy.

The most important inhibitor of plasma kallikrein (pKA) in vivo is the C1 inhibitor; see SCHM87, pp. 27-28. C1 is a serpin and forms an irreversible or nearly irreversible complex with pKA. Although bovine pancreatic trypsin inhibitor (BPTI) (SEQ ID NO:1) was first said to be a strong pKA inhibitor with $K_i$=320 pM (AUER88), a more recent report (Berndt, et al., *Biochemistry,* 32:4564-70, 1993) indicates that its Ki for plasma Kallikrein is 30 nM (i.e., 30,000 pM). The G36S mutant had a Ki of over 500 nM.

"Protein engineering" is the art of manipulating the sequence of a protein in order to alter its binding characteristics. The factors affecting protein binding are known, but designing new complementary surfaces has proved difficult. Although some rules have been developed for substituting side groups, the side groups of proteins are floppy and it is difficult to predict what conformation a new side group will take. Further, the forces that bind proteins to other molecules are all relatively weak and it is difficult to predict the effects of these forces.

Nonetheless, there have been some isolated successes. Wilkinson et al. reported that a mutant of the tyrosyl tRNA synthetase of *Bacillus stearothermophilus* with the mutation $Thr_{51}\rightarrow Pro$ exhibits a 100-fold increase in affinity for ATP. Tan and Kaiser and Tschesche et al. showed that changing a single amino acid in a protein greatly reduces its binding to trypsin, but that some of the mutants retained the parental characteristic of binding to an inhibiting chymotrypsin, while others exhibited new binding to elastase.

Early techniques of mutating proteins involved manipulations at the amino acid sequence level. In the semisynthetic method, the protein was cleaved into two fragments, a residue removed from the new end of one fragment, the substitute residue added on in its place, and the modified fragment joined with the other, original fragment. Alternatively, the mutant protein could be synthesized in its entirety.

With the development of recombinant DNA techniques, it became possible to obtain a mutant protein by mutating the gene encoding the native protein and then expressing the mutated gene. Several mutagenesis strategies are known. One, "protein surgery", involves the introduction of one or more predetermined mutations within the gene of choice. A single polypeptide of completely predetermined sequence is expressed, and its binding characteristics are evaluated.

At the other extreme is random mutagenesis by means of relatively nonspecific mutagens such as radiation and various chemical agents, see Lehtovaara, E. P. Appln. 285,123, or by expression of highly degenerate DNA. It is also possible to follow an intermediate strategy in which some residues are kept constant, others are randomly mutated, and still others are mutated in a predetermined manner. This is called "variegation". See Ladner, et al. U.S. Pat. No. 5,220,409.

The use of site-specific mutagenesis, whether nonrandom or random, to obtain mutant binding proteins of improved activity, is known in the art, but does not guarantee that the mutant proteins will have the desired target specificity or affinity. Given the poor anti-kallikrein activity of BPTI, mutation of BPTI or other Kunitz domain proteins would not have been considered, prior to the present invention, a preferred method of obtaining a strong binder, let alone inhibitor, of kallikrein.

SUMMARY OF THE INVENTION

The present invention relates to novel Kunitz domain proteins, especially LACI homologues, which bind to, and preferably inhibit, one or more plasma (and/or tissue) kallikreins, and to the therapeutic and diagnostic use of these novel proteins.

A specific, high affinity inhibitor of plasma kallikrein (and, where needed, tissue kallikrein) will demonstrate significant therapeutic utility in all pathological conditions mediated by kallikrein, and especially those associated with kinins. The therapeutic approach of inhibiting the catalytic production of kinins is considered preferable to antagonism of kinin receptors, since in the absence of kallikrein inhibition, receptor antagonists must compete with continuous kinin generation. Significantly, genetic deficiency of plasma kallikrein is benign and thus, inhibition of plasma kallikrein is likely to be safe. We have recently discovered a lead pKA inhibitor, designated KKII/3#6 (SEQ ID NO:7). This inhibitor is a variant of a naturally occurring human plasma protein Kunitz domain and demonstrates significantly greater kallikrein binding potency than Trasylol. KKII/3#6 (SEQ ID NO:7) has a Ki for kallikrein which is over 100 times that of both wild-type LACI (SEQ ID NO:25) and of BPTI (SEQ ID NO:1), and is in the nanomolar range. In contrast, its Ki for plasmin is 10 uM. A reversible inhibitor is believed to be of greater utility than an irreversible inhibitor such as the C1 inhibitor.

The present invention also relates to protein and non-protein analogues, designed to provide a surface mimicking the kallikrein-binding site of the proteins of the present invention, which likewise bind kallikrein. These are termed "conformational analogues."

Figure 1A:
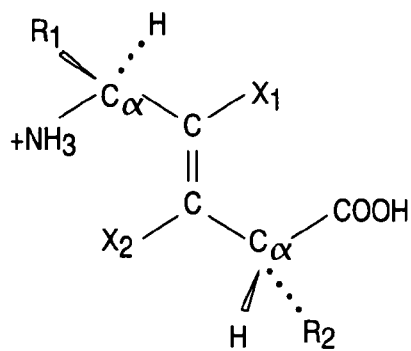
FIG. 1 shows six pseudopeptide bonds, in each figure, $R_1$ and $R_2$ are the side groups of the two amino acids that form the pseudodipeptide. If, for example, the dipeptide to be mimiced is ARG-PHE, then $R_1 = -(CH_2)_3-NH-C-(NH_2)_2+$ and $R_2 = -CH_2-C_6H_5$. The pseudopeptides are not limited to side groups found in the twenty genetically encoded amino acids.
Figure 1B:
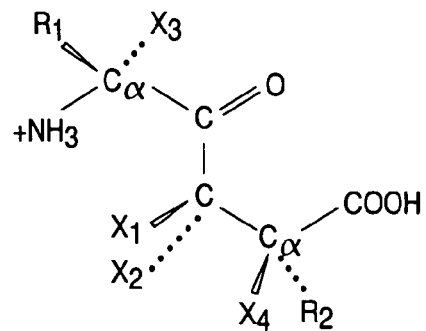
Figure 1C:
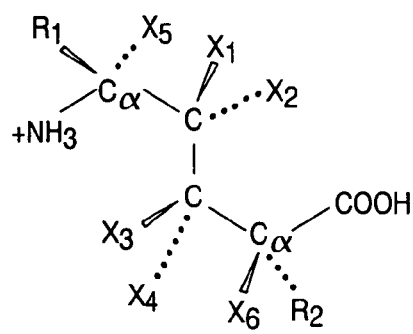
Figure 1D:
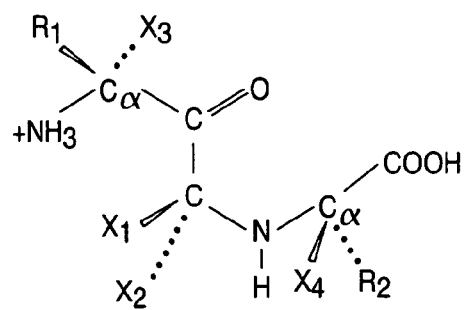
Figure 1E:
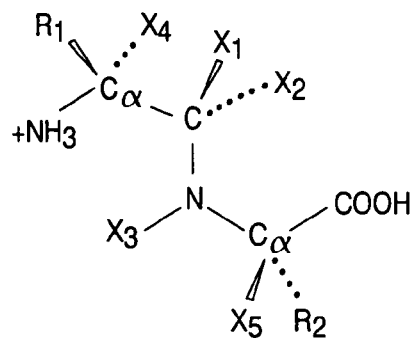
Figure 1F:
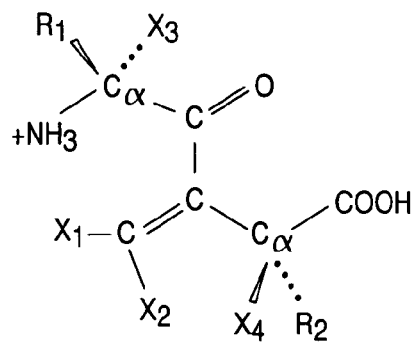
Figure 2A:
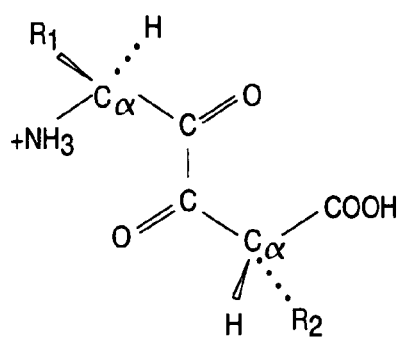
Figure 2B:
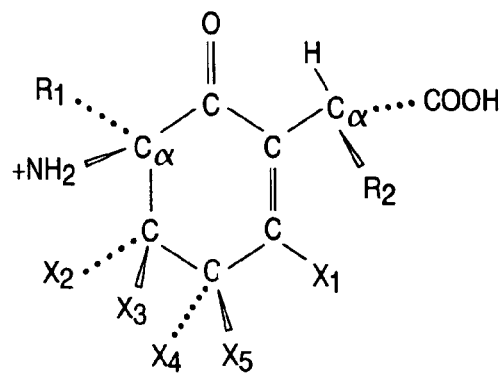
Figure 2C:
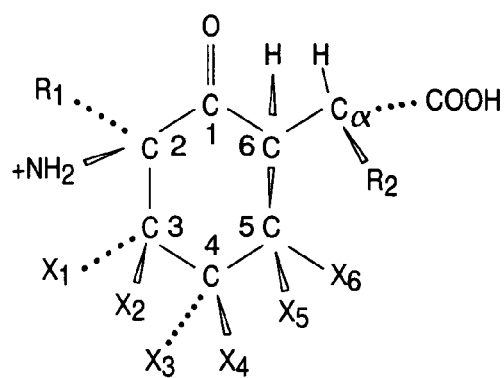
Figure 2D:
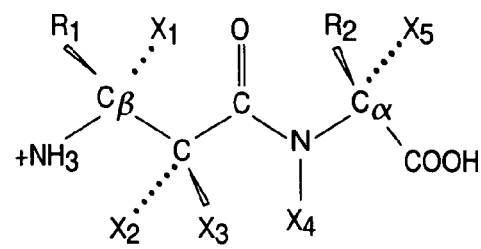
Figure 2E:
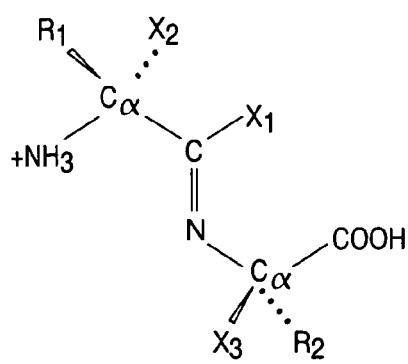
Figure 2F:
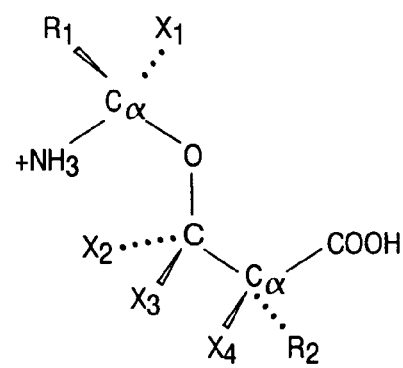
Figure 4A:
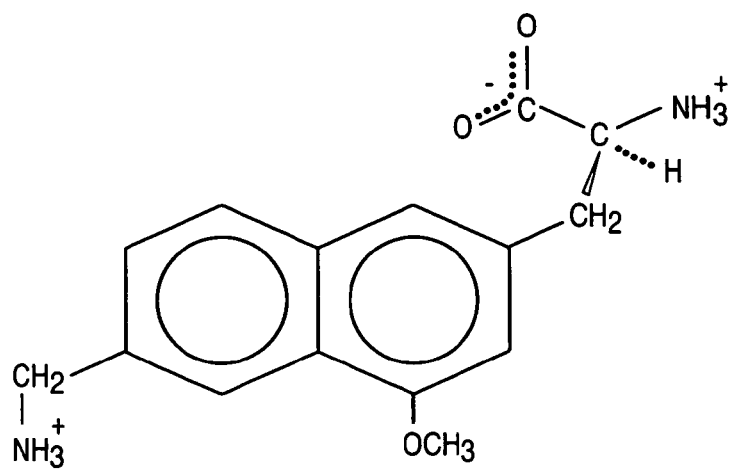
Figure 4B:
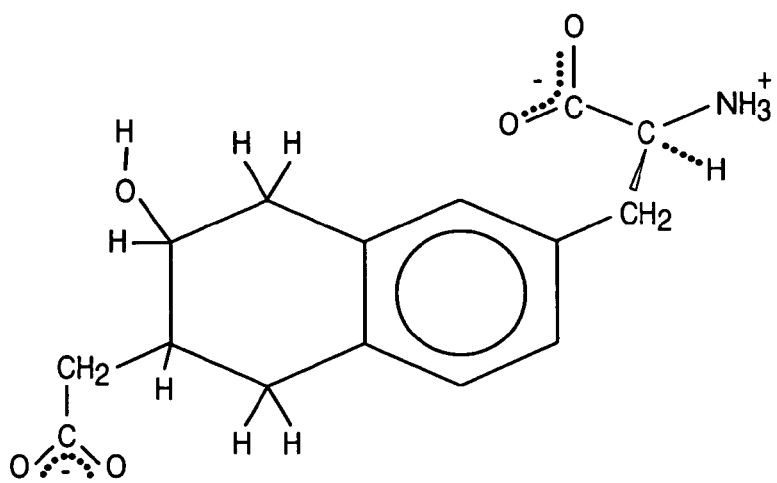
Figure 4C:
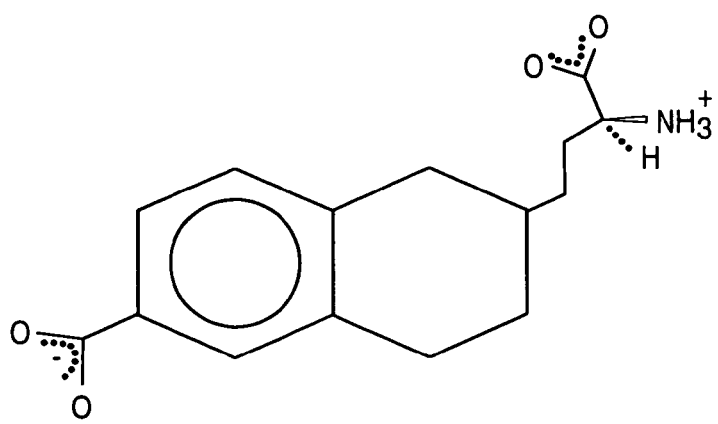
Figure 4D:
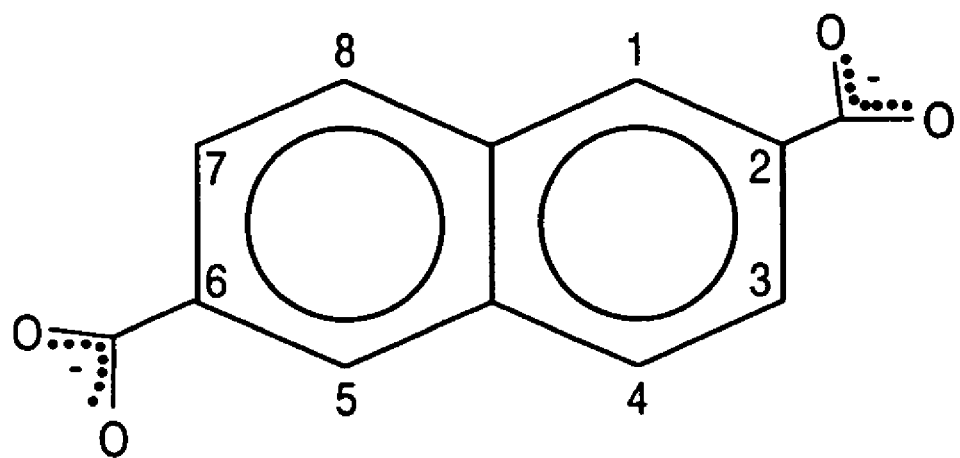
Figure 4E:
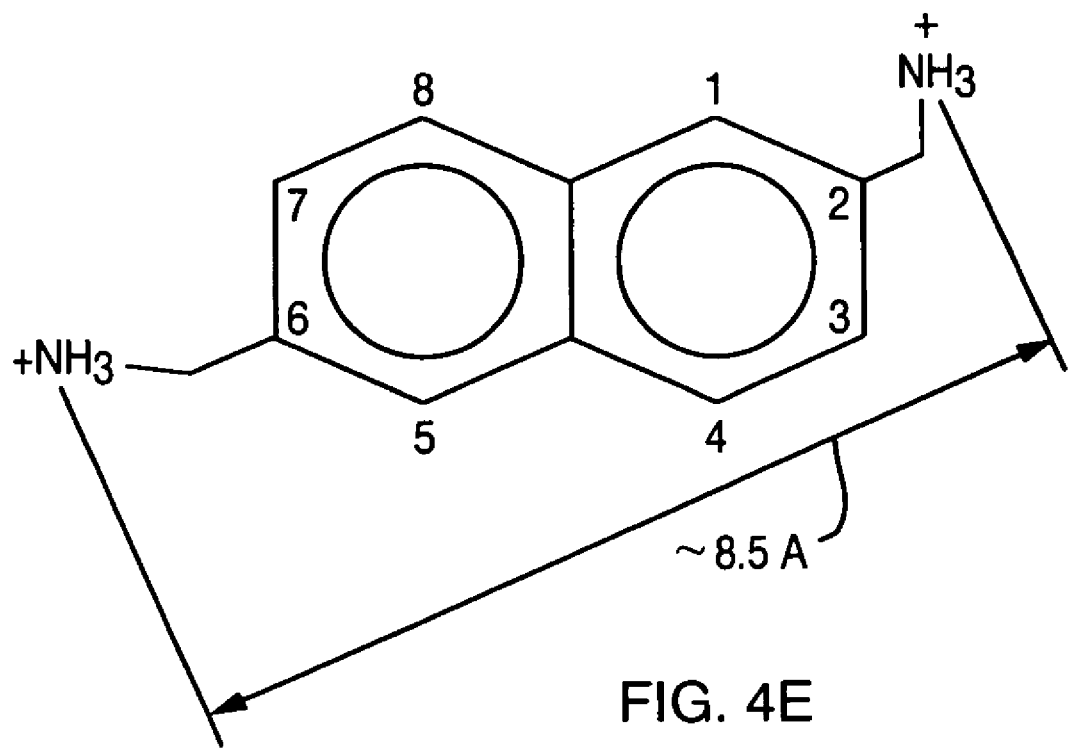

a) $\psi 1(X_1,X_2,R_1,R_2)$ shows two α carbons joined by a trans ethylene moiety,
- $X_1$ and $X_2$ may independently be any group consistent with the stability of the vinyl group; for example, $X_1$ and $X_2$ may be picked from the set comprising
  {H, -alkyl (methyl, ethyl, etc.), —O-alkyl (especially methyl), —O— fluoroalkyl (—O—$CF_3$, —O—$CF_2$—$CF_3$), halo (F, Cl, and Br), -fluoroalkyl (e.g. —$CF_3$, —$CF_2$—$CH_3$, —$C_2F_5$), and secondary amine (such as N,N dimethyl)};
- preferred $X_1$ groups are electronegative such as —O-alkyl and F or hydrogen;
- preferred $X_2$ groups are H, alkyl, and secondary amines, b) "$\psi 2(X_1,X_2,X_3,X_4,R_1,R_2)$" shows two α carbons joined by a ketomethylene moiety,
- $X_1$ and $X_2$ may independently be any group consistent with the stability of the ketomethylene group; for example, $X_1$ and $X_2$ may be picked from the set comprising one of
  {H, alkyl, amino, alkyl amino, —OH, —O-alkyl, —NH—COH, and F};
- preferred $X_1$ and $X_2$ groups are H, methyl, —$NH_2$, —OH, and F (α fluoroketones are not nearly so reactive as are chloro and bromo ketones);
- $X_3$ and $X_4$ may independently by any one of
  {H and alkyl (especially methyl)};
- H is preferred, but alkyl groups may be used to limit the flexibility of the peptide chain, c) "$\psi 3(X_1,X_2,X_3,X_4,X_5,X_6,R_1,R_2)$" shows two α carbons joined by two methylene groups,
- $X_1$, $X_2$, $X_3$, and $X_4$ may independently be any group consistent with the stability of the bismethylene group; for example, $X_1$, $X_2$, $X_3$, and $X_4$ may be picked from the set comprising
  {H, —O-alkyl (especially methyl), F, Cl, Br, -alkyl (methyl, ethyl, etc.), hydroxy, amino, alkyl hydroxy (e.g. —$CH_2$—OH, —$CH(CH_3)OH$), alkyl amino, and secondary amino (such as N,N dimethyl)};
- $X_5$ and $X_6$ may be independently picked from the set comprising
  {H, alkyl, arylalkyl (e.g. —$CH_2$—$C_6H_5$), alkyl hydroxy, alkyl amino, aryl, alkylaryl (e.g. p-$C_6H_4$—$CH_2$—$CH_3$)}.

d) "$\psi 4(X_1,X_2,X_3,X_4,R_1,R_2)$" shows two α carbons joined by —CO—C($X_1$)($X_2$)—NH—,
- $X_1$ and $X_2$, may independently be any group consistent with the stability of the aminomethylketo group; for example, $X_1$ and $X_2$ may be picked from the set comprising
  {H, alkyl, amino, alkyl amino, —OH (but not two hydroxyls), —O-alkyl, and F},
- alternatively, $X_1$ and $X_2$ can be combined as the oxygen atom of an α keto carboxylic acid group (that is, the first residue is a β amino keto acid);
- $X_3$ and $X_4$ may be independently picked from the set comprising
  {H, alkyl, alkyl hydroxy, alkyl amino, aryl, alkylaryl (e.g. —$CH_2$—$C_6H_5$)}, hydrogen is preferred, but larger groups may be used to limit the flexibility and reactivity of the peptide main chain.

e) "$\psi 5(X_1,X_2,X_3,X_4,X_5,R_1,R_2)$" shows two α carbons joined by a methylene-amine group;
- $X_1$ and $X_2$ may be any group consistent with stability of the amine group; preferably, $X_1$ and $X_2$ may be picked independently from the set
  {H, alkyl (methyl, ethyl, n-propyl, isopropyl, up to about $C_6$), —OH (but $X_1$ and $X_2$ can not both simultaneously be —OH), —O-alkyl (methyl, ethyl, n-propyl, isopropyl, up to about $C_6$)},
- $X_3$ can be any group consistent with being a stable substituent on a tertiary or secondary amine, perferably $X_3$ is picked from the set
  {H, alkyl ($C_1$ up to about $C_6$), alkylhydroxy (—$CH_2$—OH, —$CH_2$—$CH_2$—OH, up to about —$C_6O_2H_{13}$)};
- $X_4$ and $X_5$ may be independently picked from the set comprising
  {H, alkyl, alkyl hydroxy, alkyl amino, aryl, alkylaryl (e.g. —$CH_2$—$C_6H_5$)}, hydrogen is preferred, but other groups may be used to limit the flexibility and reactivity of the peptide main chain.

f) "$\psi 6(X_1,X_2,X_3,X_4,R_1,R_2)$" shows two α carbons joined by a vinylketone group;
- $X_1$ and $X_2$ may be any group consistent with stability of the compound;
- preferably, $X_1$ and $X_2$ may be picked independently from the set
  {H, alkyl (methyl, ethyl, n-propyl, isopropyl, up to about $C_6$), —O-alkyl (methyl, ethyl, n-propyl, isopropyl, up to about $C_6$), alkylhydroxy (—$CH_2$—OH, —$CH_2$—$CH_2$—OH, up to about —$C_6O_2H_{13}$)}, $X_3$ and $X_4$ may be independently picked from the set comprising {H, alkyl, alkyl hydroxy, alkyl amino, aryl, alkylaryl (e.g. —$CH_2$—$C_6H_5$)}, hydrogen is preferred, but other groups may be used to limit the flexibility and reactivity of the peptide main chain.

FIG. 2 shows six additional pseudopeptide linkages:

a) "ψ7($X_1,X_2,R_1,R_2$)", a bisketone;

$X_1$ and $X_2$ may be independently picked from the set comprising

{H, alkyl, alkyl hydroxy, alkyl amino, aryl, alkylaryl (e.g. —$CH_2$—$C_6H_5$)}, hydrogen is preferred, but other groups may be used to limit the flexibility and reactivity of the peptide main chain.

b) "ψ8($X_1,X_2,X_3,X_4,X_5,R_1,R_2$)", a cyclohexenone derivative:

$X_1$ can be any of

{H, —O-alkyl (especially methyl), F, -alkyl (methyl, ethyl, etc.), and secondary amine (such as N,N dimethyl)};

$X_2$, $X_3$, $X_4$, and $X_5$ may be picked independently from the set

{H, —OH (but not two hydroxyls on the same carbon), alkyl (methyl, ethyl, n-propyl, isopropyl, up to about $C_6$), —O-alkyl, —O-alkylaryl (e.g. —O—$CH_2$—$C_6H_5$), alkylhydroxy (—$CH_2$—OH, —$CH_2$—$CH_2$—OH, etc.), F, Cl, Br, I, aryl, arylalkyl, —S-alkyl} ($X_4$ and $X_5$ should not be Cl, Br, or I).

c) "ψ9($X_1,X_2,X_3,X_4,X_5,X_6,R_1,R_2$)", a cyclohexone derivative:

$X_1$, $X_2$, $X_3$, $X_4$, $X_5$, and $X_6$ can independently be any of

{H, hydroxy (but not two hydroxyl groups on one carbon), —O-alkyl (especially methyl), F, -alkyl (methyl, ethyl, etc.), and secondary amine (such as N,N dimethyl)} d) "ψ10($X_1,X_2,X_3,X_4,X_5,R_1,R_2$)", a β amino acid derivative:

$X_1$ and $X_5$ may be independently picked from the set comprising

{H, alkyl, alkyl hydroxy, alkyl amino, aryl, alkylaryl (e.g. —$CH_2$—$C_6H_5$)}; H is preferred.

$X_2$ and $X_3$ can independently be picked from the set:

{H, methyl, ethyl, n-propyl, isopropyl, n-butyl, isobutyl, s-butyl, t-butyl, other alkyls up to $C_6$, —OH, —O-methyl, —$CH_2$—OH}; alternatively, $X_2$ and $X_3$ can be a single double-bonded group, such as =O, =N-alkyl, or =C($X_6$)($X_7$) (where $X_6$ and $X_7$ may be H or methyl)}, $X_4$ can be {H, alkyl, aryl, or substituted hydrocarbon chains}.

e) "ψ11($X_1, X_2,X_3,R_1,R_2$)", an imine derivative:

$X_1$ can be any group consistent with the imine bond:

{H, methyl, alkyl(up to $C_6$), —O-methyl, —O-ethyl}, $X_2$ and $X_3$ may be independently picked from the set comprising {H, alkyl, alkyl hydroxy, alkyl amino, aryl, alkylaryl (e.g. —$CH_2$—$C_6H$)}.

f) "ψ12($X_1,X_2,X_3,X_4,R_1,R_2$)", an ether derivative:

$X_1$ and $X_4$ may be independently picked from the set comprising

{H, alkyl, alkyl hydroxy, alkyl amino, aryl, alkylaryl (e.g. —$CH_2$—$C_6H_5$)}.

$X_2$ and $X_3$ may be picked independently from the set

{H, —OH (but not two hydroxyls on the same carbon), alkyl (methyl, ethyl, n-propyl, isopropyl, up to about $C_6$), —O-alkyl, —O-alkylaryl (e.g. —O—$CH_2$—$C_6H_5$), alkylhydroxy (—$CH_2$—OH, —$CH_2$—$CH_2$—OH, etc.), F, Cl, Br, I, aryl, arylalkyl, —S-alkyl}.

FIG. 3 shows a number of amino acids that can be used to create cyclic peptides by joining the side groups:

(A) shows L-2-(6-aminomethylnaphthyl)alanine, (B) shows L-2-(6-carboxymethylnaphthyl)alanine, (C) shows shows the crosslink generated by joining L-2-(6-aminomethylnaphthyl)alanine to L-2-(6-carboxymethylnaphthyl)alanine by a peptide bond between the substituents on the θ positions (the 6 position of naphthylene), (D) shows L-4-(2-(6-aminomethylnaphthyl))-2-aminobutyric acid, (E) shows L-4-(2-(6-carboxymethylnaphthyl))-2-aminobutyric acid, and (F) shows the crosslink generated by joining (D) to (E) through the substituents on the 6 position of each naphthene group.

FIG. 4 shows additional compounds that can be used to close a cyclic peptide:

(A) shows L-2-(4-oxymethyl-6-aminomethylnaphthyl) alanine, (B) shows L-2-(6-carboxymethyl-7-hydroxy-5,6,7,8-tetrahydro-naphthyl)alanine, (C) shows L-4-(2-(6-carboxy-1,2,3,4-tetrahydronaphthyl))-2-aminobutyric acid, (D) shows 2,6 biscarboxymethylnaphthylene, (E) shows 2,6 bisaminomethylnaphthylene, the separation between nitrogens is about 8.5 Å.

FIG. 5 shows intermediates leading to an ethylene pseudopeptide and a ornithine=alanine pseudopeptide.

Figure 6A:
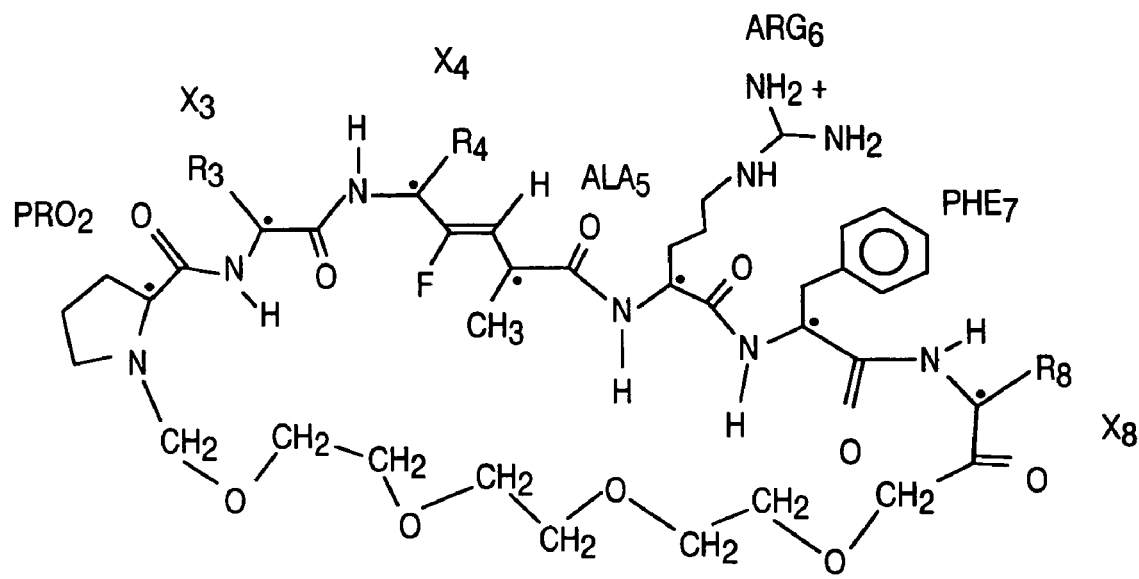
Figure 6B:
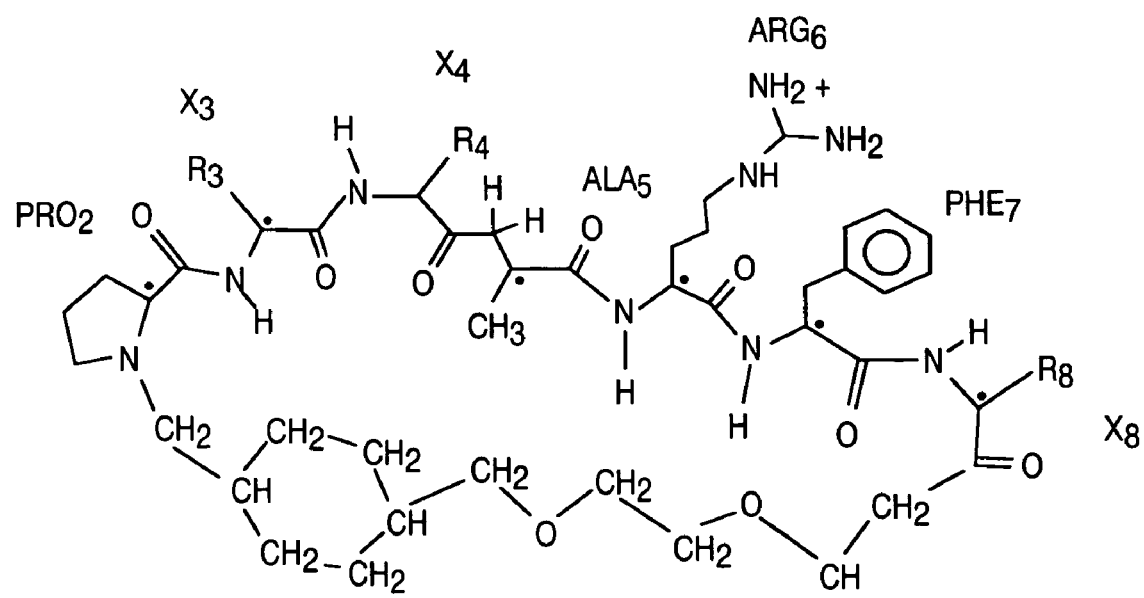

FIG. 6 shows compounds 4.1 and 4.2 according to formula 4. Cmpd 4.1 has a linker comprising —$CH_2$—(O—$CH_2$—$CH_2)_3$—$CH_2$—; the pseudopeptide is a fluoroethylene group. Cmpd 4.2 has a linker derived from trans cyclohexanedimethanol and ethyleneglycol units and a ketomethylene group as pseudopeptide.

Figure 7A:
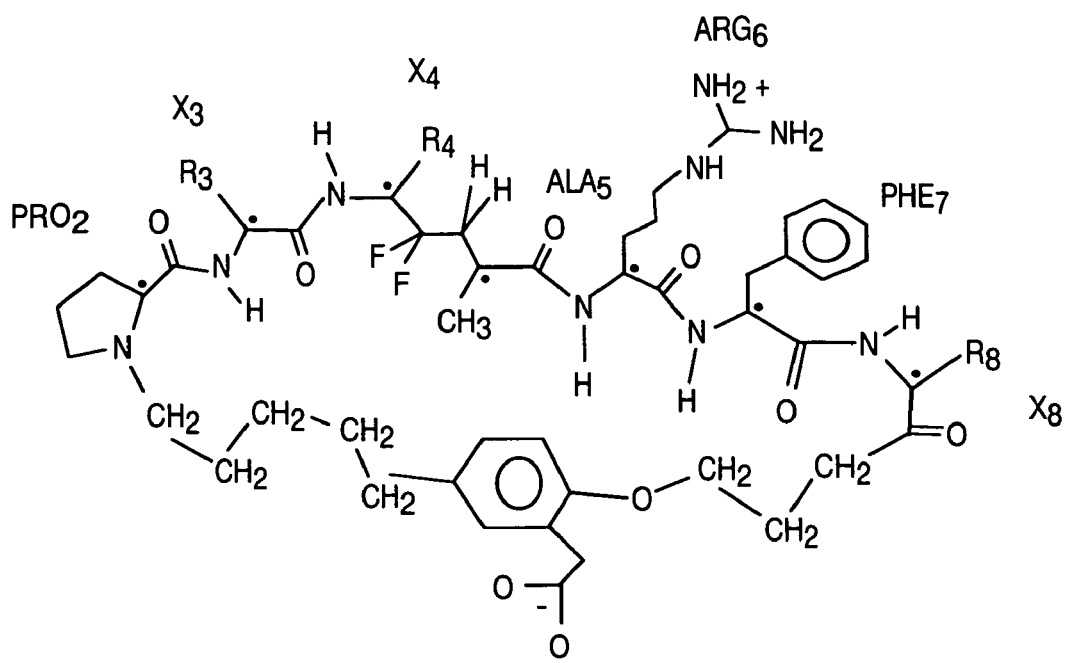
Figure 7B:
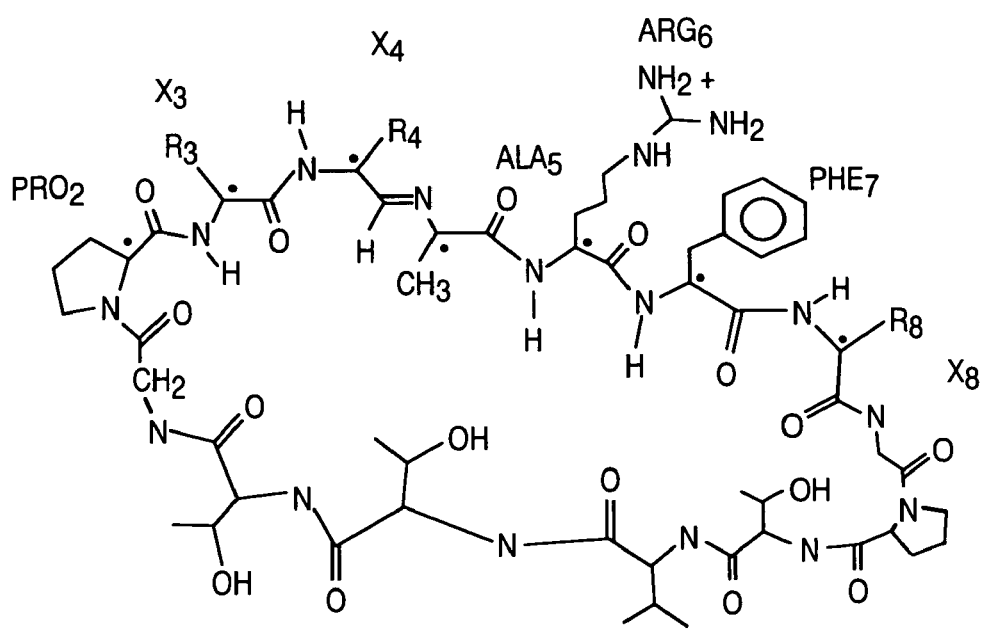

FIG. 7 shows compounds 4.3 and 4.4 according to formula 4. Cmpd 4.3 has a 1,1-difluoroethane group as pseudopeptide and a linker comprising a 2,5 dialkyl benzoic acid linker. Cmpd 4.4 has an imino group as pseudopeptide and a peptide linker Gly-Pro-Thr-Val-Thr-Thr-Gly (SEQ ID NO:30).

Figure 8A:
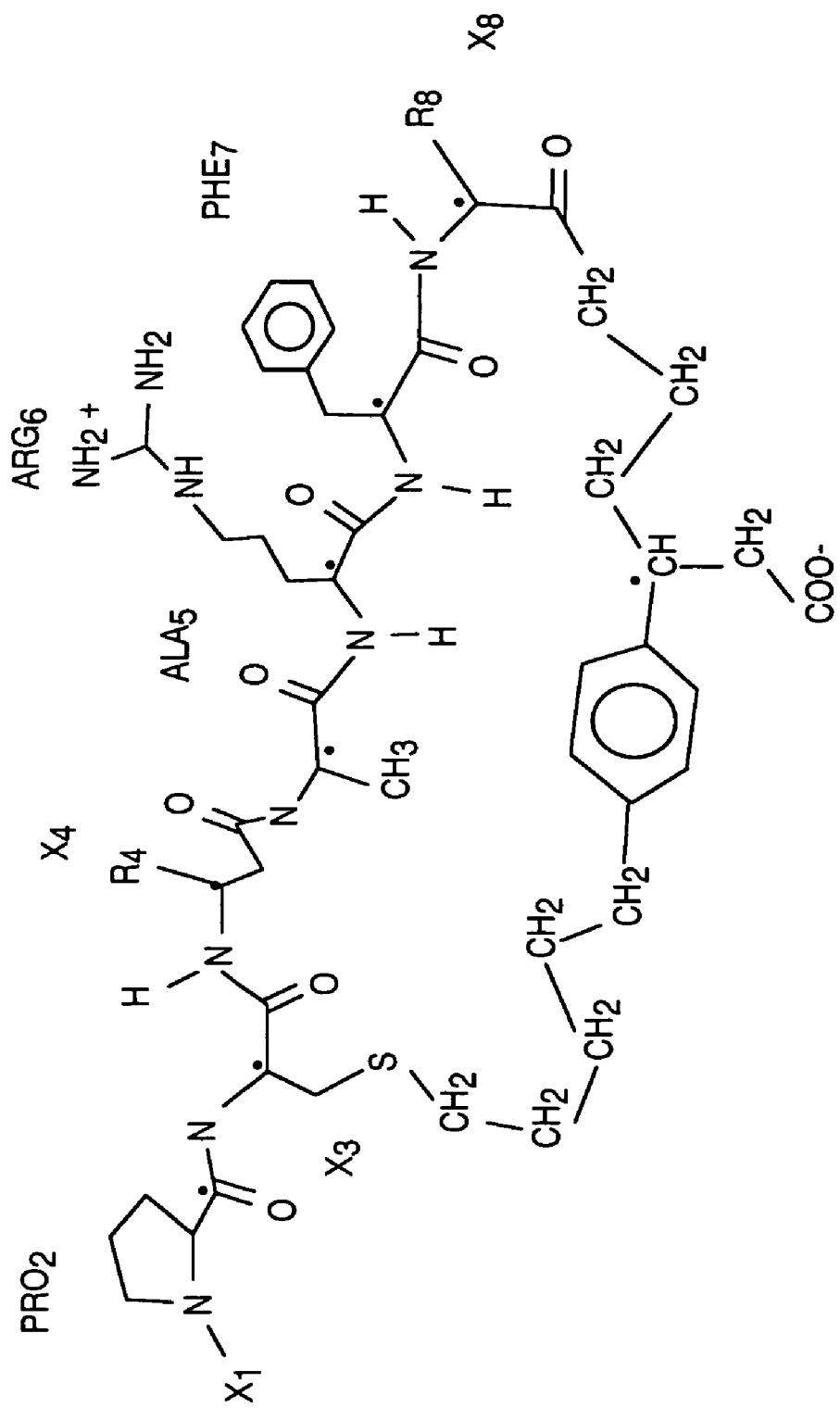
Figure 8B:
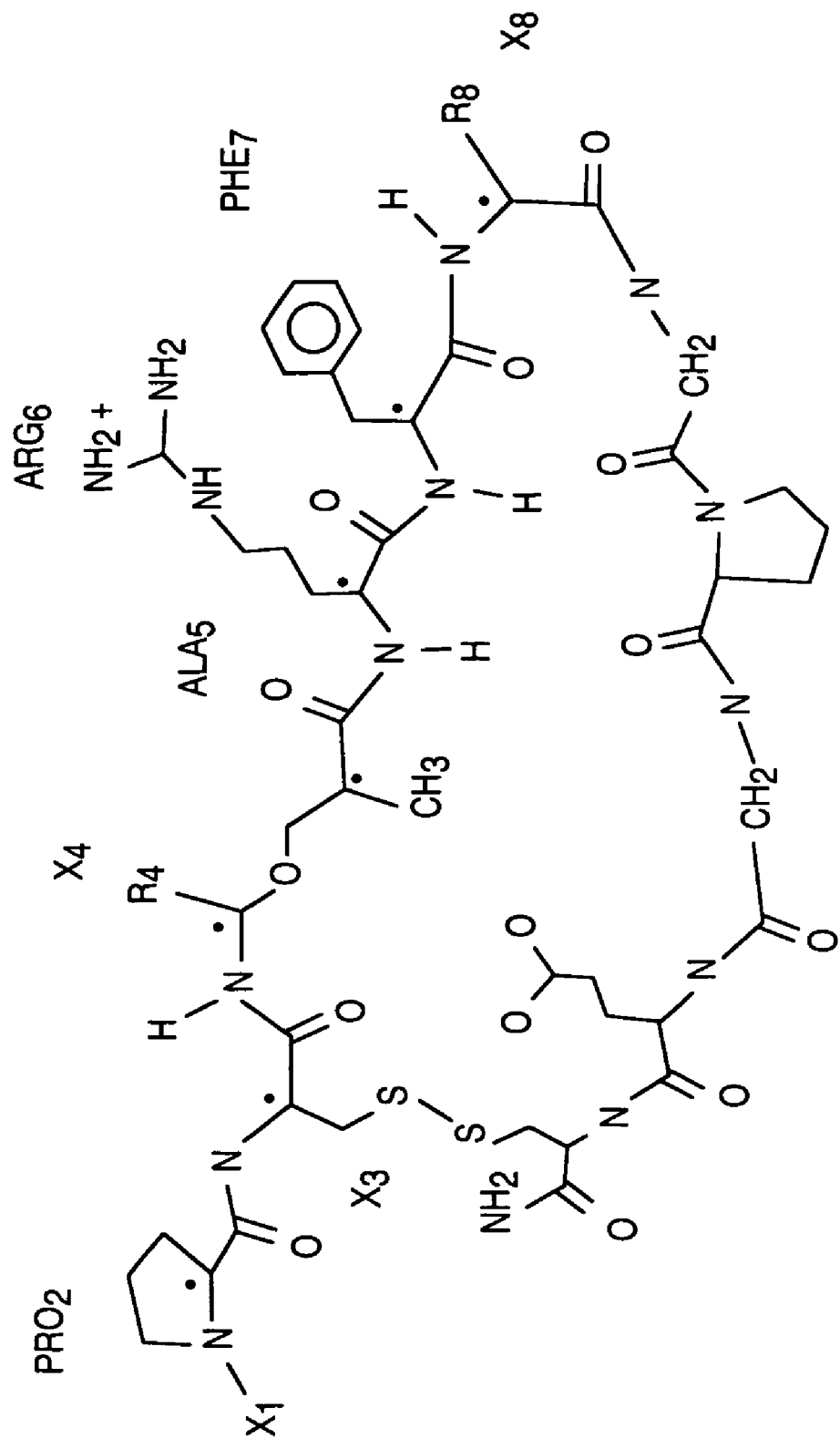

FIG. 8 shows compounds 4.6 (in which the linker contains a p-phenyl group and a carboxylic acid side group) and 4.7 (in which the linker comprises GLY-PRO-GLY-GLU-CYS-$NH_2$) (SEQ ID NO:32) according to formula 4.

Figure 9A:
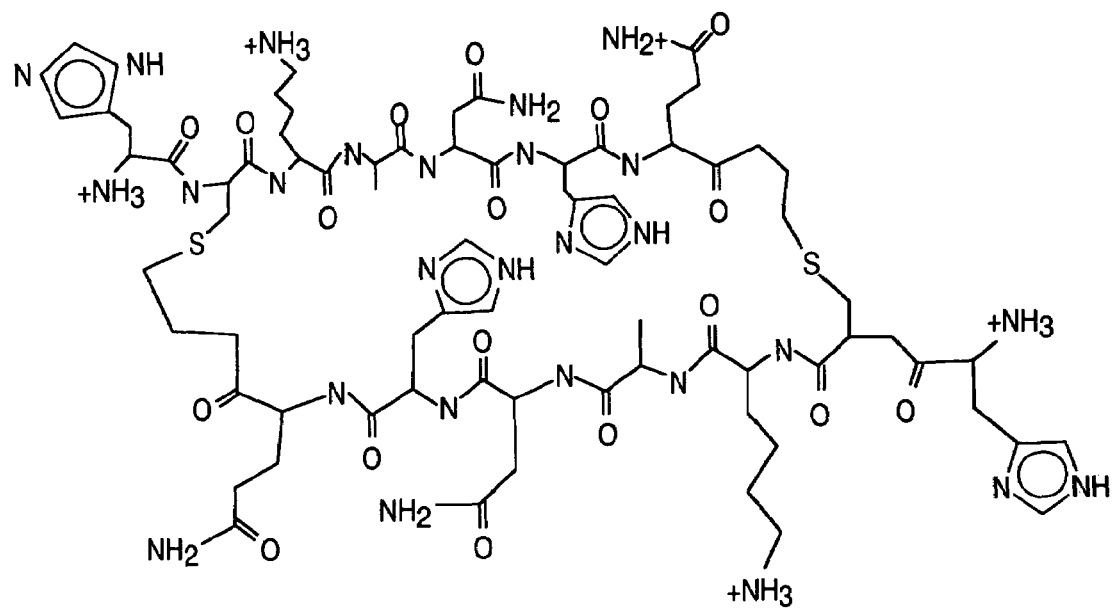
Figure 9B:
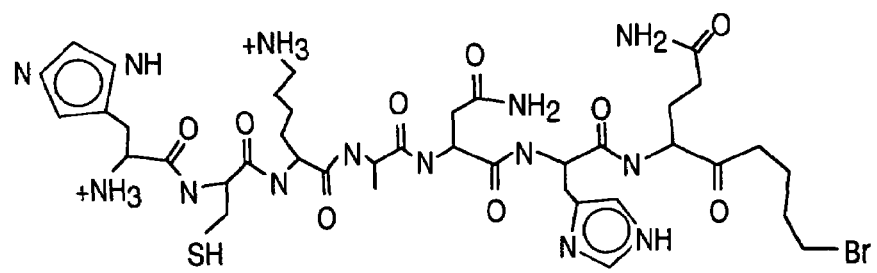
Figure 10A:
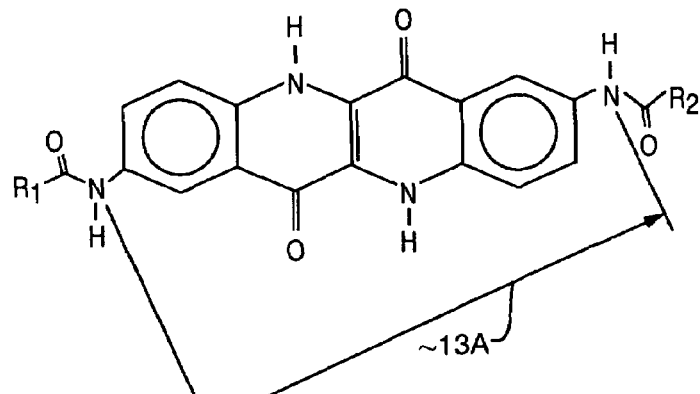
Figure 10B:
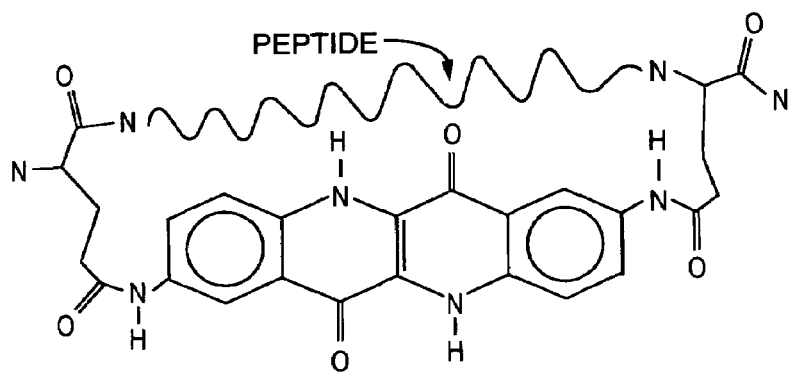
Figure 10C:
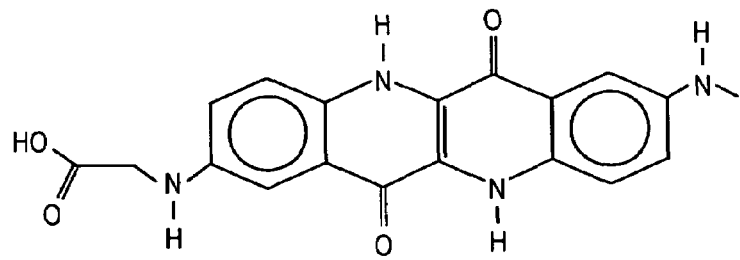
Figure 10D:
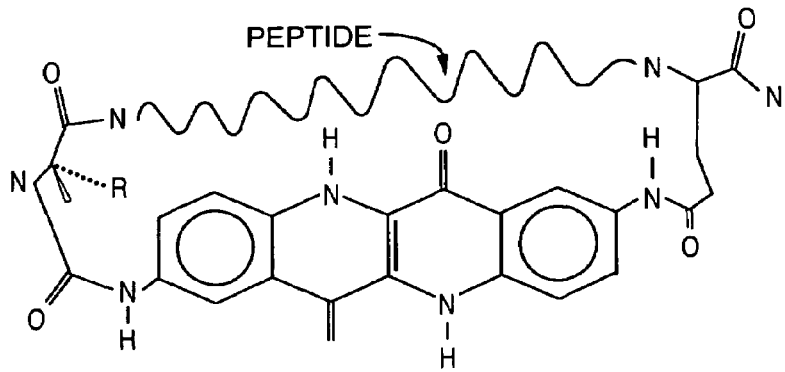
Figure 11A:
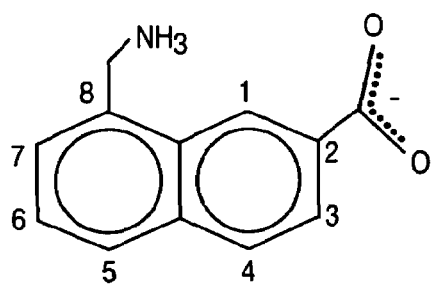
Figure 11E:
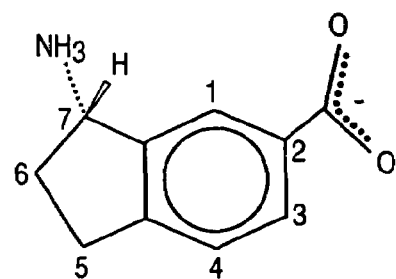
Figure 11B:
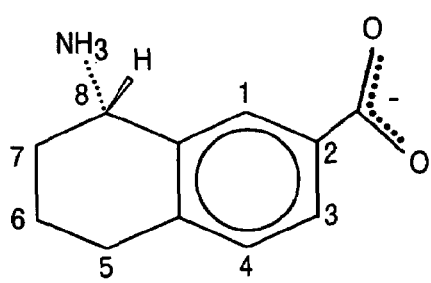
Figure 11F:
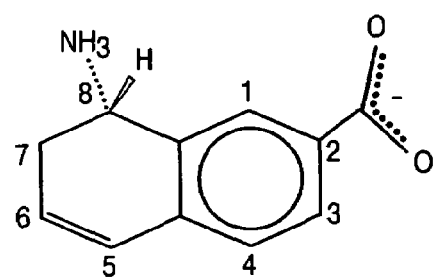
Figure 11C:
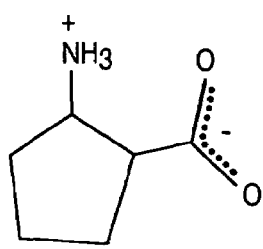
Figure 11G:
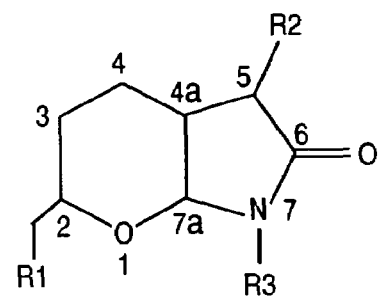
Figure 11D:
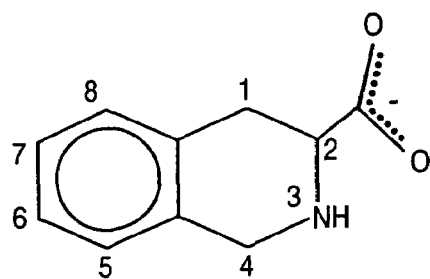
Figure 11H:
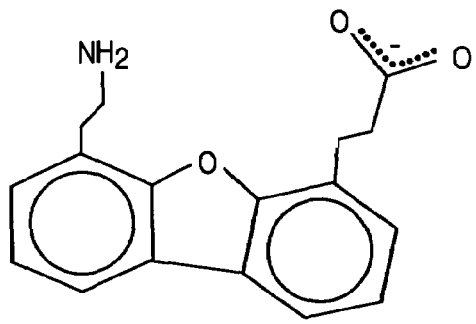
Figure 12B:
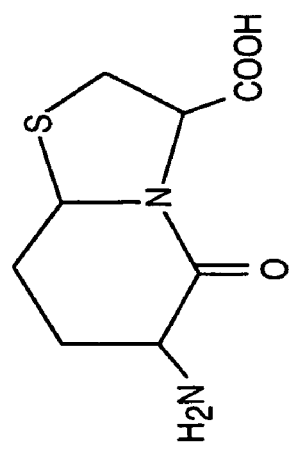
Figure 12D:
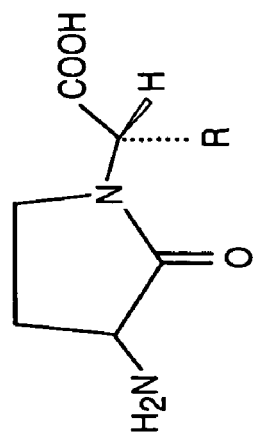
Figure 12A:
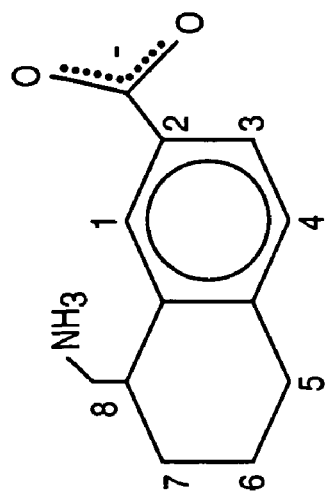
Figure 12C:
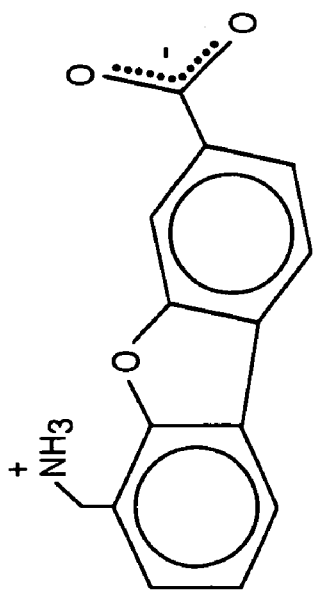

FIGS. 9A and 9B shows a hypotheitcal plasma kallikrein inhibitor. Panel B shows a precursor comprising H-HIS-CYS-LYS-ALA-ASN-HIS-glutamylaldehyde (SEQ ID NO:33):1-(4-bromo-n-butane). Panel A shows the compound formed by reciprocal coupling of the butane moiety to the thiol of a second molecule of the compound in panel B.

FIG. 10A-D shows molecules useful for cyclizing a peptide.

A) shows a diacylaminoepindolidione (KEMP88b), the "exterior" nitrogens are separated by about 13 Å, B) shows diaminoepindolidione joined to a peptide through the side groups of two GLU residues, C) shows carboxymethylaminoaminoepindolidione, D) shows carboxymethylaminoaminoepindolidione joined to the ends of a peptide to form a loop.

FIG. 11A-H shows amino acids that favor a reverse turn,

A) 2-carboxy-8-aminomethylnaphthylene,

B) 2-carboxy-8-amino-5,6,7,8-tetrahydronaphthylene,

C) 1-carboxy-2-aminocyclopentane,

D) tetrahydroisoquinolin carboxylic acid (TIC)

E) 2-carboxy-7-aminoindan

F) 2-carboxy-8-amino-7,8-dihydroxynaphthylene,

G) 2,5,7-trisubstituted 2(S)-5-H-6-oxo-2,3,4,4a,7,7a-hexahydropyrano[2,3-b]pyrrole (CURR93), and
H) 4-(2-aminoethyl)-6-dibenzofuranpropionic acid (DIAZ93).

FIG. 12A-D shows compounds that force a reverse turn in a peptide chain:
A) 4-(2-aminomethyl-6-dibenzofuranethanoic acid,
B) 8-aminomethyl-5,6,7,8-tetrahydro-2-naphthoic acid,
C) Compound attributed to Freidinger et al. (FREI82) in NAGA93,
D) Compound attributed to Nagai and Sato (NAGA85) in NAGA93.

DETAILED DESCRIPTION OF THE PREFERRED EMBODIMENTS

A large number of proteins act as serine protease inhibitors by serving as a highly specific, limited proteolysis substrate for their target enzymes. In many cases, the reactive site peptide bond ("scissile bond") is encompassed in at least one disulfide loop, which insures that during conversion of virgin to modified inhibitor the two peptide chains cannot dissociate.

A special nomenclature has evolved for describing the active site of the inhibitor. Starting at the residue on the amino side of the scissile bond, and moving away from the bond, residues are named P1, P2, P3, etc. (SCHE67). Residues that follow the scissile bond are called P1', P2', P3', etc. It has been found that the main chain of protein inhibitors having very different overall structure are highly similar in the region between P3 and P3' with especially high similarity for P2, $P_1$ and P1' (LASK80 and works cited therein). It is generally accepted that each serine protease has sites S1, S2, etc. that receive the side groups of residues P1, P2, etc. of the substrate or inhibitor and sites S1', S2', etc. that receive the side groups of P1', P2', etc. of the substrate or inhibitor (SCHE67). It is the interactions between the S sites and the P side groups that give the protease specificity with respect to substrates and the inhibitors specificity with respect to proteases.

The serine protease inhibitors have been grouped into families according to both sequence similarity and the topological relationship of their active site and disulfide loops. The families include the bovine pancreatic trypsin inhibitor (Kunitz), pancreatic secretory trypsin inhibitor (Kazal), the Bowman-Birk inhibitor, and soybean trypsin inhibitor (Kunitz) families. (In this application, the term "Kunitz" will be used to refer to the BPTI family and not the STI family.) Some inhibitors have several reactive sites on a single polypeptide chain, and these distinct domains may have different sequences, specificities, and even topologies. One of the more unusual characteristics of these inhibitors is their ability to retain some form of inhibitory activity even after replacement of the P1 residue. It has further been found that substituting amino acids in the $P_5$ to $P_5'$ region, and more particularly the P3 to P3' region, can greatly influence the specificity of an inhibitor. LASK80 suggested that among the BPTI (Kunitz) family, inhibitors with P1 Lys and Arg tend to inhibit trypsin, those with P1=Tyr, Phe, Trp, Leu and Met tend to inhibit chymotrypsin, and those with P1=Ala or Ser are likely to inhibit elastase. Among the Kazal inhibitors, they continue, inhibitors with P1=Leu or Met are strong inhibitors of elastase, and in the Bowman-Kirk family elastase is inhibited with P1 Ala, but not with P1 Leu.

All naturally occurring Kunitz Domain proteins have three disulfide bonds, which are topologically related so that the bonds are a-f, b-d, and c-e ("a" through "f" denoting the order of their positions along the chain, with "a" being closest to the amino-terminal), and the binding site surrounding or adjoining site "b". The term "Kunitz domain protein" is defined, for purposes of the present invention, as being a protease inhibitor which has this fundamental disulfide bond/binding site topology, with the proviso that one of the disulfide bonds characteristic of the naturally occurring protein can be omitted.

Aprotinin-like Kunitz domains (KuDom) are structures of about 58 (typically about 56-60) amino acids having three disulfides: C5-C55, C14-C38, and C30-C51. KuDoms may have insertions and deletions of one or two residues. All naturally occurring KuDoms have all three disulfides. Engineered domains having only two have been made and are stable, though less stable than those having three. All naturally occurring KuDoms have $F_{33}$ and $G_{37}$. In addition, most KuDoms have (with residues numbered to align with BPTI) $G_{12}$, (F,Y, or W) at 21, Y or F at 22, Y or F at 23, Y or W at 35, G or S at 36, G or A at 40, N or G at 43, F or Y at 45, and T or S at 47.

The archetypal KuDom, bovine pancreatic trypsin inhibitor (BPTI, a.k.a. aprotonin), is a 58 a.a. serine proteinase inhibitor. Under the tradename TRASYLOL, it is used for countering the effects of trypsin released during pancreatitis. Not only is its 58 amino acid sequence known, the 3D structure of BPTI has been determined at high resolution by X-ray diffraction, neutron diffraction and by NMR. One of the X-ray structures is deposited in the Brookhaven Protein Data Bank as "6PTI" [sic]. The 3D structure of various BPTI homologues (EIGE90, HYNE90) are also known. At least sixty homologues have been reported; the sequences of 59 proteins of this family are given in Table 13 of Ladner, U.S. Pat. No. 5,233,409 and the amino acid types appearing at each position are compiled in Table 15 thereof. The known human homologues include domains of Lipoprotein Associated Coagulation Inhibitor (LACI) (WUNT88, GIRA89), Inter-α-Trypsin Inhibitor and the Alzheimer beta-Amyloid Precursor Protein (APP-I). Circularized BPTI and circularly permuted BPTI have binding properties similar to BPTI. Some proteins homologous to BPTI have more or fewer residues at either terminus. Kunitz domains are seen both as unitary proteins (e.g., BPTI) and as independently folding domains of larger proteins.

LACI is a human phosphoglycoprotein inhibitor with a molecular weight of 39 kDa. It includes three Kunitz domains.

The cDNA sequence of LACI (SEQ ID NO:25) was determined by Wun et al., *J. Biol. Chem.* 263 6001-6004 (1988). Mutational studies have been undertaken by Girard et al., *Nature* 338 518-520 (1989), in which the putative P1 residues of each of the three kunitz domains contained in the whole LACI molecule were altered from Lys36 to Ile, Arg107 to Leu, and Arg199 to Leu respectively. It has been proposed that kunitz domain 2 is required for efficient binding and inhibition of Factor Xa, while domains 1 and 2 are required for inhbition of Factor VIIa/Tissue Factor activity. The function of LACI kunitz domain 3 is as yet uncertain.

In a preferred embodiment, the KuDom of the present invention is substantially homologous with the first Kunitz Domain ($K_1$) of LACI residues 50-107 of SEQ ID NO:25), with the exception of the kallikrein-binding related modifications discussed hereafter. For prophylaxis or treatment of humans, since BPTI is a bovine protein and LACI is a human protein, the mutants of the present invention are preferably more similar in amino acid sequence to LACI (K1) (residues 50-107 of SEQ ID NO:25) than to BPTI, to reduce the risk of causing an adverse immune response upon repeated administration.

The amino acid sequence of these mutant LACI domains has been numbered, for present purposes, to align them with the amino acid sequence of mature BPTI, in which the first cysteine is at residue 5 and the last at residue 55.

Most naturally occurring Kunitz domains have disulfides between 5:55, 14:38, and 30:51. *Drosophila funebris* male accessory gland protease inhibitor (GeneBank accession number P11424) has no cysteine at position 5, but has a cysteine at position −1 (just before typical position 1); presumably this forms a disulfide to $CYS^{55}$. Engineered Kunitz domains have been made in which one or another of the disulfides have been changed to a pair of other residues (mostly ALA). Proteins having only two disulfides are less stable than those with three.

"Variegation" is semirandom mutagenesis of a binding protein. It gives rise to a library of different but structurally related potential binding proteins. The residues affected ("variable residues") are predetermined, and, in a given round of variegation, are fewer than all of the residues of the protein. At each variable residue position, the allowable "substitution set" is also predetermined, independently, for each variable residue. It may be anywhere from 2 to 20 different amino acids, which usually, but need not, include the "wild type" amino acid for that position. Finally, the relative probabilities with which the different amino acids of the substitution set are expected (based on the synthetic strategy) to occur at the position are predetermined.

Variegation of a protein is typically achieved by preparing a correspondingly variegated mixture of DNA (with variable codons encoding variable residues), cloning it into suitable vectors, and expressing the DNA in suitable host cells.

For any given protein molecule of the library, the choice of amino acid at each variable residue, subject to the above constraints, is random, the result of the happenstance of which DNA expressed that protein molecule.

| BPTI # | (Lac I) | Library Residues | Preferred Residues |
|---|---|---|---|
| 13 | P | L, H, P, R | HP |
| 16 | A | AG | AG |
| 17 | I | F, Y, L, H, I, N, A, S, C, P, R, T, V, DG | NSA |
| 18 | M | all | HL |
| 19 | K | L, W, Q, M, K, A, G, S, P, R, T, V, E | QLP |
| 31 | E | EQ | E |
| 32 | E | EQ | EQ |
| 34 | I | all | STI |
| 39 | E | all | GEA |

In the table above, "library residues" are those permitted to occur, randomly, at that position, in the library, and "preferred residues" are those appearing at that position in at least one of the 10 variants identified as binding to human kallikrein.

At residues 13, 16, 17, 18, 31, and 32, the selections are very strong. At position 34, the selection for either SER or THR is quite strong. At position 39, the selection for GLY is strong. Position 19 seems to be rather tolerant.

The amino acid residues of the binding proteins of the present invention may be characterized as follows (note that the residues are numbered to correspond to BPTI):
(a) the residues involved in disulfide bond formation (C5-C55, C14-C38, and C30-C51);
(b) the residues subjected to variation in the library (13, 16, 17, 18, 19, 31, 32, 34, 39); and
(c) the remaining residues.

At a minimum, the Kunitz domain proteins of the present invention must contain at least two disulfide bonds, at the same (or nearly the same) positions as in LACI(K1)(residues 50-107 of SEQ ID NO:25). The C5-C55 disulfide is the most important, then the C30-C51, and lastly the C14-C38. If a Cys is replaced, it is preferably a conservative non-proline substitution with Ala, and Thr especially preferred. Preferably, three disulfide bonds are formed, at the same, or nearly the same, positions as in LACI(K1)(residues 50-107 of SEQ ID NO:25). By "nearly the same", we mean that as a result of a double mutation, the location of a Cys could be shifted by one or two positions along the chain, e.g., Cys30 Gly/Glx31 Cys.

With regard to the variable residues of the library, it should be appreciated that Applicants have not necessarily sequenced all of the positive mutants in the library, that some of the possible mutant proteins may not actually have been present in the library in detectable amounts, and that, at some positions, only some of the possible amino acids were intended to be included in the library. Therefore, the proteins of the present invention, may, at the aforementioned positions (13, 16-19, 31, 32, 34, 39) in decreasing order of preference, exhibit:
(a) the residues specifically identified as preferred;
(b) conservative (or semi-conservative) substitutions for the residues of (a) above, which were not listed as "library residues";
(c) nonconservative substitutions for the residues of (a) above, which were not listed as library residues;
(d) conservative substitutions for the residues of (a) above, which were listed as library residues In addition, for the protein to be substantially homologous with LACI(K1)(residues 50-107 of SEQ ID NO:25), residue 12 must be Gly, residue 23 must be aromatic, residue 33 must be aromatic, residue 37 must be Gly, (if the 14-28 disulfide bond is preserved, but otherwise is not restricted), and residue 45 must be aromatic.

With regard to the remaining residues, these may be, in decreasing order of preference:
(a) the wild-type amino acid found at that position in LACI (K1)(residues 50-107 of SEQ ID NO:25);
(b) conservative substitutions for (a) above which are also found at that position in one or more of the homologues of BPTI, or in BPTI itself (SEQ ID NO:1), as listed in Table 15 of the '409 patent;
(c) conservative substitutions for (a) above which are not listed at that position in Table 15 of the '409 patent;
(d) other amino acids listed at that position in Table 15 of the '409 patent'
(e) conservative substitutions for the amino acids of (a) above, not already included in (a)-(c);
(f) any other residues, with non-proline residues being preferred.

Additional variegation could give rise to proteins having higher affinity for pKA. The intention is to make a new first loop (residues 10-21) including what we got in the first variation. Table 202 shows variegation for residues 10-21. Above the DNA sequence, underscored AAs are from the selected kallikrein binders while bold AAs are those found in LACI-K1 (residues 50-107 of SEQ ID NO:25). We allow D, E, N, or K at 10 (underscored amino acids have been seen on Kunitz domains at position 10). We allow 8 AAs at 11: {N, S, I, T, A, G, D, V}. Previous variegation had allowed {P,L,H,R} at 13. We selected H very strongly; LACI-K1 (residues 50-107 of SEQ ID NO:25) has P at 13 and no reported Kunitz domain has HIS at 13. In one case, PRO was selected at 13. Judging that $PRO_{13}$ is not optimal, we now allow {E, K, D, Y, Q, H, N}. At 15, we allow K or R. Enzymes that cut after basic residues (K or R) can show two fold tighter binding when the preferred basic residues is available. Which is preferred for a given enzyme may well depend on the other residues in the inhibitor; we will allow both. At 16, we add V or D to the group {A,G} previously allowed. LACI-K1 (residues 50-107 of SEQ ID NO:25) has a hydrophobic residue at 17, but we selected N strongly with S allowed (both are hydrophilic). Thus, we allow either N or S. At 18, we selected HIS strongly with LEU being allowed. We now allow either HIS or LEU. At 19, we allow eleven amino acids: {A, T, S, P, H, N, Y, Q, K, D, E}. HIS, TYR, ASN, and ASP were not allowed in the first variegation. This variegation allows 131,072 DNA sequences and 78,848 amino acid sequences; 99.92% of the amino-acid sequences are new. One preferred procedure is to ligate DNA that embodies this variegation into DNA obtained from selection after the initial variegation at residues 31, 32, 34, and 39. Thus a small population of sequences at these locations is combined with the new variegation to produce a population of perhaps $10^7$ different sequences. These are then selected for binding to human pKA.

A second variegation, shown in Table 204, allows changes at residues 31, 32, 34, 39, 40, 41, and 42. In the first selection, we saw strong selection at positions 31 and 32 and weaker selection at positions 34 and 39. Thus, we now allow more variability at 31 and 32, less variability at 34 and 39, and binary variability at 40, 41, and 42. This variegation allows 131,072 DNA sequences and 70,304 amino-acid sequences. The fraction of amino-acid sequences that are new is 0.997.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

Typically, "substantially homologous" sequences are at least 50%, more preferably at least 80%, identical in sequence, at least over any regions known to be involved in the desired activity. Most preferably, no more than five residues, other than at the termini, are different. Preferably, the divergence in sequence, at least in the aforementioned regions, is in the form of "conservative modifications".

"Conservative modifications" are defined as
(a) conservative substitutions of amino acids as hereafter defined; and
(b) single or multiple insertions or deletions of amino acids at the termini, at interdomain boundaries, in loops or in other segments of relatively high mobility (as indicated, e.g., by the failure to clearly resolve their structure upon X-ray diffraction analysis or NMR). Preferably, except at the termini, no more than about five amino acids are inserted or deleted at a particular locus, and the modifications are outside regions known to contain binding sites important to activity.

Conservative substitutions are herein defined as exchanges within one of the following five groups:
I. Small aliphatic, nonpolar or slightly polar residues: Ala, Ser, Thr (Pro, Gly)
II. Polar, negatively charged residues: and their amides Asp, Asn, Glu, Gln
III. Polar, positively charged residues: His, Arg, Lys
IV. Large, aliphatic, nonpolar residues: Met, Leu, Ile, Val (Cys)
V. Large, aromatic residues: Phe, Tyr, Trp Residues Pro, Gly and Cys are parenthesized because they have special conformational roles. Cys participates in formation of disulfide bonds. Gly imparts flexibility to the chain. Pro imparts rigidity to the chain and disrupts α helices. These residues may be essential in certain regions of the polypeptide, but substitutable elsewhere.

Semi-conservative substitutions are defined to be exchanges between two of groups (I)-(V) above which are limited to supergroup (a), comprising (I), (II) and (III) above, or to supergroup (B), comprising (IV) and (V) above.

Two regulatory DNA sequences (e.g., promoters) are "substantially homologous" if they have substantially the same regulatory effect as a result of a substantial identity in nucleotide sequence. Typically, "substantially homologous" sequences are at least 50%, more preferably at least 80%, identical, at least in regions known to be involved in the desired regulation. Most preferably, no more than five bases are different.

The Kunitz domains are quite small; if this should cause a pharmacological problem, such as excessively quick elimination from the circulation, two or more such domains may be joined by a linker. This linker is preferably a sequence of one or more amino acids. A preferred linker is one found between repeated domains of a human protein, especially the linkers found in human BPTI homologues, one of which has two domains (BALD85, ALBR83b) and another of which three (WUNT88). Peptide linkers have the advantage that the entire protein may then be expressed by recombinant DNA techniques. It is also possible to use a nonpeptidyl linker, such as one of those commonly used to form immunogenic conjugates. For example, a BPTI-like KuDom to polyethyleneglycol, so called PEGylation (DAVI79).

Certain plasma kallikrein-inhibiting Kunitz domains are shown in Table 103. The residues that are probably most important in binding to plasma kallikrein are $H_{13}$, $C_{14}$, $K_{15}$, $A_{16}$, $N_{17}$, $H_{18}$, $Q_{19}$, $E_{31}$, $E_{32}$, and $X_{34}$ (where X is SER or THR). A molecule that presents the side groups of $N_{17}$, $H_{18}$, and $Q_{19}$ plus any two of the residues $H_{13}$, $C_{14}$, $K_{15}$, (or $R_{15}$), $E_{31}$, $E_{32}$, and $X_{34}$ (X=SER or THR) in the corresponding orientation is likely to show strong, specific binding for plasma kallikrein. A basic residue at 15 is NOT thought to be essential.

The compounds are not limited to the side groups found in genetically encoded amino acids; rather, conservative substitutions are allowed. $LYS_{15}$ can be replaced by ARG, ornithine, guanidolysine, and other side groups that carry a positive charge. $ASN_{17}$ can be replaced by other small, neutral, hydrophilic groups, such as (but without limitation) SER, O-methyl serine, GLN, α-amidoglycine, ALA, α-aminobutyric acid, and α-amino-γ-hydroxybutyric acid (homoserine). $HIS_{18}$ could be replaced with other amino acids having one or more of the properties: amphoteric, aromatic, hydrophobic, and cyclic. For example (without limitation), $HIS_{18}$ could be replaced with L-C$^δ$methylhistidine, L-C$^ε$methylhistidine, L-p-aminophenylalanine, L-m-(N,Ndimethylamino)phenylalanine, canavanine (Merck Index 1745), and N-methylasparagine.

A molecule that presents side groups corresponding to, for example, $K_{15}$, $N_{17}$, $H_{18}$, and $E_{32}$ might bind to plasma kallikrein in a way that blocks access of macromolecules to the catalytic site, even though the catalytic site is accessible to small molecules. Thus, in testing possible inhibitors, it is preferred that they be tested against macromolecular substrates.

Ways to Improve Specificity of, For Example, KKII/3#7 for Plasma Kallikrein:

Note that $K_{15}$ or ($R_{15}$) may not be essential for specific binding although it may be used. Not having a basic residue at the P1 position may give rise to greater specificity. The variant KKII/3#7-K15A (SEQ ID NO:31; shown in Table 1017), having an ALA at P1, is likely to be a good plasma kallikrein inhibitor and may have higher specificity for plasma kallikrein relative to other proteases than does NS4. The affinity of KKII/3#7-K15A (SEQ ID NO:31) for plasma kallikrein may be less than the affinity of KKII/3#7 (SEQ ID NO:8) for plasma kallikrein, but in many applications, specificity is more important.

Smaller Domains That Bind Plasma Kallikrein:

Kunitz domains contain 58 amino acids (typically). It is possible to design smaller domains that would have specific binding for plasma kallikrein. Table 50 shows places in BPTI where side groups are arranged in such a way that a disulfide is likely to form if the existing side groups are changed to cysteine. Table 55 shows some "cut-down" domains that are expected to bind and inhibit plasma kallikrein.

The first shortened molecule (ShpKa#1, SEQ ID NO:17) is derived from BPTI and comprises residues 13-39. The mutations P13H, R17N, I18H, I19Q, Q31E, T32E, V34S, and R39G are introduced to increase specific binding to plasma kallikrein. The mutation Y21C is introduced on the expectation that a disulfide will form between $CYS_{21}$ and $CYS_{30}$. It is also expected that a disulfide will form between $CYS_{14}$ and $CYS_{38}$ as in BPTI. These disulfides will cause the residues 13-19 and 31-39 to spend most of their time in a conformation highly similar to that found for the corresponding residues of BPTI. This, in turn, will cause the domain to have a high affinity for plasma kallikrein.

The second shortened molecule (ShpKa#2, SEQ ID NO:18) is also derived from BPTI and comprises residues 13-52. The mutations P13H, R17N, I18H, I19Q, Q31E, T32E, V34T, and R39G are introduced to increase specific binding to plasma kallikrein. Because residues 13-52 are included, the two natural disulfides 14:38 and 30:51 can form.

A third shortened BPTI derivative (ShpKa#3, SEQ ID NO:19) is similar to ShpKa#2 (SEQ ID NO:18) but has the mutations P13H, K15R, R17N, I18H, I19Q, R20C, Q31E, T32E, V34S, Y35C, and R39G. The residues 20 and 35 are close enough in BPTI that a disulfide could form when both are converted to cysteine. At position 34, both ASP and GLY seen to give good plasma kallikrein binders. As we are introducing a new disulfide bond between 35 and 20, it seems appropriate to allow extra flexibility at 34 by using SER.

The fourth shortened molecule (ShpKa#4, SEQ ID NO:20) is derived from the LACI-K1 derivative KKII/3#7 (residues 13-39 OF SEQ ID NO:8) and carries only the mutation F21C. It is likely that a disulfide will form between $CYS_{21}$ and $CYS_{30}$.

ShpKa#5 (SEQ ID NO:21) is related to ShpKa#4 (SEQ ID NO:20) by replacing residues $ILE_{25}$-$PHE_{26}$ with a single GLY. The α carbons of residues 24 and 27 are separated by 5.5 Å and this gap can be bridged by a single GLY.

ShpKa#6 (SEQ ID NO:22) is related to ShpKa#4 (SEQ ID NO:20) by the additional mutations R20C and Y35C. These residues are close in space so that a third disulfide might form between these residues.

ShpKa#7 (SEQ ID NO:23) is related to ShpKa#6 (SEQ ID NO:22) by the mutations N24D, I25V, F26T, and T27E. The subsequence $D_{24}$VTE is found in several Kunitz Domains and reduces the positive charge on the molecule.

ShpKa#8 (SEQ ID NO:24) is related to ShpKa#6 (SEQ ID NO:22) by the mutations I25P, F26D, and T27A. The subsequence $P_{25}$DA is found in the KuDom of *D. funebris*. This has the advantage of inserting a proline and reducing net positive charge. It is not known that reduced positive charge will result in greater affinity or specificity. The ability to change the charge at a site far from the binding site is an advantage.

Non-Kunitz Domain Inhibitors of Plasma Kallikrein Derived from the LACI-K1 Plasma Kallikrein Inhibitors The Kunitz domain binding proteins of the present invention can be used as structural probes of human plasma kallikrein so that smaller protein, small peptidyl, and non-peptidyl drugs may be designed to have high specificity for plasma kallikrein.

The non-Kunitz domain inhibitors of the present invention can be divided into several groups:

1) peptides of four to nine residues,
2) cyclic peptides of five to twenty-five residues,
   a) those closed by disulfides,
   b) those closed by main-chain peptide bonds,
   c) those closed by bonds (other than disulfides) between side groups,
3) compounds in which one or more peptide bonds are replaced by nonpeptidyl bonds which, nonetheless, are somewhat analogous to peptide bonds in length, structure, etc., so-called "pseudopeptides", and
4) compounds in which the side groups corresponding to those of a protein are supported by a framework that is not related to peptides or pseudopeptides.

Inhibitors may belong to more than one of these groups. For example, a compound may be cyclic and have two peptide linkages replaced by "pseudopeptide" linkages, or a compound could have three side groups attached to an organic ring compound with a dipeptide group also attached.

1) Peptides of Four to Nine Residues:

One class of potential inhibitors of plasma kallikrein is peptides of four to nine residues. The peptides are not limited to those composed of the genetically-encodable twenty amino acids. Unless stated otherwise, the levo enantiomer (1- or L-) of chiral amino acids (that is, the conformation about the α carbon is as in naturally occurring genetically-encoded amino acids) is preferred. Peptides of four to nine residues having the sequence of Formula 1 are likely to be specific plasma kallikrein inhibitors.

$$X_1\text{-}X_2\text{-}X_3\text{-}X_4\text{-}X_5\text{-}X_6\text{-}X_7\text{-}X_8\text{-}X_9 \qquad \text{Formula 1}$$

wherein:

→ the first residue may be any one of $X_1$, $X_2$, $X_3$, $X_4$, or $X_5$; the last residue may be either $X_8$ or $X_9$, $X_1$ corresponds to the P4 residue the inhibitor and may be picked from the set comprising {any d or 1 amino acid (having free or blocked amino group) or an amino group (possibly blocked with one of the groups acetyl, formyl, methyl, ethyl, propyl, isopropyl, n-butyl, secondary butyl, tertiary butyl, benzyl, or similar group)}; preferred choices are hydrogen, acetyl, glycine, and formyl, $X_2$ corresponds to the P3 residue and is most preferably 1-HIS; alternatives include (without limitation) L-$C^{\delta}$methylhistidine, L-$C^{\epsilon}$methylhistidine, L-p-aminophenylalanine, L-m-(N,Ndimethylamino)phenylalanine, canavanine (Merck Index 1745), and N-methylasparagine; all the alternatives have one or more of the properties: amphoteric, aromatic, hydrophobic, and cyclic, as does HIS, $X_3$ corresponds to the P2 residue and may be any 1 amino acid, preferably uncharged and hydrophobic; if $X_3$ is cysteine, the sulphur is blocked by one of a) a second cysteine residue, b) a thiol reagent, c) an alkyl group, if $X_3$ is not cysteine, then PRO is a preferred choice because the ϕ of $CYS_{14}$ is in the range accessible to PRO and the side group of PRO is not dissimilar to the disulfide group, other preferred alternatives at $X_3$ include 1-MET, 1-GLN, 1-pipecolic acid (Merck Index 7425), 1-2-azitidinecarboxylic acid (Merck Index 923), 1-LEU, 1-ILE, 1-VAL, cycloleucine (Merch Index 2740), 1-α-aminobutylric acid, 1-aminocyclopropane-1-carboxylic acid, and 1-methoxyalanine, $X_4$ corresponds to the P1 residue and is most preferably 1-LYS, 1-ARG, 1-ornithine, or 1-guanidolysine (i.e. $NH_2$—CH(COOH)—$(CH_2)_4$—NH—C—$(NH_2)_2$+); 1-ALA, 1-SER, and GLY are preferred alternatives, $X_5$ corresponds to the P1' residue and is most preferably ALA if $X_4$ is present; 1-PRO, GLY, and 1-SER are preferred alternatives,; $X_5$ may be any amino acid if $X_1$-$X_4$ are absent, $X_6$ corresponds to the P2' residue and is most preferably 1-ASN, 1-SER, 1-GLN; other amino acids having small, neutral, hydrophilic groups, such as (but without limitation) O-methyl serine, α-amidoglycine, α-aminobutyric acid, β-fluoroalanine, N-methylasparagine, N,N-dimethylasparagine, and α-amino-γ-hydroxybutyric acid (homoserine), are preferred alternatives, $X_7$ corresponds to the P3' residue and is most preferably HIS; preferred alternatives include, for example and without limitation, L-C$^\delta$methylhistidine, L-C$^\epsilon$methylhistidine, L-p-aminophenylalanine, L-m-(N,Ndimethylamino)phenylalanine, canavanine (Merck Index 1745), and N-methylasparagine; all the alternatives have one or more of the properties: amphoteric, aromatic, hydrophobic, and cyclic, as does HIS, $X_8$ corresponds to the P4' residue and most preferably is GLN; other neutral residues including, for example and without limitation, ASN, α-amino-δ-amidoadipic acid, HIS, and α-amino-ε-amidopimelic acid. The preferred alternative all have minimal size and no charged groups, and $X_9$ corresponds to the p5' residue and may be any 1- or d-amino acid, preferably 1-ARG, 1-LEU, or 1-ALA (which occur frequently at this position of Kunitz Domains), or GLU, ASP, or other amino acids having acidic side groups (which might interact with plasma kallikrein in place of $GLU_{32}$ or $GLU_{31}$), or homoserine or other amino acid having a hydroxyl, or $X_9$ may be a free or blocked carboxyl group of $X_8$ or $X_9$ may be a free or blocked amide group of $X_8$; if $X_5$ is the first amino acid, then $X_9$ is present.

These compounds can be synthesized by standard solid-phase peptide synthesis (SPPS) using tBoc or Fmoc chemistry. Synthesis in solution is also allowed. There are many references to SPPS, including *Synthetic Peptides*, Edited by Gregory A Grant, W H Freeman and Company, New York, 1992, hereinafter GRAN92.

Examples of class 1 include:

1.1) +$NH_2$-$GLY_1$-HIS-PRO-$LYS_4$-$ALA_5$-ASN-HIS-GLN-$LEU_9$-$NH_2$ (SEQ ID NO:34; 9 amino acids), 1.2) +$NH_2$-HIS-$PRO_3$-$ARG_4$-ALA-ASN-HIS-$GLN_8$-COO— (SEQ ID NO:35; 7 amino acids), 1.3) +$NH_2$-$PRO_3$-$ARG_4$-ALA-ASN-$HIS_7$-COOC2H5 (SEQ ID NO:36; 5 amino acids), 1.4) $CH_3$CO—NH—$CH_2$—CO-HIS-MET-$LYS_4$-ALA-ASN-HIS-GLN-GLU-COO— (SEQ ID NO:37; $X_1$ is acetylglycine, 9 amino acids), 1.5) 1-pipecolyl-1-ornithinyl$_4$-$ALA_5$-ASN-L-C$^\delta$methylhistidYL-GLN-$NH_2$ (6 amino acids), and 1.6) 1-2-azitidinyl-1-guanidolysyl$_4$-PRO-ASN-HIS-1-α-aminopimelamideyl-GLU-$CONH_2$ (7 amino acids).

2) Cyclic Peptides of from About 8 to About 25 Amino Acids:

A second class of likely plasma kallikrein inhibitors are cyclic peptides of from about 8 to about 25 residues in which Formula 1 is extended to allow cyclization between $X_8$ or $X_9$ and one of: 1) $X_1$, 2) $X_2$, 3) $X_3$, 4) $X_4$, 5) $X_5$, or 6) the side group of one these residues. The amino acids of this class are not restricted to the twenty genetically encodable amino acids. Closure to the amino terminus of residues in cases 1-5 involves standard peptide chemistry. Leatherbarrow and Salacinski (LEAT91) report "design of a small peptide-based proteinase inhibitor by modeling the active-site region of barley chymotrypsin inhibitor 2." This twenty-amino-acid peptide has a $K_D$ for chymotrypsin of 28 pM. If the side group of $X_3$ contains a free thiol, as in CYS, then the peptide may be extended to include a second CYS that will form a disulfide with $CYS_3$. Thus, the sequences of the Formulae 2.1 through 2.12 are likely to be specific inhibitors of plasma kallikrein.

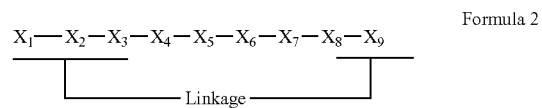

Formula 2

Wherein:

→ the first residue may be any one of $X_1$, $X_2$, or $X_3$, $X_1$ corresponds to the P4 residue the inhibitor and may be picked from the set comprising {any d or l amino acid (having free or blocked amino group) or an amino group (possibly blocked with one of the groups acetyl, formyl, methyl, ethyl, propyl, isopropyl, n-butyl, secondary butyl, tertiary butyl, benzyl, or similar group)}; preferred choices are hydrogen, acetyl, glycine, and formyl, $X_2$ corresponds to the P3 residue and is most preferably 1-HIS; alternatives include (without limitation) L-C$^\delta$methylhistidine, L-C$^\epsilon$methylhistidine, L-p-aminophenylalanine, L-m-(N,Ndimethylamino)phenylalanine, canavanine (Merck Index 1745), and N-methylasparagine; all the alternatives have one or more of the properties: amphoteric, aromatic, hydrophobic, and cyclic, as does HIS, $X_3$ corresponds to the P2 residue and may be any 1 amino acid, preferably uncharged and hydrophobic; if $X_3$ is cysteine, the sulphur is blocked by one of a) a second cysteine residue, b) a thiol reagent, c) an alkyl group, if $X_3$ is not cysteine, then PRO is a preferred choice because the φ of $CYS_{14}$ is in the range accessible to PRO and the side group of PRO is not dissimilar to the disulfide group, other preferred alternatives at $X_3$ include 1-MET, 1-GLN, 1-pipecolic acid (Merck Index 7425), 1-2-azitidinecarboxylic acid (Merck Index 923), 1-LEU, 1-ILE, 1-VAL, cycloleucine (Merck Index 2740), 1-α-aminobutylric acid, 1-aminocyclopropane-1-carboxylic acid, and 1-methoxyalanine, $X_4$ corresponds to the P1 residue and is most preferably 1-LYS, 1-ARG, 1-ornithine, or 1-guanidolysine (i.e. $NH_2$—CH(COOH)—$(CH_2)_4$—NH—C—$(NH_2)_2$+); 1-ALA, 1-SER, and GLY are preferred alternatives, $X_5$ corresponds to the P1' residue and is most preferably ALA if $X_4$ is present; 1-PRO, GLY, and 1-SER are preferred alternatives,; $X_5$ may be any amino acid if $X_1$-$X_4$ are absent, $X_6$ corresponds to the P2' residue and is most preferably 1-ASN, 1-SER, 1-GLN; other amino acids having small, neutral, hydrophilic groups, such as (but without limitation) O-methyl serine, α-amidoglycine, α-aminobutyric acid, β-fluoroalanine, N-methylasparagine, N,N-dimethylasparagine, and α-amino-γ-hydroxybutyric acid (homoserine), are preferred alternatives, $X_7$ corresponds to the P3' residue and is most preferably HIS; preferred alternatives include, for example and without limitation, L-C$^\delta$methylhistidine, L-C$^\epsilon$methylhistidine, L-p-aminophenylalanine, L-m-(N,Ndimethylamino)phenylalanine, canavanine (Merck Index 1745), and N-methylasparagine; all the alternatives have one or more of the properties: amphoteric, aromatic, hydrophobic, and cyclic, as does HIS, $X_8$ corresponds to the P4' residue and most preferably is GLN; other neutral residues including, for example and without limitation, ASN, α-amino-δ-amidoadipic acid, HIS, and α-amino-ε-amidopimelic acid. The preferred alternative all have minimal size and no charged groups, and $X_9$ corresponds to the p5' residue and may be any 1- or d-amino acid, preferably 1-ARG, 1-LEU, or 1-ALA (which occur frequently at this position of Kunitz Domains), or GLU, ASP, or other amino acids having acidic side groups (which might interact with plasma kallikrein in place of GLU$_{32}$ or GLU$_{31}$), or homoserine or other amino acid having a hydroxyl, or $X_9$ may be a free or blocked carboxyl group of $X_8$ or $X_9$ may be a free or blocked amide group of $X_8$; if $X_5$ is the first amino acid, then $X_9$ is present, Linkage is a collection of atoms that connect one of $X_8$ or $X_9$ to one of $X_1$, $X_2$, or $X_3$. The linkage could be closed by any one or more of disulfide bonds, peptide bonds, other covaluent bonds. The linkage is designed to bend sharply after the recognition sequence; sequences such as GLY-PRO, PRO-GLY, GLY-GLY, SER-GLY, and GLY-THR which are known to favor turns are preferred after the recognition sequence ($X_4$-$X_8$) and (for those cases in which the loop is closed by main-chain peptide bonds) before the lowest-numbered residue of Formula 2; the linkage could be picked from the set comprising:

1) —(CH$_2$)n- where n is between 1 and about 18;

2) —CH$_2$—(O—CH$_2$—CH$_2$)n- where n is between 1 and about 6;

3) saccharides comprising one to about five hexose, pentose, or other rings, sugars offering the advantage of favoring solubility;

4) diaminoepindolidione, 2,6-diaminonaphthylene, 2,6-diaminoanthracene, and similar rigid diamines joined to the carboxylic acid groups either at the C-terminus or in the side groups of ASP, GLU, or other synthetic amino acids;

5) 2,6-dicarboxynaphthylene, 2,6-dicarboxyanthracene, and similar rigid dicarboxylic acids joined to primary amino groups on the peptide, such as the α amino group or the side groups of LYS or ornithine;

6) one or more benzene, naphthylene, or anthracene rings or their heterocyclic analogues, having acidic, oxymethyl, basic, halo, or nitro side groups and joined through alkyl or ether linkages.

The linker should not be too hydrophobic, especially if it is flexible. A chain of methylene groups is likely to undergo "hydrophobic collapse" (Dan Rich paper.) Ether linkages are chemically stable and avoid the tendency for the linker to collapse into a compact mass.

Some examples, without limitation, of Formula 2 are:

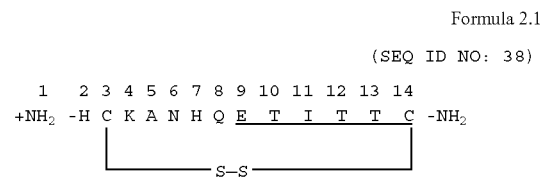

Formula 2.1
(SEQ ID NO: 38)

In Formula 2.1, $X_1$ is an amino group, $X_2$ is HIS, $X_3$ is CYS, $X_4$ is LYS, $X_9$ is GLU, and the linker is -THR-ILE-THR-THR-CYS-NH$_2$. The loop is closed by a disulfide. Table 220 contains the distances between α carbons of the residues 11 through 21 and 32, 32, and 34 in BPTI. CYS$_3$ in Formula 2.1 corresponds to CYS$_{14}$ of BPTI and GLU$_9$ corresponds to ARG$_{20}$. These residues are separated (in the desired conformation) by 14.2 Å. Thus the five residue linker can span this gap. The use of THR and ILE favors an extended conformation of the linker. GLU$_9$ is intended to interact with the components of plasma kallikrein that interact with GLU$_{31}$ and GLU$_{32}$ in the Kunitz-domain KKII/3#7 (SEQ ID NO:8) plasma kallikrein inhibitor.

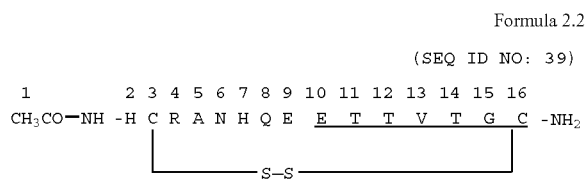

Formula 2.2
(SEQ ID NO: 39)

In Forumula 2.2, $X_1$ is an acetate group, $X_3$ is CYS, $X_4$ is ARG, $X_9$ is GLU, and the linker is -GLU$_{10}$-THR-THR-VAL-THR-GLY-CYS-NH$_2$. The loop is closed by a disulfide. This differs from 2.1 in having two acidic residues where the chain is likely to turn and where these acidic side groups can interact with those components of plasma kallikrein that interact with GLU$_{31}$ and GLU$_{32}$ in the Kunitz-domain KKII/3#7 (SEQ ID NO:8) plasma kallikrein inhibitor.

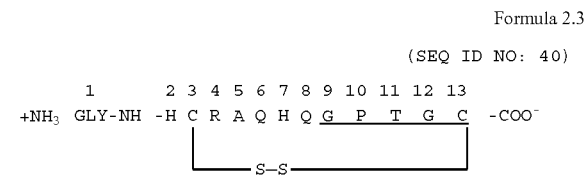

Formula 2.3
(SEQ ID NO: 40)

In Formula 2.3, $X_1$ is a glycine, $X_2$ is HIS, $X_3$ is CYS, $X_4$ is ARG, $X_6$ is GLN, $X_9$ is GLY (actually part of the linker), and the linker is -GLY$_9$-PRO-THR-GLY-CYS-NH$_2$.

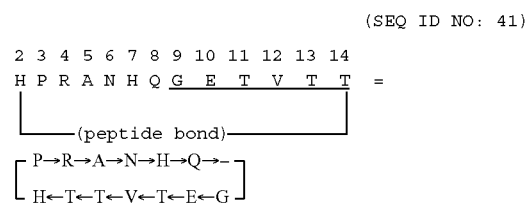

(SEQ ID NO: 41)

In Formula 2.4, the loop is closed by a peptide bond bewteen $THR_{14}$ and $HIS_2$. The compound may be synthesized starting at any point and then cyclized. $X_3$ is PRO and $X_4$ is ARG. The TTVT sequence favors extended structure due to the branches at the β carbons of the side groups. $GLY_9$ favors a turn at that point. $GLU_{10}$ allows interaction with those components of plasma kallikrein that interact with $GLU_{31}$ and $GLU_{32}$ of KKII/3#7 (SEQ ID NO:8). $GLU_{10}$ of formula 2.4 could be replaced with other amino acids having longer acidic side groups such as α-aminoadipic acid or α-aminopimelic acid.

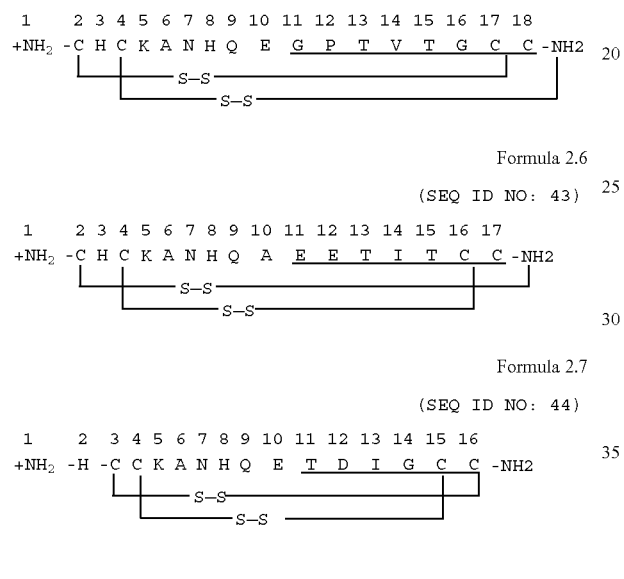

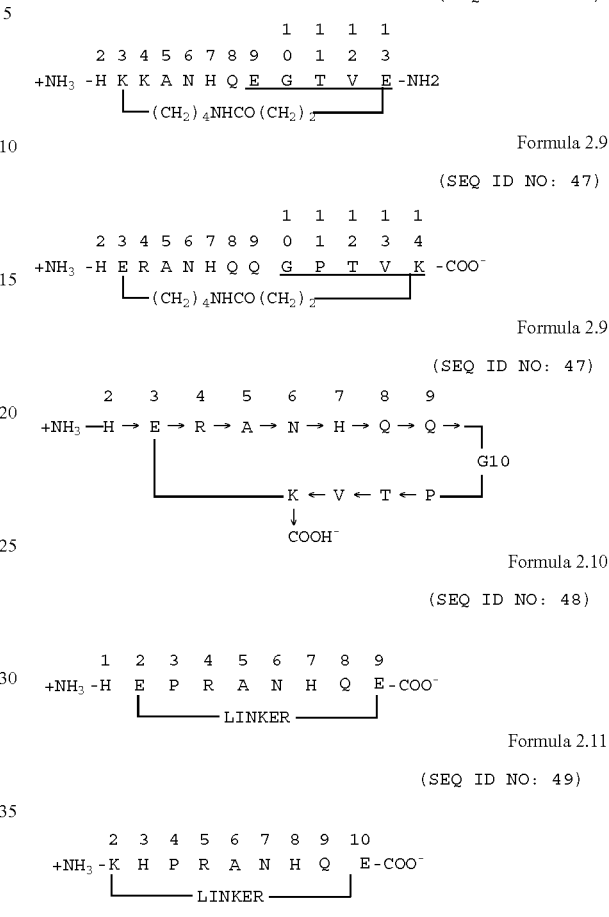

In formulae 2.5, 2.6, and 2.7 there are two disulfides. Having two disulfides is likely to give the compound greater rigidity and increase the likelihood that the sequence from 5 to 10 is extended. Having two consecutive CYSs favors formation of disulfides to other CYSs, particularly those at the beginning of the peptide. In formula 2.5, the disulfides are shown from $C_2$ to $C_{17}$ and $C_4$ to $C_{18}$. This bonding may not be as favorable to proper conformation of residues 5 through 10 as is the bonding $C_2$ to $C_{17}$ and $C_4$ to $C_{16}$ as shown in formula 2.6. Which of these forms is probably most strongly influenced by the amino-acid sequence around the cysteines and the buffer conditions in which the molecule folds. Placing charged groups before and after the cysteines may favor the desired structure. For example, $D_1C_2HC_4K_5ANHQEGPTVD_{15}C_{16}C_{17}K_{18}$ (SEQ ID NO:45) would have $D_1$ close to $K_{18}$ and $K_5$ close to $D_{15}$ in the desired structure, but would have $D_1$ close to $D_15$ and $K_5$ close to $K_{18}$ in the less preferred structure.

Optionally, the side group of $X_3$ in Formula 2 could be other than CYS but such that it can selectively form a cross-bridge to a second residue in the chain. As discussed in GRAN92 (p. 141) selective deprotection of primary amine and carboxylic acid side groups allows selective formation of intrachain crosslinks.

Formulae 2.8, 2.9, 2.10, and 2.11 show cyclic peptides which are likely to inhibit plasma kallikrein specifically in which the loop is closed by a peptide bond or bonds between the side groups of amino acids. During synthesis, the substrates for $LYS_3$ and $GLU_{13}$ (formula 2.8), $GLU_3$ and $LYS_{14}$ (formula 2.9), $GLU_2$ and $GLU_9$ (formula 2.10), and $LYS_2$ and $LYS_{10}$ (formuola 2.11) are blocked differently from other reactive side groups of their respective peptides so that these side groups can be deprotected while leaving the other groups blocked. The loop is then closed and the other side groups deprotected.

The α carbons of LYS and GLU residues that are joined by a peptide bond through the side groups may be separated by up to about 8.5 Å. In BPTI (SEQ ID NO:1), the α carbons of $CYS_{14}$ and $ARG_{17}$ are separated by 8.9 Å. The second version of Formula 2.9 shows the peptide chain folded back after $GLY_{10}$; $PRO_{11}$ is approximately as far from the α carbon of residue 3 as is the α carbon of $GLN_9$; $THR_{12}$ is about as far from residue 3 as is $GLN_8$; and so forth, so that $LYS_{14}$ is about as far from residue 3 as is $ARG_6$, which would be about 8.9 Å if the peptide is in the correct conformation. The peptide of formula 2.8 is one amino acid shorter. The sequence differs by omission of a PRO, so the chain should be less rigid.

For formula 2.10, the loop is closed by formation of two peptide bonds between the side groups of $GLU_2$ and $GLU_9$ with 2,6 bisaminomethylnaphthylene (FIG. 4, panel E). In Formula 2.11, residues 2 and 9 are lysine and 2,6 biscarboxynaphthylene (FIG. 4, panel D) could be used. Linkers of this sort have the advantage that the linker not only bridges the gap, but that it also keeps the joined amino acids separated by at least about 8 Å. This encourages the peptide to fold into the desired extended conformation.

Loop closure by peptide bond or bonds has the advantage that it is not sensitive to reduction as are disulfides. Unnatural amino acids have different cross-linkable side groups may be used. In particular, acid side groups having more methylene groups, aryl groups, or other groups are allowed. For example, the side groups —CH$_2$-p-C$_6$H$_4$—COOH, -p-C$_6$H$_4$—CH$_2$—COOH, —(CH$_2$)$_3$—COOH, and -(transCH=CH)—CH$_2$—COOH could be used. Also, side groups (other than that of LYS) carrying amino groups may be used. For exampel, —(CH$_2$)$_2$—NH$_3$+, —(CH$_2$)$_3$—NH$_3$+, —(CH$_2$)$_5$—NH$_3$+, —CH$_2$-2-(6-aminomethylnaphthyl) (shown in FIG. 3, panel A), —CH$_2$-2-(6-carboxymethylnaphthyl) (shown in FIG. 3, panel B), —CH$_2$—CH$_2$-2-(6-aminomethylnaphthyl) (shown in FIG. 3, panel D), —CH$_2$—CH$_2$-2-(6-carboxymethylnaphthyl) (shown in FIG. 3, panel E), and —CH$_2$-p-C$_6$H$_4$—CH$_2$—NH$_3$+ are suitable.

The naphthylene derivatives shown in FIGS. 3 and 4 have the advantage that, for the distance spanned, there are relatively few rotatable bonds.

Another alternative within Formula 2 is a repeated cyclic compound: for example, Formula 2.12
(SEQ ID NO: 50)

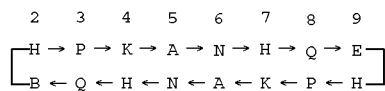

Formula 2.12' has two copies of the recognition sequence (HX tandemly repeated and cyclized. A GLY is inserted to facilitate a turn.

Let Б be an amino-acid analogue that forces a β turn, many of which are known in the art. Then compounds of formula 2.12 are likely to have the desired conformation and to show highly specific plasma kallikrein binding.

Formula 2.12
(SEQ ID NO: 50)

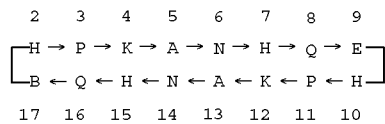

Related compounds encompassed in formula 2 include cyclic(PKANHQБPKANHQБ; SEQ ID NO:50) and cyclic(HMKANHQБHMKANHQБ; SEQ ID NO:51).

Furthermore, one might increase the specificity to 2.12 by replacing the P1 amino acid (K$_4$ and K$_{12}$) with a non-basic amino acid such as ALA, SER, or GLY.

Formula 2.13
(SEQ ID NO: 52)

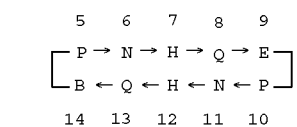

Formula 2.13 embodies two copies of the NHQ subsequence, having the P1' ALA replaced by PRO (to force the appropriate phi angle). Cyclic (ANHQБANHQБ; SEQ ID NO:53) is also a likely candidate for specific plasma kallikrein binding.

Also encompassed by formula 2 are compounds like that shown in FIG. 10 having the sequence cyclo(bis H-HIS-CYS-LYS-ALA-ASN-HIS-GLN*; SEQ ID NO:54) wherein GLN* is the modified moiety shown and the cycle is closed by two thioether linkages.

Pseudopeptides:

As used herein, a "pseudopeptide" is a linkage that connects two carbon atoms which correspond to the carbons of amino acids and which are called the "bridge-head atoms". The pseudopeptide holds the bridge-head atoms at an appropriate separation, approximately 3.8 Å. The pseudopeptide is preferably planar, holding the bridge-head atoms in the same plane as most or all of the atoms of the pseudopeptide. Typically, a pseudopeptide has an amino group and a carboxylic acid group so that is corresponds roughly to a dipeptide that can be introduced into a peptide by standard Fmoc, tBoc, or other chemistry.

In BPTI, the carbonyl oxygen of K$_{15}$ projects toward the exterior while the amine nitrogen of A$_{16}$ points toward the interior of BPTI. Thus, psuedopeptides that preserve the carbonyl group are preferred over those that do not. Furthermore, pseudopeptides that favor the atomic arrangement found at residues 15 and 16 of Kunitz domains are particularly favored at residues 15-16 for compounds of the present invention. At other positions, pseudopeptides that favor the observed conformation are preferred.

FIGS. 1 and 2 show twelve examples of pseudopeptides; other pseudopeptides may be used. Of these, ψ1, ψ2, ψ3, ψ5, ψ6, ψ7, ψ8, ψ9, ψ11, and ψ12 maintain the same number of atoms between nominal C$_α$s. ψ4 and ψ10 add an extra atom in the linkage. ψ2, ψ4, ψ6, ψ7, ψ8, ψ9, and ψ10 maintain a carbonyl oxygen. ψ1, ψ3, ψ5, can carry electronegative groups in a place similar to that of the carbonyl oxygen if X$_1$ is F or —O-alkyl (especially —O—CH$_3$ or —O—CF$_3$). The pseudopeptide bond plays several roles. First, the pseudopeptide prevents hydrolysis of the bond. To do this, it is usually enough that the bond be stable in water and that at least one atom of the peptide be changed. It may be sufficient to alkylate the peptide amide. Peptides having PRO at P1' are often highly resistant to cleavage by serine proteases. A second role of the pseudopeptide if to favor the desired conformation of the residues joined by the pseudopeptide. Thirdly, the pseudopeptide provides groups having suitable charge, hydrogen-bonding potential, and polarizability. Even so, it must be remembered that only a true peptide will have the same geometry, charge distribution, and flexibility as a peptide. Changing one atom will alter some property. In most cases, the binding of the pseudopeptide derivative to the target protease will be less tight than is the binding of the Kunitz domain from which sequence information was taken. Nevertheless, it is possible that some pseudopeptide derivatives will bind better than true peptides. To minimize the loss of affinity, it is desirable:

1) that the pseudopeptide itself be at least roughly planar,
2) that the pseudopeptide keep the two joined α carbons in the plane of the pseudopeptide, and
3) that the separation of the two joined α carbons be approximately 3.8 Å.

$\psi 1$, $\psi 6$, $\psi 7$, $\psi 8$, and $\psi 11$ are expected to keep the α carbons in the plane of the pseudopeptide. In $\psi 8$ carbons 1, 2, and 6 plus the carbonyl O define the plane of the pseudopeptide. $\psi 8$ and $\psi 9$ are likely to be approximately consistent with the geometry between residues 15 and 16 of a Kunitz domain. The cyclohexone or cyclohexenone ring does not conflict with groups that are included in the compounds of the present invention, but would conflict with atoms of a Kunitz domain.

Kline et al. (KLIN91) have reported use of —CH$_2$—CO—NH— and —CH$_2$—NH— in hirulogs that bind plasma kallikrein. DiMaio et al. (DIMA91) have reported using —CO—CH$_2$— as a pseudopeptide bond in hirulogs that bind plasma kallikrein. Angliker et al. (ANGL87) report synthesis of lysylfluoromethanes and that Ala-Phe-Lys-CH$_2$F is an active-centre-directed inhibitor of plasma kallikrein and trypsin.

3) Peptides Having the "Scissile Bond" Replaced by a Pseudopeptide:

A third class of likely plasma kallikrein inhibitors are those in which some or all of the peptide bonds are replaced by non-peptide bonds. Groups that replace peptide bonds in compounds derived from peptides are usually referred to as pseudopeptides and designated with the symbol $\psi$. The most important peptide bond to replace is the one between the P1 and P1' residues, the so called "scissile bond". Thus, compounds of the formula 3 or 3a are likely to be specific plasma kallikrein inhibitors.

    Formula 3

    Formula 3a wherein:
→ the first residue may be 1, 2, 3, or 4, and the length of the compound is at least 5 residues and not more than 9; the -X$_4$=X$_5$- and -X$_6$=X$_7$- moieties being counted as two residues, X$_1$ corresponds to the P4 residue the inhibitor and may be picked from the set comprising {any d or l amino acid (having free or blocked amino group) or an amino group (possibly blocked with one of the groups acetyl, formyl, methyl, ethyl, propyl, isopropyl, n-butyl, secondary butyl, tertiary butyl, benzyl, or similar group)}; preferred choices are hydrogen, acetyl, glycine, and formyl, X$_2$ corresponds to the P3 residue and is most preferably 1-HIS; alternatives include (without limitation) L-C$^\delta$methylhistidine, L-C$^\epsilon$methylhistidine, L-p-aminophenylalanine, L-m-(N,Ndimethylamino)phenylalanine, canavanine (Merck Index 1745), and N-methylasparagine; all the alternatives have one or more of the properties: amphoteric, aromatic, hydrophobic, and cyclic, as does HIS, X$_3$ corresponds to the P2 residue and may be any 1 amino acid, preferably uncharged and hydrophobic; if X$_3$ is cysteine, the sulphur is blocked by one of a) a second cysteine residue, b) a thiol reagent, c) an alkyl group, if X$_3$ is not cysteine, then PRO is a preferred choice because the φ of CYS$_{14}$ is in the range accessible to PRO and the side group of PRO is not dissimilar to the disulfide group, other preferred alternatives at X$_3$ include 1-MET, 1-GLN, 1-pipecolic acid (Merck Index 7425), 1-2-azitidinecarboxylic acid (Merck Index 923), 1-LEU, 1-ILE, 1-VAL, cycloleucine (Merch Index 2740), 1-α-aminobutylric acid, 1-aminocyclopropane-1-carboxylic acid, and 1-methoxyalanine, X$_4$ corresponds to the P1 residue and is most preferably 1-LYS, 1-ARG, 1-ornithine, or 1-guanidolysine. (i.e. NH$_2$—CH(COOH)—(CH$_2$)$_4$—NH—C—(NH$_2$)$_2$+); 1-ALA, 1-SER, and GLY are preferred alternatives, = represents a suitable pseudopeptide that joins the side groups of X$_4$ and X$_5$ and allows the side groups to be in a relative orientation similar to that found for residues 15 and 16 of Kunitz domains; $\phi_4$ should be approximately −111°, $\psi_4$ should be approximately 36°, $\phi_5$ should be approximately −80°, $\psi_5$ should be approximately 164°, X$_5$ corresponds to the P1' residue and is most preferably ALA if X$_4$ is present; 1-PRO, GLY, and 1-SER are preferred alternatives; X$_5$ may be any amino acid if X$_1$-X$_4$ are absent, X$_6$ corresponds to the P2' residue and is most preferably 1-ASN, 1-SER, 1-GLN; other amino acids having small, neutral, hydrophilic groups, such as (but without limitation) O-methyl serine, α-amidoglycine, α-aminobutyric acid, β-fluoroalanine, N-methylasparagine, N,N-dimethylasparagine, and α-amino-γ-hydroxybutyric acid (homoserine), are preferred alternatives, = (if present) is a suitable pseudopeptide that allows the side groups of X$_6$ and X$_7$ to be in a suitable conformation, $\phi_6$ should be approximately −113°, $\psi_6$ should be approximately 85°, $\phi_7$ should be approximately −110°, $\psi_7$ should be approximately 123°, X$_7$ corresponds to the P3' residue and is most preferably HIS; preferred alternatives include, for example and without limitation, L-C$^\delta$methylhistidine, L-C$^\epsilon$methylhistidine, L-p-aminophenylalanine, L-m-(N,Ndimethylamino)phenylalanine, canavanine (Merck Index 1745), and N-methylasparagine; all the alternatives have one or more of the properties: amphoteric, aromatic, hydrophobic, and cyclic, as does HIS, X$_8$ corresponds to the P4' residue and most preferably is GLN; other neutral residues including, for example and without limitation, ASN, α-amino-δ-amidoadipic acid, HIS, and α-amino-ε-amidopimelic acid. The preferred alternative all have minimal size and no charged groups, and X$_9$ corresponds to the p5' residue and may be any l- or d-amino acid, preferably 1-ARG, 1-LEU, or 1-ALA (which occur frequently at this position of Kunitz Domains), or GLU, ASP, or other amino acids having acidic side groups (which might interact with plasma kallikrein in place of GLU$_{32}$ or GLU$_{31}$), or homoserine or other amino acid having a hydroxyl, or X$_9$ may be a free or blocked carboxyl group of X$_8$ or X$_9$ may be a free or blocked amide group of X$_8$; if X$_5$ is the first amino acid, then X$_9$ is present.

The compound VI shown in FIG. 5 can be incorporated in Fmoc synthesis of peptides to incorporate —X$_4$=GLY$_5$- of formulae 3.1 or 3.2. Other residue types can be introduced at residue 5. Compound VI leads to incorporation of ornithine=ALA which can be converted to ARG=ALA with N,N'-di-Cbz-S-methylisothiourea (TIAN92). If Cmpd I contained four methylene groups (instead of three), the following synthesis would lead to X$_4$=LYS. Compounds of the form of formula 3 in which X$_4$ is ornithine or guanidolysine are likely to be specific inhibitors of plasma kallikrein and should be tested. FIG. 5 shows intermediates involved in synthesis of VI. Compound I is ornithine aldehyde with the α amino group blocked with Fmoc and the δ amino group blocked with allyloxycarbonyl. The aldehyde can be made by selective reduction of the $N^\alpha$-Fmoc, $N^\delta$-Aloc blocked l-ornithine acid (MARC85 p. 397), by reduction of the $N^\alpha$-Fmoc, $N^\delta$-Aloc blocked l-ornithine acid chloride (MARC85 p. 396), reduction of the $N^\alpha$-Fmoc, $N^\delta$-Aloc blocked l-ornithine amide (MARC85 p. 398), or by oxidation of the primary alcohol obtained by reduction of the $N^\alpha$-Fmoc, $N^\delta$-Aloc blocked l-ornithine acid with $LiAlH_4$ (MARC85, p. 1099). Oxidation of the alcohol is carried out with N-bromosuccinamide (MARC85, p. 1057).

Cmpd II is converted to a Grignard reagent and reacted with I; the product is III. The free hydroxyl of III is blocked with THP (CARE90, p. 678) and the MEM group is removed to give Cmpd IV. Cmpd IV is oxidized to the carboxylic acid, cmpd V. Cmpd V is then dehydrated to give VI. The synthesis of VI does not guarantee a trans double bond. The synthesis of VI given does not lead to a stereospecific product. There are chyral centers at carbons 2 and 6. Cmpd VI could, in any event, be purified by chromatography over an optically active substrate.

Other peptide bonds may be replaced with pseudopeptide bonds.

An option in cmpds of formula 3 is to link the side group of $X_3$ to the pseudopeptide so as to lock part of the main chain into the correct comformation for binding.

4) Cyclic Peptides Having a Pseudopeptide at the "Scissile Bond"

A fourth class of likely plasma kallikrein inhibitors are those in which some or all of the peptide bonds are replaced by non-peptide bonds and the compound is cyclized. The first peptide bond to replace is the one between the P1 and P1' residues. Thus, compounds of formula 4 or 4a are likely to be specific inhibitors of plasma kallikrein.

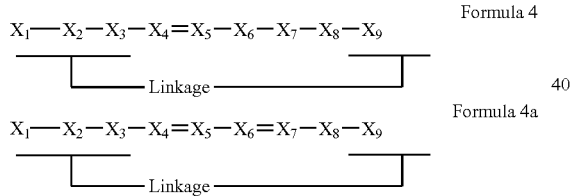

Formula 4

Formula 4a wherein:
→ the first residue may be 1, 2, 3, or 4, and the length of the compound is at least 5 residues and not more than 9; the -$X_4$=$X_5$- and -$X_6$=$X_7$- moieties being counted as two residues, $X_1$ corresponds to the P4 residue the inhibitor and may be picked from the set comprising {any d or lamino acid (having free or blocked amino group) or an amino group (possibly blocked with one of the groups acetyl, formyl, methyl, ethyl, propyl, isopropyl, n-butyl, secondary butyl, tertiary butyl, benzyl, or similar group)}; preferred choices are hydrogen, acetyl, glycine, and formyl, $X_2$ corresponds to the P3 residue and is most preferably l-HIS; alternatives include (without limitation) L-$C^\delta$methylhistidine, L-$C^\epsilon$methylhistidine, L-p-aminophenylalanine, L-m-(N,Ndimethylamino)phenylalanine, canavanine (Merck Index 1745), and N-methylasparagine; all the alternatives have one or more of the properties: amphoteric, aromatic, hydrophobic, and cyclic, as does HIS, $X_3$ corresponds to the P2 residue and may be any l amino acid, preferably uncharged and hydrophobic; if $X_3$ is cysteine, the sulphur is blocked by one of a) a second cysteine residue, b) a thiol reagent, c) an alkyl group, if $X_3$ is not cysteine, then PRO is a preferred choice because the φ of $CYS_{14}$ is in the range accessible to PRO and the side group of PRO is not dissimilar to the disulfide group, other preferred alternatives at $X_3$ include l-MET, l-GLN, l-pipecolic acid (Merck Index 7425), 1-2-azitidinecarboxylic acid (Merck Index 923), l-LEU, 1-ILE, 1-VAL, cycloleucine (Merch Index 2740), 1-α-aminobutylric acid, 1-aminocyclopropane-1-carboxylic acid, and 1-methoxyalanine, $X_4$ corresponds to the P1 residue and is most preferably l-LYS, l-ARG, 1-ornithine, or l-guanidolysine (i.e. $NH_2$—$CH(COOH)$—$(CH_2)_4$—$NH$—$C$—$(NH_2)_2$+); 1-ALA, 1-SER, and GLY are preferred alternatives, = represents a suitable pseudopeptide that joins the side groups of $X_4$ and $X_5$ and allows the side groups to be in a relative orientation similar to that found for residues 15 and 16 of Kunitz domains; $\phi_4$ should be approximately –111°, $\psi_4$ should be approximately 36°, $\psi_5$ should be approximately –80°, $\psi_5$ should be approximately 164°, $X_5$ corresponds to the P1' residue and is most preferably ALA if $X_4$ is present; 1-PRO, GLY, and 1-SER are preferred alternatives,; $X_5$ may be any amino acid if $X_1$-$X_4$ absent, $X_6$ corresponds to the P2' residue and is most preferably l-ASN, l-SER, l-GLN; other amino acids having small, neutral, hydrophilic groups, such as (but without limitation) O-methyl serine, α-amidoglycine, α-aminobutyric acid, β-fluoroalanine, N-methylasparagine, N,N-dimethylasparagine, and α-amino-γ-hydroxybutyric acid (homoserine), are preferred alternatives, = (if present) is a suitable pseudopeptide that allows the side groups of $X_6$ and $X_7$ to be in a suitable conformation, $\psi_6$ should be approximately –113°, $\psi_6$ should be approximately 85°, $\psi_7$ should be approximately –110°, $\psi_7$ should be approximately 123°, $X_7$ corresponds to the P3' residue and is most preferably HIS; preferred alternatives include, for example and without limitation, L-$C^\delta$methylhistidine, L-$C^\epsilon$methylhistidine, L-p-aminophenylalanine L-m-(N,Ndimethylamino)phenylalanine, canavanine (Merck Index 1745), and N-methylasparagine; all the alternatives have one or more of the properties: amphoteric, aromatic, hydrophobic, and cyclic, as does HIS, $X_8$ corresponds to the P4' residue and most preferably is GLN; other neutral residues including, for example and without limitation, ASN, α-amino-δ-amidoadipic acid, HIS, and α-amino-ε-amidopimelic acid. The preferred alternative all have minimal size and no charged groups, and $X_9$ corresponds to the p5' residue and may be any 1- or d-amino acid, preferably l-ARG, 1-LEU, or 1-ALA (which occur frequently at this position of Kunitz Domains), or GLU, ASP, or other amino acids having acidic side groups (which might interact with plasma kallikrein in place of $GLU_{32}$ or $GLU_{31}$), or homoserine or other amino acid having a hydroxyl, or $X_9$ may be a free or blocked carboxyl group of $X_8$ or $X_9$ may be a free or blocked amide group of $X_8$; if $X_5$ is the first amino acid, then $X_9$ is present, Linker may be a chain of carbon, nitrogen, oxygen, sulphur, phosphorus, or other multivalent atoms. In BPTI (Brookhaven Protein Data Bank entry 1TPA), $N_{13}$ is separated from $C_{19}$ by 14.6 Å. In alaphatic groups, carbon atoms are separated by about 1.54 Å and have bond angles of 109°; thus, an extended chain covers about 1.25 Å per $CH_2$ group. Accordingly, a chain of about 12 or more methylene groups would span the gap and allow the partially peptidyl chain to take up its preferred conformation. Linkers that contain hydrophilic groups, such as —OH, —NH$_2$, —COOH, —O—CH$_3$, may improve solubility. Linkers that contain aromatic groups (for example paraphenyl or 2,6 naphthylene) are allowed. An alternative is a peptidyl linker. Peptidyl linkers that are highly resistant to proteolysis are preferred. The gap of 14.5 Å could be bridged by five or six residues Thus, sequences such as GPTVG, GPTITG, GPETD, GPTGE, GTVTGG, DGPTTS or GPDFGS (SEQ ID NOs:55-61, respectively) would be appropriate. PRO is preferred because it is resistant to proteolysis. THR, VAL, and ILE are preferred because they favor extended structure. Charged amino acids (ASP, GLU, LYS, and ARG) are preferred because they improve solubility. GLY, SER, PRO, ASP, and ASN are preferred at the ends because they facilitate the needed turns. For plasma kallikrein binding, acidic groups near the start of the linker are preferred.

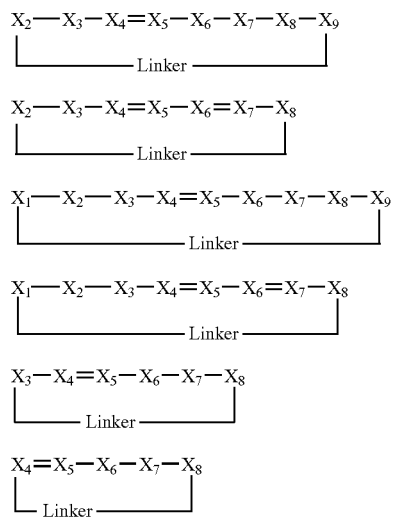

FIG. 9 shows compounds 4.1 and 4.2 according to formula 4. Compound 4.1 has a linker consisting of —(CH$_2$)$_{12}$—. Although the linker is purely hydrophobic, compound 4.1 contains residues X$_4$ (LYS or ARG), ARG$_6$, and X$_8$ (ARG or LYS) which are all positively charged. Furthermore, the nitrogen of PRO$_2$ is not an amide nitrogen, but a secondary or tertiary amine which would probably be protonated in acqueous solution. Compound 4.2 differs from compound 4.1 in that two hydroxyl groups have been incorporated into the linker to improve solubility.

An option in cmpds of formula 4 is to link the side group of X$_3$ to the pseudopeptide so as to lock part of the main chain into the correct comformation for binding.

5) Compounds Having at Least Three Side Groups on Non-Peptide Framework:

A fifth class of inhibitors contains the side groups corresponding to those (using Kunitz domain numbering) of X$_{15}$ (ARG or LYS), HIS$_{18}$, ASN$_{17}$, GLN$_{19}$, GLU$_{32}$, GLU$_{31}$, HIS$_{13}$, and X$_{34}$ (X=SER or THR) supported by a non-peptide framework that hold the α carbon at the correct position and causes the α-β bond to be directed in the correct direction. In addition, GLY$_{12}$ is included, as desired. Furthermore, electronegative atoms which are hydrogen-bond acceptors are positioned where some or all of the carbonyl oxygens are found in BPTI. In addition, hydrogen-bond donors are positioned where some or all of the amido nitrogen are found in BPTI. A minimum number of peptide bonds are included.

In a preferred embodiment, organic compounds (known to be synthesizable) are considered as possible frameworks. Compounds that are fairly rigid are preferred. Compounds not known to give rise to toxic break-down products are preferred. Compounds that are reasonably soluble are preferred, but we are attaching three basic side groups, so this preference is not strong.

The four side groups thought to comprise the pharmacophore are used to judge the suitability of each framework. For plasma kallikrein, the side groups X$_{15}$ (ARG, LYS, or other basic amino acid), HIS$_{18}$, ASN$_{17}$, GLN$_{19}$, GLU$_{32}$, GLU$_{31}$, HIS$_{13}$, and X$_{34}$ (X=SER or THR) in the above fromulae are taken as most important. The relative positions of these groups could be determined by X-ray diffraction or NMR. A model based on BPTI may also be used. Table 40 shows the coordinates of BPTI.

Wilson et al. (WIL93) describe an algorithm for designing an organic moiety to substitute or a large segment of a protein and to hold crucial residues in the appropriate conformation for binding. Compounds of the present invention can be designed using the same mathematical alogrithm. Where Wilson et al. identify bonds of the peptide backbone and seeks organic frameworks to hold remaining parts of the parental protein in place, we identify several bonds leading from the backbone to the side groups and replace the backbone with an organic or organometalic framework that holds only side groups or parts of side groups in place.

Mode of Production

The proteins of the present invention may be produced by any conventional technique, including
  (a) nonbiological synthesis by sequential coupling of component amino acids,
  (b) production by recombinant DNA techniques in a suitable host cell, and
  (c) removal of undesired sequences from LACI and coupling of synthetic replacement sequences The proteins disclosed herein are preferably produced, recombinantly, in a suitable host, such as bacteria from the genera *Bacillus, Escherichia, Salmonella, Erwinia*, and yeasts from the genera *Hansenula, Kluyveromyces, Pichia, Rhinosporidium, Saccharomyces*, and *Schizosaccharomyces*, or cultured mammalian cells such as COS-1. The more preferred hosts are microorganisms of the species *Pichia pastoris, Bacillus subtilis, Bacillus brevis, Saccharomyces cerevisiae, Escherichia coli* and *Yarrowia lipolytica*. Any promoter, regulatable or constitutive, which is functional in the host may be used to control gene expression.

Preferably the proteins are secreted. Most preferably, the proteins are obtained from conditioned medium. It is not required that the proteins described herein be secreted. Secretion is the preferred route because proteins are more likely to fold correctly, can be produced in conditioned medium with few contaminants, and are less likely to be toxic to host cells.

Unless there is a specific reason to include glycogroups, we prefer proteins designed to lack N-linked glycosylation sites so that they can be expressed in a wide variety of organisms including: 1) *E. coli*, 2) *B. subtilis*, 3) *P. pastoris*, 4) *S. cerevisiae*, and 5) mammalian cells.

Many cells used for engineered secretion of fusion proteins are less than optimal because they produce proteases that degrade the fusion protein. Several means exist for reducing this problem. There are strains of cells that are deficient in one or another of the offending proteases; Baneyx and Georgiou (BANE90) report that *E. coli* OmpT (an outer surface protease) degrades fusion proteins secreted from *E. coli*. They stated that an OmpT-strain is useful for production of fusion proteins and that degP- and ompT-mutations are additive. Baneyx and Georgiou (BANE91) report a third genetic locus (ptr) where mutation can improve the yield of engineered fusions.

Van Dijl et al. (1992) report cloning, expression, and function of *B. subtilis* signal peptidase (SPase) in *E. coli*. They found that overexpression of the spase gene lead to increased expression of a heterologous fusion protein. Use of strains having augmented secretion capabilities is preferred.

Anba et al. (1988) found that addition of PMSF to the culture medium greatly improved the yield of a fusion of phosphate binding protein (PhoS) to human growth hormone releasing factor (mhGRF).

Other factors that may affect production of these and other proteins disclosed herein include: 1) codon usage (it is preferred to optimize the codon usage for the host to. be used), signal sequence, 3) amino-acid sequence at intended processing sites, presence and localization of processing enzymes, deletion, mutation, or inhibition of various enzymes that might alter or degrade the engineered product and mutations that make the host more permissive in secretion (permissive secretion hosts are preferred).

Standard reference works setting forth the general principles of recombinant DNA technology include Watson, J. D. et al., *Molecular Biology of the Gene*, Volumes I and II, The Benjamin/Cummings Publishing Company, Inc., publisher, Menlo Park, Calif. (1987); Darnell, J. E. et al., *Molecular Cell Biology*, Scientific American Books, Inc., publisher, New York, N.Y. (1986); Lewin, B. M., *Genes II*, John Wiley & Sons, publishers, New York, N.Y. (1985); Old, R. W., et al., *Principles of Gene Manipulation: An Introduction to Genetic Engineering*, 2d edition, University of California Press, publisher, Berkeley, Calif. (1981); Sambrook, J. et al., *Molecular Cloning: A Laboratory Manual*, Cold Spring Harbor Laboratory, Cold Spring Harbor, N.Y. (1989); and Ausubel et al *Current Protocols in Molecular Biology*, Wiley Interscience, N.Y., (1987, 1992). These references are herein entirely incorporated by reference.

Preparation of Peptides

Chemical polypeptide synthesis is a rapidly evolving area in the art, and methods of solid phase polypeptide synthesis are well-described in the following references, hereby entirely incorporated by reference: (Merrifield, B., *J. Amer. Chem. Soc.* 85:2149-2154 (1963); Merrifield, B., *Science* 232:341-347 (1986); Wade, J. D. et al., *Biopolymers* 25:S21-S37 (1986); Fields, G. B., *Int. J. Polypeptide Prot. Res.* 35:161 (1990); MilliGen Report Nos. 2 and 2a, Millipore Corporation, Bedford, Mass., 1987) Ausubel et al, supra, and Sambrook et al, supra.

In general, as is known in the art, such methods involve blocking or protecting reactive functional groups, such as free amino, carboxyl and thio groups. After polypeptide bond formation, the protective groups are removed (or de-protected). Thus, the addition of each amino acid residue requires several reaction steps for protecting and deprotecting. Current methods utilize solid phase synthesis, wherein the C-terminal amino acid is covalently linked to an insoluble resin particle large enough to be separated from the fluid phase by filtration. Thus, reactants are removed by washing the resin particles with appropriate solvents using an automated programmed machine. The completed polypeptide chain is cleaved from the resin by a reaction which does not affect polypeptide bonds.

In the more classical method, known as the "tBoc method," the amino group of the amino acid being added to the resin-bound C-terminal amino acid is blocked with tert-butyloxycarbonyl chloride (tBoc). This protected amino acid is reacted with the bound amino acid in the presence of the condensing agent dicyclohexylcarbodiimide, allowing its carboxyl group to form a polypeptide bond the free amino group of the bound amino acid. The amino-blocking group is then removed by acidification with trifluoroacetic acid (TFA); it subsequently decomposes into gaseous carbon dioxide and isobutylene. These steps are repeated cyclically for each additional amino acid residue. A more vigorous treatment with hydrogen fluoride (HF) or trifluoromethanesulfonyl derivatives is common at the end of the synthesis to cleave the benzyl-derived side chain protecting groups and the polypeptide-resin bond.

More recently, the preferred "Fmoc" technique has been introduced as an alternative synthetic approach, offering milder reaction conditions, simpler activation procedures and compatibility with continuous flow techniques. This method was used, e.g., to prepare the peptide sequences disclosed in the present application. Here, the $\alpha$-amino group is protected by the base labile 9-fluorenylmethoxycarbonyl (Fmoc) group. The benzyl side chain protecting groups are replaced by the more acid labile t-butyl derivatives. Repetitive acid treatments are replaced by deprotection with mild base solutions, e.g., 20% piperidine in dimethylformamide (DMF), and the final HF cleavage treatment is eliminated. A TFA solution is used instead to cleave side chain protecting groups and the polypeptide resin linkage simultaneously.

At least three different polypeptide-resin linkage agents can be used: substituted benzyl alcohol derivatives that can be cleaved with 95% TFA to produce a polypeptide acid, methanolic ammonia to produce a polypeptide amide, or 1% TFA to produce a protected polypeptide which can then be used in fragment condensation procedures, as described by Atherton, E. et al., *J. Chem. Soc. Perkin Trans.* 1:538-546 (1981) and Sheppard, R. C. et al., *Int. J. Polypeptide Prot. Res.* 20:451-454 (1982). Furthermore, highly reactive Fmoc amino acids are available as pentafluorophenyl esters or dihydro-oxobenzotriazine esters derivatives, saving the step of activation used in the tBoc method.

Chemical Modification of Amino Acids

Covalent modifications of amino acids contained in proteins of interest are included within the scope of the present invention. Such modifications may be introduced into an epitopic peptide and/or alloantigenic peptide by reacting targeted amino acid residues of the polypeptide with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole-(alkyl)alanines, and D- or L-alkylainines where alkyl may be substituted or unsubstituted methyl, ethyl, propyl, hexyl, butyl, pentyl, iso-propyl, iso-butyl, sec-isotyl, iso-pentyl, non-acidic amino acids, of C1-C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (e.g., —SO$_3$H) threonine, serine, tyrosine.

Other substitutions may include unnatural hyroxylated amino acids may made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the proteins can be replaced by a ketomethylene moiety, e.g. (—C(=O)—CH$_2$—) for (—(C=O)—NH—). Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

In addition, any amino acid representing a component of the said proteins can be replaced by the same amino acid but of the opposite chirality. Thus, any amino acid naturally occurring in the L-configuration (which may also be referred to as the R or S configuration, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half lives, when administered by oral, intravenous, intramuscular, intraperitoneal, topical, rectal, intraocular, or other routes.

Additional amino acid modifications of amino acids of proteins of the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to a water-insoluble support matrix or to other macromolecular carriers, according to known method steps. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications of proteins of the present invention may include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W. H. Freeman & Co., San Francisco, pp. 79-86 (1983)), acetylation of the N-terminal amine, methylation of main chain amide residues (or substitution with N-methyl amino acids) and, in some instances, amidation of the C-terminal carboxyl groups, according to known method steps. Glycosylation is also possible.

Such derivatized moieties may improve the solubility, absorption, permeability across the blood brain barrier biological half life, and the like. Such moieties or modifications of proteins may alternatively eliminate or attenuate any possible undesirable side effect of the protein and the like. Moieties capable of mediating such effects are disclosed, for example, in *Remington's Pharmaceutical Sciences*, 16th ed., Mack Publishing Co., Easton, Pa. (1980).

Such chemical derivatives of proteins also may provide attachment to solid supports, including but not limited to, agarose, cellulose, hollow fibers, or other polymeric carbohydrates such as agarose, cellulose, such as for purification, generation of antibodies or cloning; or to provide altered physical properties, such as resistance to enzymatic degradation or increased antigenic properties, which is desired for therapeutic compositions comprising proteins of the present invention. Such peptide derivatives are well-known in the art, as well as method steps for making such derivatives using carbodiimides active esters of N-hydroxy succinimmide, or mixed anhydrides, as non-limiting examples.

Assays for Kallikrein Binding and Inhibition

The proteins may be assayed for kallikrein-binding activity by any conventional method. Scatchard (*Ann NY Acad Sci* (1949) 51:660-669) described a classical method of measuring and analyzing binding which has been applied to the binding of proteins. This method requires relatively pure protein and the ability to distinguish bound protein from unbound.

A second method appropriate for measuring the affinity of inhibitors for enzymes is to measure the ability of the inhibitor to slow the action of the enzyme. This method requires, depending on the speed at which the enzyme cleaves substrate and the availability of chromogenic or fluorogenic substrates, tens of micrograms to milligrams of relatively pure inhibitor.

A third method of determining the affinity of a protein for a second material is to have the protein displayed on a genetic package, such as M13, and measure the ability of the protein to adhere to the immobilized "second material". This method is highly sensitive because the genetic packages can be amplified. We obtain at least semiquantitative values for the binding constants by use of a pH step gradient. Inhibitors of known affinity for the immobilized protease are used to establish standard profiles against which other phage-displayed inhibitors are judged.

Preferably, the proteins of the present invention have a binding activity against plasma kallikrein such that the complex has a dissociation constant of at most 200 pM, more preferably at most 50 pM. Preferably, their inhibitory activity is sufficiently high so that the Ki of binding with plasma kallikrein is less than 500 pM, more preferably less than 50 pM.

Pharmaceutical Methods and Preparations

The preferred animal subject of the present invention is a mammal. By the term "mammal" is meant an individual belonging to the class Mammalia. The invention is particularly useful in the treatment of human subjects, although it is intended for veterinary uses as well.

The term "protection", as used herein, is intended to include "prevention," "suppression" and "treatment." "Prevention" involves administration of the protein prior to the induction of the disease. "Suppression" involves administration of the composition prior to the clinical appearance of the disease. "Treatment" involves administration of the protective composition after the appearance of the disease.

It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." It should also be understood that to be useful, the protection provided need not be absolute, provided that it is sufficient to carry clinical value. An agent which provides protection to a lesser degree than do competitive agents may still be of value if the other agents are ineffective for a particular individual, if it can be used in combination with other agents to enhance the level of protection, or if it is safer than competitive agents.

At least one of the proteins of the present invention may be administered, by any means that achieve their intended purpose, to protect a subject against a disease or other adverse condition. The form of administration may be systemic or topical. For example, administration of such a composition may be by various parenteral routes such as subcutaneous, intravenous, intradermal, intramuscular, intraperitoneal, intranasal, transdermal, or buccal routes. Alternatively, or concurrently, administration may be by the oral route. Parenteral administration can be by bolus injection or by gradual perfusion over time.

A typical regimen comprises administration of an effective amount of the protein, administered over a period ranging from a single dose, to dosing over a period of hours, days, weeks, months, or years.

It is understood that the suitable dosage of a protein of the present invention will be dependent upon the age, sex, health, and weight of the recipient, kind of concurrent treatment, if any, frequency of treatment, and the nature of the effect desired. However, the most preferred dosage can be tailored to the individual subject, as is understood and determinable by one of skill in the art, without undue experimentation. This will typically involve adjustment of a standard dose, e.g., reduction of the dose if the patient has a low body weight.

Prior to use in humans, a drug will first be evaluated for safety and efficacy in laboratory animals. In human clinical studies, one would begin with a dose expected to be safe in humans, based on the preclinical data for the drug in question, and on customary doses for analogous drugs (if any). If this dose is effective, the dosage may be decreased, to determine the minimum effective dose, if desired. If this dose is ineffective, it will be cautiously increased, with the patients monitored for signs of side effects. See, e.g., Berkow et al, eds., *The Merck Manual,* 15th edition, Merck and Co., Rahway, N.J., 1987; Goodman et al., eds., *Goodman and Gilman's The Pharmacological Basis of Therapeutics,* 8th edition, Pergamon Press, Inc., Elmsford, N.Y., (1990); *Avery's Drug Treatment: Principles and Practice of Clinical Pharmacology and Therapeutics,* 3rd edition, ADIS Press, LTD., Williams and Wilkins, Baltimore, Md. (1987), Ebadi, *Pharmacology,* Little, Brown and Co., Boston, (1985), which references and references cited therein, are entirely incorporated herein by reference.

The total dose required for each treatment may be administered by multiple doses or in a single dose. The protein may be administered alone or in conjunction with other therapeutics directed to the disease or directed to other symptoms thereof.

The appropriate dosage form will depend on the disease, the protein, and the mode of administration; possibilities include tablets, capsules, lozenges, dental pastes, suppositories, inhalants, solutions, ointments and parenteral depots. See, e.g., Berker, supra, Goodman, supra, Avery, supra and Ebadi, supra, which are entirely incorporated herein by reference, including all references cited therein.

In addition to at least one protein as described herein, a pharmaceutical composition may contain suitable pharmaceutically acceptable carriers, such as excipients, carriers and/or auxiliaries which facilitate processing of the active compounds into preparations which can be used pharmaceutically. See, e.g., Berker, supra, Goodman, supra, Avery, supra and Ebadi, supra, which are entirely incorporated herein by reference, included all references cited therein.

In Vitro Diagnostic Methods and Reagents

The in vitro assays of the present invention may be applied to any suitable analyte-containing sample, and may be qualitative or quantitative in nature. In order to detect the presence, or measure the amount, of an analyte, the assay must provide for a signal producing system (SPS) in which there is a detectable difference in the signal produced, depending on whether the analyte is present or absent (or, in a quantitative assay, on the amount of the analyte). The detectable signal may be one which is visually detectable, or one detectable only with instruments. Possible signals include production of colored or luminescent products, alteration of the characteristics (including amplitude or polarization) of absorption or emission of radiation by an assay component or product, and precipitation or agglutination of a component or product. The term "signal" is intended to include the discontinuance of an existing signal, or a change in the rate of change of an observable parameter, rather than a change in its absolute value. The signal may be monitored manually or automatically.

The component of the signal producing system which is most intimately associated with the diagnostic reagent is called the "label". A label may be, e.g., a radioisotope, a fluorophore, an enzyme, a co-enzyme, an enzyme substrate, an electron-dense compound, an agglutinable particle.

The radioactive isotope can be detected by such means as the use of a gamma counter or a scintillation counter or by autoradiography. Isotopes which are particularly useful for the purpose of the present invention are $^{3}$H, $^{125}$I, $^{131}$I, $^{35}$S, $^{14}$C, and, preferably, $^{125}$I.

It is also possible to label a compound with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

Alternatively, fluorescence-emitting metals such as $^{125}$Eu, or others of the lanthanide series, may be attached to the binding protein using such metal chelating groups as diethylenetriaminepentaacetic acid (DTPA) of ethylenediaminetetraacetic acid (EDTA).

The binding proteins also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isolumino, theromatic acridinium ester, imidazole, acridinium salt and oxalate ester.

Likewise, a bioluminescent compound may be used to label the binding protein. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Enzyme labels, such as horseradish peroxidase and alkaline phosphatase, are preferred. When an enzyme label is used, the signal producing system must also include a substrate for the enzyme. If the enzymatic reaction product is not itself detectable, the SPS will include one or more additional reactants so that a detectable product appears.

Assays may be divided into two basic types, heterogeneous and homogeneous. In heterogeneous assays, the interaction between the affinity molecule and the analyte does not affect the label, hence, to determine the amount or presence of analyte, bound label must be separated from free label. In homogeneous assays, the interaction does affect the activity of the label, and therefore analyte levels can be deduced without the need for a separation step.

In general, a kallikrein-binding protein (KBP) may be used diagnostically in the same way that an antikallikrein antibody is used. Thus, depending on the assay format, it may be used to assay Kallikrein, or by competitive inhibition, other substances which bind Kallikrein. The sample will normally be a biological fluid, such as blood, urine, lymph, semen, milk, or cerebrospinal fluid, or a fraction or derivative thereof, or a biological tissue, in the form of, e.g., a tissue section or homogenate. However, the sample conceivably could be (or derived from) a food or beverage, a pharmaceutical or diagnostic composition, soil, or surface or ground water. If a biological fluid or tissue, it may be taken from a human or other mammal, vertebrate or animal, or from a plant. The preferred sample is blood, or a fraction or derivative thereof.

In one embodiment, the kallikrein-binding protein is insolubilized by coupling it to a macromolecular support, and kallikrein in the sample is allowed to compete with a known quantity of a labeled or specifically labelable kallikrein analogue. The "kallikrein analogue" is a molecule capable of competing with kallikrein for binding to the KBP, and the term is intended to include kallikrein itself. It may be labeled already, or it may be labeled subsequently by specifically binding the label to a moiety differentiating the kallikrein analogue from kallikrein. The solid and liquid phases are separated, and the labeled kallikrein analogue in one phase is quantified. The higher the level of kallikrein analogue in the solid phase, i.e., sticking to the KBP, the lower the level of kallikrein analyte in the sample.

In a "sandwich assay", both an insolubilized kallikrein-binding protein, and a labeled kallikrein-binding protein are employed. The kallikrein analyte is captured by the insolubilized kallikrein-binding protein and is tagged by the labeled KBP, forming a tertiary complex. The reagents may be added to the sample in either order, or simultaneously. The kallikrein-binding proteins may be the same or different, and only one need be a KBP according to the present invention (the other may be, e.g., an antibody or a specific binding fragment thereof). The amount of labeled KBP in the tertiary complex is directly proportional to the amount of kallikrein analyte in the sample.

The two embodiments described above are both heterogeneous assays. However, homogeneous assays are conceivable. The key is that the label be affected by whether or not the complex is formed.

The kallikrein analyte may act as its own label if a kallikrein inhibitor is used as a diagnostic reagent.

A label may be conjugated, directly or indirectly (e.g., through a labeled anti-KBP antibody), covalently (e.g., with SPDP) or noncovalently, to the kallikrein-binding protein, to produce a diagnostic reagent. Similarly, the kallikrein binding protein may be conjugated to a solid-phase support to form a solid phase ("capture") diagnostic reagent. Suitable supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to its target. Thus the support configuration may be spherical, as in a bead, or cylindrical, as in the inside surface of a test tube, or the external surface of a rod. Alternatively, the surface may be flat such as a sheet, test strip, etc.

In Vivo Diagnostic Uses

Kunitz domains that bind very tightly to proteases that are causing pathology can be used for in vivo imaging. Diagnostic imaging of disease foci is considered one of the largest commercial opportunities for monoclonal antibodies. This opportunity has not, however, been achieved. Despite considerable effort and resources, to date only one monoclonal antibody-based imaging agent has received regulatory approval. The disappointing results obtained with monoclonal antibodies is due in large measure to:

i) Inadequate affinity and/or specificity;
ii) Poor penetration to target sites;
iii) Slow clearance from nontarget sites;
iv) Immunogenicity, most are mouse antibodies; and
v) High production cost and poor stability.

These limitations have led most in the diagnostic imaging field to begin to develop peptide-based imaging agents. While potentially solving the problems of poor penetration and slow clearance, peptide-based imaging agents are unlikely to possess adequate affinity, specificity and in vivo stability to be useful in most applications.

Engineered proteins are uniquely suited to the requirements for an imaging agent. In particular the extraordinary affinity and specificity that is obtainable by engineering small, stable, human-origin protein domains having known in vivo clearance rates and mechanisms combine to provide earlier, more reliable results, less toxicity/side effects, lower production and storage cost, and greater convenience of label preparation. Indeed, it should be possible to achieve the goal of realtime imaging with engineered protein imaging agents. Thus, a Kallikrein-binding protein, e.g., KKII/3#6 (SEQ ID NO:7), may be used for localizing sites of excessive pKA activity.

Radio-labelled binding protein may be administered to the human or animal subject. Administration is typically by injection, e.g., intravenous or arterial or other means of administration in a quantity sufficient to permit subsequent dynamic and/or static imaging using suitable radio-detecting devices. The preferred dosage is the smallest amount capable of providing a diagnostically effective image, and may be determined by means conventional in the art, using known radio-imaging agents as a guide.

Typically, the imaging is carried out on the whole body of the subject, or on that portion of the body or organ relevant to the condition or disease under study. The radio-labelled binding protein has accumulated. The amount of radio-labelled binding protein accumulated at a given point in time in relevant target organs can then be quantified.

A particularly suitable radio-detecting device is a scintillation camera, such as a gamma camera. A scintillation camera is a stationary device that can be used to image distribution of radio-labelled binding protein. The detection device in the camera senses the radioactive decay, the distribution of which can be recorded. Data produced by the imaging system can be digitized. The digitized information can be analyzed over time discontinuously or continuously. The digitized data can be processed to produce images, called frames, of the pattern of uptake of the radio-labelled binding protein in the target organ at a discrete point in time. In most continuous (dynamic) studies, quantitative data is obtained by observing changes in distributions of radioactive decay in target organs over time. In other words, a time-activity analysis of the data will illustrate uptake through clearance of the radio-labelled binding protein by the target organs with time.

Various factors should be taken into consideration in selecting an appropriate radioisotope. The radioisotope must be selected with a view to obtaining good quality resolution upon imaging, should be safe for diagnostic use in humans and animals, and should preferably have a short physical half-life so as to decrease the amount of radiation received by the body. The radioisotope used should preferably be pharmacologically inert, and, in the quantities administered, should not have any substantial physiological effect.

The binding protein may be radio-labelled with different isotopes of iodine, for example $^{123}$I, $^{125}$I, or 131I (see for example, U.S. Pat. No. 4,609,725). The extent of radio-labeling must, however be monitored, since it will affect the calculations made based on the imaging results (i.e. a diiodinated binding protein will result in twice the radiation count of a similar monoiodinated binding protein over the same time frame).

In applications to human subjects, it may be desirable to use radioisotopes other than $^{125}$I for labelling in order to decrease the total dosimetry exposure of the human body and to optimize the detectability of the labelled molecule (though this radioisotope can be used if circumstances require). Ready availability for clinical use is also a factor. Accordingly, for human applications, preferred radio-labels are for example, $^{99m}$Tc, $^{67}$Ga, $^{68}$Ga $^{90}$Y, $^{111}$In, $^{113m}$In, $^{123}$I, $^{186}$Re, $^{188}$Re or $^{211}$At.

The radio-labelled protein may be prepared by various methods. These include radio-halogenation by the chloramine—T method or the lactoperoxidase method and subsequent purification by HPLC (high pressure liquid chromatography), for example as described by J. Gutkowska et al in "Endocrinology and Metabolism Clinics of America: (1987) 16 (1):183. Other known method of radio-labelling can be used, such as IODOBEADS™.

There are a number of different methods of delivering the radio-labelled protein to the end-user. It may be administered by any means that enables the active agent to reach the agent's site of action in the body of a mammal. Because proteins are subject to bering digested when administered orally, parenteral administration, i.e., intravenous subcutaneous, intramuscular, would ordinarily be used to optimize absorption.

High-affinity, high-specificity inhibitors are also useful for in vitro diagnostics of excess human pKA activity.

Other Uses

The kallikrein-binding proteins of the present invention may also be used to purify kallikrein from a fluid, e.g., blood. For this purpose, the KBP is preferably immobilized on a solid-phase support. Such supports, include those already mentioned as useful in preparing solid phase diagnostic reagents.

Proteins, in general, can be used as molecular weight markers for reference in the separation or purification of proteins by electrophoresis or chromatography. In many instances, proteins may need to be denatured to serve as molecular weight markers. A second general utility for proteins is the use of hydrolyzed protein as a nutrient source. Hydrolyzed protein is commonly used as a growth media component for culturing microorganisms, as well as a food ingredient for human consumption. Enzymatic or acid hydrolysis is normally carried out either to completion, resulting in free amino acids, or partially, to generate both peptides and amino acids. However, unlike acid hydrolysis, enzymatic hydrolysis (proteolysis) does not remove non-amino acid functional groups that may be present. Proteins may also be used to increase the viscosity of a solution.

The proteins of the present invention may be used for any of the foregoing purposes, as well as for therapeutic and diagnostic purposes as discussed further earlier in this specification.

EXAMPLE 1

Construction of LACI (K1) Library

A synthetic oligonucleotide duplex having NsiI- and MluI-compatible ends was cloned into a parental vector (LACI:III) previously cleaved with the above two enzymes. The resultant ligated material was transfected by electroporation into XLIMR (F—) *Escherichia coli* strain and plated on Amp plates to obtain phage-generating $Ap^R$ colonies. The variegation scheme for Phase 1 focuses on the P1 region, and affected residues 13, 16, 17, 18 and 19. It allowed for $6.6 \times 10^5$ different DNA sequences ($3.1 \times 10^5$ different protein sequences). The library obtained consisted of $1.4 \times 10^6$ independent cfu's which is approximately a two fold representation of the whole library. The phage stock generated from this plating gave a total titer of $1.4 \times 10^{13}$ pfu's in about 3.9 ml, with each independent clone being represented, on average, $1 \times 10^7$ in total and $2.6 \times 10^6$ times per ml of phage stock.

To allow for variegation of residues 31, 32, 34 and 39 (phase II), synthetic oligonucleotide duplexes with MluI- and BstEII-compatible ends were cloned into previously cleaved $R_f$DNA derived from one of the following
i) the parental construction,
ii) the phase I library, or
iii) display phage selected from the first phase binding to a given target.

The variegation scheme for phase II allows for 4096 different DNA sequences (1600 different protein sequences) due to alterations at residues 31, 32, 34 and 39. The final phase II variegation is dependent upon the level of variegation remaining following the three rounds of binding and elution with a given target in phase I.

The combined possible variegation for both phases equals $2.7 \times 10^8$ different DNA sequences or $5.0 \times 10^7$ different protein sequences. When previously selected display phage are used as the origin of $R_f$DNA for the phase II variegation, the final level of variegation is probably in the range of $10^5$ to $10^6$.

EXAMPLE 2

Screening of LACI (K1) Library for Binding to Kallikrein

The overall scheme for selecting a LACI (K1) variant to bind to a given protease involves incubation of the phage-display library with the kallikrein-beads of interest in a buffered solution (PBS containing 1 mg/ml BSA) followed by washing away the unbound and poorly retained display-phage variant with PBS containing 0.1% Tween 20. Kallikrein beads were made by coupling human plasma Kallikrein (Calbiochem, San Diego, Calif., # 420302) to agarose beads using Reactigel (6×) (Pierce, Rockford, Ill., #202606). The more strongly bound display-phage are eluted with a low pH elution buffer, typically citrate buffer (pH 2.0) containing 1 mg/ml BSA, which is immediately neutralized with Tris buffer to pH 7.5. This process constitutes a single round of selection.

The neutralized eluted display-phage can be either used:
i) to inoculate an F⁺ strain of *E. coli* to generate a new display-phage stock, to be used for subsequent rounds of selection (so-called conventional screening), or
ii) be used directly for another immediate round of selection with the protease beads (so-called quick screening).

Typically, three rounds of either method, or a combination of the two, are performed to give rise to the final selected display-phage from which a representative number are sequenced and analyzed for binding properties either as pools of display-phage or as individual clones.

Two phases of selection were performed, each consisting of three rounds of binding and elution. Phase I selection used the phase I library (variegated residues 13, 16, 17, 18, and 19) which went through three rounds of binding and elution against a target protease giving rise to a subpopulation of clones. The $R_f$DNA derived from this selected subpopulation was used to generate the Phase II library (addition of variegated residues 31, 32, 34 and 39). The $1.8 \times 10^7$ independent transformants were obtained for each of the phase II libraries. The phase II libraries underwent three further rounds of binding and elution with the same target protease giving rise to the final selectants.

Following two phases of selection against human plasma kallikrein-agarose beads a number (10) of the final selection display-phage were sequenced. Table 6 shows the amino acids found at the variegated positions of LACI-K1 in the selected phage. Table 18 shows the complete sequences of the displayed proteins.

Table 23 shows that KkII/3(D) is a highly specific inhibitor of human Kallikrein. Phage that display the LACI-K1 derivative KkII/3(D) bind to Kallikrein beads at least 50-times more than it binds to other protease targets.

Preliminary measurements indicate that KKII/3#6 (SEQ ID NO:7) is a potent inhibitor of pKA with $K_i$ probably less than 500 pM.

All References, Including Those to U.S. and Foreign Patents or Patent Applications, and to Nonpatent Disclosures are Hereby Incorporated by Reference in Their Entirety.

TABLE 6

Amino acid sequences of LACI(K1) variants selected for binding to human plasma kallikrein.

| | | 13 | 16 | 17 | 18 | 19 | 31 | 32 | 34 | 39(a) |
|---|---|---|---|---|---|---|---|---|---|---|
| KKII/3#1 of | (SEQ ID NO: 2) | H | A | S | L | P | E | E | I | E |
| KKII/3#2 of | (SEQ ID NO: 3) | P | A | N | H | L | E | E | S | G |
| KKII/3#3 of | (SEQ ID NO: 4) | H | A | N | H | Q | E | E | T | G |
| KKII/3#4 of | (SEQ ID NO: 5) | H | A | N | H | Q | E | Q | T | A |
| KKII/3#5 of | (SEQ ID NO: 6) | H | A | S | L | P | E | E | I | G |
| KKII/3#6 of | (SEQ ID NO: 7) | H | A | N | H | Q | E | E | S | G |
| KKII/3#7 of | (SEQ ID NO: 8) | H | A | N | H | Q | E | E | S | G |
| KKII/3#8 of | (SEQ ID NO: 9) | H | A | N | H | Q | E | E | S | G |
| KKII/3#9 of | (SEQ ID NO: 10) | H | A | N | H | Q | E | E | S | G |
| KKII/3#10 of | (SEQ ID NO: 11) | H | G | A | H | L | E | E | I | E |
| Consensus | | H | A | N | H | Q | E | E | S/T | G |

(a)Amino acid numbers of variegated residues. LACI (K1) (residues 50–107 of SEQ ID NO: 25) is 58 amino acids long with the P1 position being residue number 15 and fixed as lysine in this instance. Whole sequences given in Table 18

TABLE 7

Kallikrein-binding display-phage chosen for further analysis.

| | 13 | 16 | 17 | 18 | 19 | 31 | 32 | 34 | 39 |
|---|---|---|---|---|---|---|---|---|---|
| KKII/3#6 (SEQ ID NO:7) | H | A | N | H | Q | E | E | S | G |
| KKII/3#5 (SEQ ID NO:6) | H | A | S | L | P | E | E | I | G |
| KKI/3 (b) (SEQ ID NO:13) | P | A | I | H | L | E | E | I | E |
| KKI/3 (a) (SEQ ID NO:12) | R | G | A | H | L | E | E | I | E |
| LACI (K1) (residues 50-107 of SEQ ID NO:25) | P | A | I | M | K | E | E | I | E* |
| BPTI (SEQ ID NO:1) | P | A | R | I | I | Q | T | V | R** |

(Note that clones a and b are from the first phase of screening and as such have a wild type sequence at residues 31 to 39.
*Parental molecule.
**Control (bovine pancreatic trypsin inhibitor.)
Whole sequences given in Table 18 and Table 17 (BPTI)

TABLE 8

Binding Data for Selected Kallikrein-binding Display-Phage.

| Display-Phage (a) | Fraction Bound (b) | Relative Binding (c) |
|---|---|---|
| LACI (residues 50-107 of SEQ ID NO:25) | $4.2 \times 10^{-6}$ | 1.0 |
| BPTI (SEQ ID NO:1) | $2.5 \times 10^{-6}$ | 6.0 |
| KKI/3 (a) (SEQ ID NO:12) | $3.2 \times 10^{-5}$ | 761 |
| KKI/3 (b) (SEQ ID NO:13) | $2.2 \times 10^{-3}$ | 524 |
| KKII/3#5 (SEQ ID NO:6) | $3.9 \times 10^{-3}$ | 928 |
| KKII/3#6 (SEQ ID NO:7) | $8.7 \times 10^{-3}$ | 2071 |

(a) Clonal isolates of display-phage. LACI(K1) is the parental molecule, BPTI (bovine pancreatic trypsin inhibitor) is a control and KKII/3 (5 and 6) and KKI/3 (a and b) were selected by binding to the target protease, kallikrein.
(b) The number of pfu's eluted after a binding experiment as a fraction of the input number ($10^{10}$ pfu's).
(c) Fraction bound relative to the parental display-phage, LACI(K1).

TABLE 17

Amino-acid sequence of BPTI

```
         1         2         3         4         5
12345678901234567890123456789012345678901234567890123456 78
RPDFCLEPPYTGPCKARIIRYFYNAKAGLCQTFVYGGCRAKRNNFKSAEDCMRTCGGA   (SEQ ID NO:1)
```

TABLE 18

Sequence of LACI-Ki and derivatives that bind human plasma kallikrein

```
         1         2         3         4         5
123456789012345678901234567890123456789012345678901234 5678
```

| | | |
|---|---|---|
| LACI-K1 | mhsfcafkaddgpckaimkrfffniftrqceefiyggcegnqnrfesleeckkmctrd | (residues 50-107 of SEQ ID NO:25) (SEQ ID NO: 62) |
| KKII/3#1 | mhsfcafkaddgHckASLPrfffniftrqcEEfIyggcEgnqnrfesleeckkmctrd | (SEQ ID NO:2) |
| KKII/3#2 | mhsfcafkaddgPckANHLrfffniftrqcEEfSyggcGgnqnrfesleeckkmctrd | (SEQ ID NO:3) |
| KKII/3#3 | mhsfcafkaddgHckANHQrfffniftrqcEEfTyggcGgnqnrfesleeckkmctrd | (SEQ ID NO:4) |

TABLE 18-continued

Sequence of LACI-Ki and derivatives that bind human plasma kallikrein

```
                        1         2         3         4         5
              1234567890123456789012345678901234567890123456789012345678

KKII/3#4      mhsfcafkaddgHckANHQrfffniftrqcEQfTyggcAgnqnrfesleeckkmctrd    (SEQ ID NO:5)
KKII/3#5      mhsfcafkaddgHckASLPrfffniftrqcEEfIyggcGgnqnrfesleeckkmctrd    (SEQ ID NO:6)
KKII/3#6      mhsfcafkaddgHckANHQrfffniftrqcEEfSyggcGgnqnrfesleeckkmctrd    (SEQ ID NO:7)
KKII/3#7      mhsfcafkaddgHckANHQrfffniftrqcEEfSyggcGgnqnrfesleeckkmctrd    (SEQ ID NO:8)
KKII/3#8      mhsfcafkaddgHckANHQrfffniftrqcEEfSyggcGgnqnrfesleeckkmctrd    (SEQ ID NO:9)
KKII/3#9      mhsfcafkaddgHckANHQrfffniftrqcEEfSyggcGgnqnrfesleeckkmctrd    (SEQ ID NO:10)
KKII/3#10     mhsfcafkaddgHckGAHLrfffniftrqcEEfIyggcEgnqnrfesleeckkmctrd    (SEQ ID NO:11)
KKII/3 (a)    mhsfcafkaddgRckGAHLrfffniftrqceefiyggcegnqnrfesleeckkmctrd    (SEQ ID NO:12)
KKII/3 (b)    mhsfcafkaddgPckAIHLrfffniftrqceefiyggcegnqnrfesleeckkmctrd    (SEQ ID NO:13)
KKII/3#C      mhsfcafkaddgHckANHQrfffniftrqcEEfSyggcGgnqnrfesleeckkmctrd    (SEQ ID NO:14)
```

TABLE 21

Variegation of LACI-K1

```
 a   b   1   2   3   4   5   6   7   8   9   10
 A   E   M   H   S   F   C   A   F   K   A   D
|gcc|gag|atg|cat|tcc|ttc|tgc|gcc|ttc|aag|gct|gat|
                    |NsiI|

I  N
                     C  H
                     F  Y
             F   S   L  S        L   S
             Y   C   W  P        W   P
             L   P   Q  R        Q   R
             H   R   R  T        M   T
             I   T   M  T

D   G   H   R   C   K   A   G   G   D   G   G   R
 11  12  13  14  15  16  17  18  19  20
|gat|ggt|cNt|tgt|aaa|gSt|NNt|NNS|NNg|cgt|

F   F   F   N   I   F   T   R   Q   C
 21  22  23  24  25  26  27  28  29  30
|ttc|ttc|ttc|aac|atc|ttc|acg|cgt|cag|tgc|
                        |MluI|

Q   E               N   H
    M   K               C   I
    F   S               F   Y
    Y   C               L   S
    L   P               W   P
    H   R               Q   R
    I   T               M   T
    N   V               K   V
    A   D               A   E
 E  Q   E   Q   F   G   W   Y   G   G   C   G   D   G   N   Q
 31 32  33  34  35  36  37  38  39  40  41  42
|Sag|Saa|ttc|NNS|tac|ggt|ggt|tgt|NNg|ggt|aac|cag|
                                    |BstEII|
```

TABLE 21-continued

Variegation of LACI-K1

```
 N   R   F   E   S   L   E   E
 43  44  45  46  47  48  49  50
|aac|cgg|ttc|gaa|tct|cta|gag|gaa|
         |BstBi|   |XbaI|
    |AgeI|

51  52  53  54  55  56  57  58  59  60
 C   K   K   M   C   T   R   D   G   A       (SEQ ID NO: 15)
|tgt|aag|aag|atg|tgc|act|cgt|gac|ggc|gcc|    (SEQ ID NO: 16)
                                |KasI|
```

The segment from NsiI to MluI gives 65,536 DNA sequences and 31,200 protein sequences. Second group of variegation gives 21,840 and 32,768 variants. This variegation can go in on a fragment having MluI and one of AgeI, BstBI, or XbaI ends. Because of the closeness between codon 42 and the 3' restriction site, one will make a self-priming oligonucleotide, fill in, and cut with MluI and, for example, BstBI. Total variants are $2.726 \times 10^9$ and $8.59 \times 10^9$.

TABLE 23

Specificity Results

| Display | Target | | | | Trypsin, two washes |
|---|---|---|---|---|---|
| | Plasmin | Thrombin | Kallikrein | Trypsin | |
| LACI-K1[1] | 1.0 | 1.0 | 1.0 | 1.0 | 1.0 |
| KkII/3(D)[2] | 3.4 | 1.5 | 196 | 2.0 | 1.4 |
| BPTI::III[3] | (88)[4] | (1.1) | (1.7) | (0.3) | (0.8) |

[1]Displayed on M13 III.
[2]Selected for plasma kallikrein binding.
[3]Control.
[4]BPTI relative to LACI.

numbers refer to relative binding of phage display clo4nes compared to the parental phage display.

The KkII/3(D)(Kallikrein) clone retains the parental molecule's affinity for trypsin.

TABLE 40

Coordinates of BPTI (1TPA)

| Atom | Res | # | X | Y | Z |
|---|---|---|---|---|---|
| N | ARG | 1 | 11.797 | 100.411 | 6.463 |
| CA | ARG | 1 | 12.697 | 101.495 | 6.888 |
| C | ARG | 1 | 13.529 | 101.329 | 8.169 |
| O | ARG | 1 | 14.755 | 101.605 | 8.115 |
| CB | ARG | 1 | 12.037 | 102.886 | 6.801 |
| CG | ARG | 1 | 13.107 | 103.969 | 6.578 |
| CD | ARG | 1 | 12.560 | 105.405 | 6.648 |
| NE | ARG | 1 | 13.682 | 106.329 | 6.443 |
| CZ | ARG | 1 | 13.570 | 107.597 | 6.106 |
| NH1 | ARG | 1 | 12.380 | 108.144 | 5.959 |
| NH2 | ARG | 1 | 14.657 | 108.320 | 5.922 |
| N | PRO | 2 | 12.931 | 101.060 | 9.332 |
| CA | PRO | 2 | 13.662 | 101.101 | 10.617 |
| C | PRO | 2 | 14.678 | 99.990 | 10.886 |
| O | PRO | 2 | 14.239 | 98.887 | 11.277 |
| CB | PRO | 2 | 12.604 | 100.958 | 11.726 |
| CG | PRO | 2 | 11.250 | 100.694 | 11.051 |
| CD | PRO | 2 | 11.489 | 100.823 | 9.539 |
| N | ASP | 3 | 15.885 | 100.463 | 11.149 |
| CA | ASP | 3 | 17.078 | 99.909 | 11.973 |
| C | ASP | 3 | 17.125 | 98.489 | 12.483 |
| O | ASP | 3 | 18.085 | 97.801 | 12.106 |
| CB | ASP | 3 | 17.819 | 100.822 | 12.981 |
| CG | ASP | 3 | 18.284 | 100.049 | 14.210 |
| OD1 | ASP | 3 | 17.667 | 100.236 | 15.287 |
| OD2 | ASP | 3 | 19.492 | 99.710 | 14.278 |
| N | PHE | 4 | 16.069 | 97.949 | 13.050 |
| CA | PHE | 4 | 15.939 | 96.466 | 13.148 |
| C | PHE | 4 | 15.865 | 95.753 | 11.765 |
| O | PHE | 4 | 16.126 | 94.534 | 11.580 |
| CB | PHE | 4 | 14.817 | 96.062 | 14.145 |
| CG | PHE | 4 | 13.386 | 96.292 | 13.636 |
| CD1 | PHE | 4 | 12.801 | 95.382 | 12.783 |
| CD2 | PHE | 4 | 12.735 | 97.447 | 13.940 |
| CE1 | PHE | 4 | 11.539 | 95.602 | 12.260 |
| CE2 | PHE | 4 | 11.482 | 97.684 | 13.408 |
| CZ | PHE | 4 | 10.879 | 96.748 | 12.582 |
| N | CYS | 5 | 15.456 | 96.498 | 10.755 |
| CA | CYS | 5 | 15.358 | 95.949 | 9.416 |
| C | CYS | 5 | 16.745 | 95.732 | 8.840 |
| O | CYS | 5 | 16.856 | 95.011 | 7.838 |
| CB | CYS | 5 | 14.653 | 96.970 | 8.534 |
| SG | CYS | 5 | 12.907 | 97.271 | 8.905 |
| N | LEU | 6 | 17.765 | 96.247 | 9.497 |
| CA | LEU | 6 | 19.110 | 96.026 | 9.002 |
| C | LEU | 6 | 19.777 | 94.885 | 9.731 |
| O | LEU | 6 | 20.896 | 94.493 | 9.322 |
| CB | LEU | 6 | 19.986 | 97.263 | 9.235 |
| CG | LEU | 6 | 19.438 | 98.493 | 8.493 |
| CD1 | LEU | 6 | 20.291 | 99.703 | 8.860 |
| CD2 | LEU | 6 | 19.261 | 98.356 | 6.971 |
| N | GLU | 7 | 19.122 | 94.342 | 10.725 |
| CA | GLU | 7 | 19.755 | 93.241 | 11.464 |
| C | GLU | 7 | 19.711 | 91.890 | 10.740 |
| O | GLU | 7 | 18.873 | 91.648 | 9.852 |
| CB | GLU | 7 | 19.232 | 93.163 | 12.914 |
| CG | GLU | 7 | 19.336 | 94.483 | 13.695 |
| CD | GLU | 7 | 18.778 | 94.225 | 15.092 |
| OE1 | GLU | 7 | 18.815 | 93.054 | 15.548 |
| OE2 | GLU | 7 | 17.924 | 95.019 | 15.561 |
| N | PRO | 8 | 20.765 | 91.108 | 10.862 |
| CA | PRO | 8 | 20.839 | 89.797 | 10.262 |
| C | PRO | 8 | 19.790 | 88.842 | 10.860 |
| O | PRO | 8 | 19.233 | 89.114 | 11.944 |
| CB | PRO | 8 | 22.244 | 89.267 | 10.608 |
| CG | PRO | 8 | 22.754 | 90.131 | 11.757 |
| CD | PRO | 8 | 21.882 | 91.377 | 11.769 |
| N | PRO | 9 | 19.319 | 87.911 | 10.080 |
| CA | PRO | 9 | 18.232 | 87.056 | 10.487 |
| C | PRO | 9 | 18.694 | 86.135 | 11.628 |
| O | PRO | 9 | 19.855 | 85.673 | 11.592 |
| CB | PRO | 9 | 17.905 | 86.208 | 9.266 |
| CG | PRO | 9 | 19.171 | 86.263 | 8.426 |
| CD | PRO | 9 | 19.774 | 87.618 | 8.743 |
| N | TYR | 10 | 17.829 | 85.920 | 12.619 |
| CA | TYR | 10 | 18.072 | 85.128 | 13.831 |
| C | TYR | 10 | 17.277 | 83.837 | 13.923 |
| O | TYR | 10 | 16.039 | 83.903 | 14.101 |
| CB | TYR | 10 | 17.700 | 86.057 | 15.008 |
| CG | TYR | 10 | 18.105 | 85.479 | 16.355 |
| CD1 | TYR | 10 | 17.163 | 85.154 | 17.302 |
| CD2 | TYR | 10 | 19.449 | 85.291 | 16.610 |
| CE1 | TYR | 10 | 17.586 | 84.599 | 18.519 |
| CE2 | TYR | 10 | 19.872 | 84.762 | 17.821 |
| CZ | TYR | 10 | 18.945 | 84.405 | 18.771 |
| OH | TYR | 10 | 19.413 | 83.745 | 19.968 |
| N | THR | 11 | 17.930 | 82.728 | 13.743 |
| CA | THR | 11 | 17.250 | 81.464 | 13.910 |
| C | THR | 11 | 16.905 | 81.173 | 15.365 |
| O | THR | 11 | 15.806 | 80.629 | 15.663 |
| CB | THR | 11 | 18.157 | 80.342 | 13.426 |
| OG1 | THR | 11 | 18.374 | 80.467 | 12.011 |
| CG2 | THR | 11 | 17.587 | 78.955 | 13.770 |
| N | GLY | 12 | 17.800 | 81.499 | 16.276 |
| CA | GLY | 12 | 17.530 | 81.172 | 17.717 |
| C | GLY | 12 | 17.795 | 79.707 | 18.130 |
| O | GLY | 12 | 18.093 | 78.812 | 17.294 |
| N | PRO | 13 | 17.594 | 79.422 | 19.438 |
| CA | PRO | 13 | 18.020 | 78.175 | 20.067 |
| C | PRO | 13 | 17.028 | 77.024 | 19.943 |
| O | PRO | 13 | 17.521 | 75.872 | 19.887 |
| CB | PRO | 13 | 18.118 | 78.476 | 21.544 |
| CG | PRO | 13 | 17.139 | 79.617 | 21.758 |
| CD | PRO | 13 | 17.023 | 89.360 | 20.414 |
| N | CYS | 14 | 15.735 | 77.328 | 19.666 |
| CA | CYS | 14 | 14.732 | 76.275 | 19.385 |
| C | CYS | 14 | 14.880 | 75.629 | 18.020 |
| O | CYS | 14 | 15.608 | 76.158 | 17.146 |
| CB | CYS | 14 | 13.299 | 76.717 | 19.613 |
| SG | CYS | 14 | 12.983 | 77.300 | 21.278 |
| N | LYS | 15 | 14.500 | 74.402 | 17.967 |
| CA | LYS | 15 | 14.776 | 73.485 | 16.889 |
| C | LYS | 15 | 13.544 | 73.079 | 16.047 |
| O | LYS | 15 | 13.540 | 71.988 | 15.436 |
| CB | LYS | 15 | 15.423 | 72.254 | 17.559 |
| CG | LYS | 15 | 16.816 | 72.596 | 18.149 |
| CD | LYS | 15 | 17.559 | 71.326 | 18.616 |
| CE | LYS | 15 | 18.900 | 71.636 | 19.321 |
| NZ | LYS | 15 | 19.518 | 70.412 | 19.904 |
| N | ALA | 16 | 12.618 | 73.966 | 15.829 |
| CA | ALA | 16 | 11.683 | 73.785 | 14.691 |
| C | ALA | 16 | 12.409 | 74.246 | 13.418 |
| O | ALA | 16 | 13.458 | 74.945 | 13.471 |
| CB | ALA | 16 | 10.368 | 74.627 | 14.903 |
| N | ARG | 17 | 11.872 | 73.853 | 12.310 |
| CA | ARG | 17 | 12.256 | 74.420 | 11.018 |
| C | ARG | 17 | 11.079 | 75.215 | 10.439 |
| O | ARG | 17 | 10.278 | 74.719 | 9.613 |
| CB | ARG | 17 | 12.733 | 73.245 | 10.174 |
| CG | ARG | 17 | 13.392 | 73.661 | 8.858 |
| CD | ARG | 17 | 12.294 | 74.044 | 7.852 |
| NE | ARG | 17 | 12.786 | 73.577 | 6.649 |
| CZ | ARG | 17 | 12.596 | 72.435 | 6.095 |
| NH1 | ARG | 17 | 11.637 | 71.610 | 6.379 |
| NH2 | ARG | 17 | 13.299 | 72.211 | 5.023 |
| N | ILE | 18 | 10.949 | 76.457 | 10.831 |
| CA | ILE | 18 | 9.848 | 77.334 | 10.377 |
| C | ILE | 18 | 10.312 | 78.435 | 9.443 |
| O | ILE | 18 | 11.321 | 79.098 | 9.777 |
| CB | ILE | 18 | 9.158 | 77.976 | 11.596 |
| CG1 | ILE | 18 | 8.479 | 76.864 | 12.430 |
| CG2 | ILE | 18 | 8.132 | 79.053 | 11.235 |
| CD1 | ILE | 18 | 8.302 | 77.409 | 13.857 |
| N | ILE | 19 | 9.724 | 78.469 | 8.238 |
| CA | ILE | 19 | 10.176 | 79.438 | 7.218 |
| C | ILE | 19 | 9.523 | 80.797 | 7.401 |
| O | ILE | 19 | 8.274 | 80.911 | 7.406 |
| CB | ILE | 19 | 10.074 | 78.910 | 5.754 |
| CG1 | ILE | 19 | 10.860 | 77.594 | 5.658 |
| CG2 | ILE | 19 | 10.525 | 79.981 | 4.702 |
| CD1 | ILE | 19 | 10.362 | 76.681 | 4.550 |
| N | ARG | 20 | 10.369 | 81.764 | 7.648 |
| CA | ARG | 20 | 9.967 | 83.160 | 7.870 |
| C | ARG | 20 | 10.707 | 84.063 | 6.893 |

TABLE 40-continued

Coordinates of BPTI (1TPA)

| | | | | | |
|---|---|---|---|---|---|
| O | ARG | 20 | 11.537 | 83.519 | 6.130 |
| CB | ARG | 20 | 10.349 | 83.584 | 9.300 |
| CG | ARG | 20 | 9.573 | 82.818 | 10.384 |
| CD | ARG | 20 | 8.086 | 83.272 | 10.386 |
| NE | ARG | 20 | 7.308 | 82.535 | 11.412 |
| CZ | ARG | 20 | 7.174 | 83.017 | 12.653 |
| NH1 | ARG | 20 | 7.772 | 84.156 | 13.006 |
| NH2 | ARG | 20 | 6.606 | 82.289 | 13.595 |
| N | TYR | 21 | 10.399 | 85.366 | 6.904 |
| CA | TYR | 21 | 10.990 | 86.415 | 6.062 |
| C | TYR | 21 | 11.783 | 87.398 | 6.869 |
| O | TYR | 21 | 11.415 | 87.709 | 8.041 |
| CB | TYR | 21 | 9.927 | 87.254 | 5.321 |
| CG | TYR | 21 | 9.227 | 86.344 | 4.286 |
| CD1 | TYR | 21 | 8.248 | 85.445 | 4.687 |
| CD2 | TYR | 21 | 9.646 | 86.387 | 2.959 |
| CE1 | TYR | 21 | 7.676 | 84.603 | 3.763 |
| CE2 | TYR | 21 | 9.069 | 85.549 | 2.012 |
| CZ | TYR | 21 | 8.078 | 84.673 | 2.405 |
| OH | TYR | 21 | 7.557 | 83.773 | 1.412 |
| N | PHE | 22 | 12.796 | 87.894 | 6.215 |
| CA | PHE | 22 | 13.615 | 88.967 | 6.804 |
| C | PHE | 22 | 13.987 | 89.932 | 5.698 |
| O | PHE | 22 | 14.116 | 89.477 | 4.531 |
| CB | PHE | 22 | 14.907 | 88.520 | 7.581 |
| CG | PHE | 22 | 16.075 | 88.032 | 6.669 |
| CD1 | PHE | 22 | 17.134 | 88.870 | 6.407 |
| CD2 | PHE | 22 | 15.985 | 86.820 | 6.026 |
| CE1 | PHE | 22 | 18.117 | 88.510 | 5.493 |
| CE2 | PHE | 22 | 16.971 | 86.465 | 5.087 |
| CZ | PHE | 22 | 18.026 | 87.309 | 4.827 |
| N | TYR | 23 | 14.114 | 91.168 | 6.073 |
| CA | TYR | 23 | 14.585 | 92.201 | 5.205 |
| C | TYR | 23 | 16.090 | 92.078 | 4.923 |
| O | TYR | 23 | 16.917 | 92.192 | 5.837 |
| CB | TYR | 23 | 14.153 | 93.589 | 5.740 |
| CG | TYR | 23 | 14.412 | 94.670 | 4.674 |
| CD1 | TYR | 23 | 15.332 | 95.661 | 4.931 |
| CD2 | TYR | 23 | 13.831 | 94.573 | 3.433 |
| CE1 | TYR | 23 | 15.673 | 96.561 | 3.951 |
| CE2 | TYR | 23 | 14.126 | 95.511 | 2.461 |
| CZ | TYR | 23 | 15.051 | 96.500 | 2.711 |
| OH | TYR | 23 | 15.328 | 97.524 | 1.731 |
| N | ASN | 24 | 16.465 | 91.884 | 3.687 |
| CA | ASN | 24 | 17.855 | 91.855 | 3.252 |
| C | ASN | 24 | 18.214 | 93.189 | 2.601 |
| O | ASN | 24 | 17.796 | 93.529 | 1.451 |
| CB | ASN | 24 | 18.069 | 90.729 | 2.240 |
| CG | ASN | 24 | 19.546 | 90.661 | 1.887 |
| OD1 | ASN | 24 | 20.363 | 91.402 | 2.468 |
| ND2 | ASN | 24 | 19.880 | 89.455 | 1.644 |
| N | ALA | 25 | 18.758 | 94.021 | 3.466 |
| CA | ALA | 25 | 19.115 | 95.402 | 3.073 |
| C | ALA | 25 | 20.153 | 95.346 | 1.943 |
| O | ALA | 25 | 20.214 | 96.277 | 1.110 |
| CB | ALA | 25 | 19.718 | 96.214 | 4.248 |
| N | LYS | 26 | 20.926 | 94.294 | 1.871 |
| CA | LYS | 26 | 21.927 | 94.209 | .795 |
| C | LYS | 26 | 21.316 | 93.971 | −.576 |
| O | LYS | 26 | 21.631 | 94.746 | −1.505 |
| CB | LYS | 26 | 23.192 | 93.345 | 1.081 |
| CG | LYS | 26 | 24.224 | 94.036 | 1.988 |
| CD | LYS | 26 | 25.450 | 93.125 | 2.200 |
| CE | LYS | 26 | 26.558 | 93.805 | 3.024 |
| NZ | LYS | 26 | 27.649 | 92.853 | 3.266 |
| N | ALA | 27 | 20.301 | 93.136 | −.638 |
| CA | ALA | 27 | 19.535 | 92.893 | −1.842 |
| C | ALA | 27 | 18.417 | 93.896 | −2.055 |
| O | ALA | 27 | 17.769 | 94.008 | −3.140 |
| CB | ALA | 27 | 18.965 | 91.498 | −1.663 |
| N | GLY | 28 | 18.108 | 94.574 | −1.014 |
| CA | GLY | 28 | 16.876 | 95.398 | −1.159 |
| C | GLY | 28 | 15.598 | 94.564 | −1.366 |
| O | GLY | 28 | 14.605 | 95.041 | −1.966 |
| N | LEU | 29 | 15.540 | 93.437 | −.697 |
| CA | LEU | 29 | 14.302 | 92.689 | −.621 |
| C | LEU | 29 | 14.113 | 91.764 | .573 |
| O | LEU | 29 | 15.091 | 91.447 | 1.290 |
| CB | LEU | 29 | 13.946 | 92.088 | −1.983 |
| CG | LEU | 29 | 14.560 | 90.736 | −2.317 |
| CD1 | LEU | 29 | 14.428 | 90.452 | −3.825 |
| CD2 | LEU | 29 | 15.947 | 90.475 | −1.753 |
| N | CYS | 30 | 12.929 | 91.251 | .701 |
| CA | CYS | 30 | 12.631 | 90.232 | 1.679 |
| C | CYS | 30 | 12.973 | 88.827 | 1.225 |
| O | CYS | 30 | 12.555 | 88.398 | .118 |
| CB | CYS | 30 | 11.200 | 90.387 | 2.252 |
| SG | CYS | 30 | 10.933 | 92.009 | 2.993 |
| N | GLN | 31 | 13.803 | 88.164 | 2.043 |
| CA | GLN | 31 | 14.137 | 86.787 | 1.847 |
| C | GLN | 31 | 13.585 | 85.869 | 2.933 |
| O | GLN | 31 | 13.386 | 86.287 | 4.096 |
| CB | GLN | 31 | 15.668 | 86.613 | 1.685 |
| CG | GLN | 31 | 16.217 | 87.696 | .795 |
| CD | GLN | 31 | 17.411 | 87.066 | .084 |
| OE1 | GLN | 31 | 18.580 | 87.572 | .152 |
| NE2 | GLN | 31 | 16.976 | 86.163 | −.802 |
| N | THR | 32 | 13.640 | 84.623 | 2.640 |
| CA | THR | 32 | 13.288 | 83.547 | 3.599 |
| C | THR | 32 | 14.502 | 83.008 | 4.376 |
| O | THR | 32 | 15.653 | 83.038 | 3.878 |
| CB | THR | 32 | 12.607 | 82.379 | 2.857 |
| OG1 | THR | 32 | 13.481 | 81.840 | 1.887 |
| CG2 | THR | 32 | 11.287 | 82.754 | 2.182 |
| N | PHE | 33 | 14.277 | 82.464 | 5.547 |
| CA | PHE | 33 | 15.348 | 81.924 | 6.396 |
| C | PHE | 33 | 14.664 | 80.984 | 7.337 |
| O | PHE | 33 | 13.406 | 81.039 | 7.354 |
| CB | PHE | 33 | 16.052 | 83.054 | 7.174 |
| CG | PHE | 33 | 15.292 | 83.602 | 8.392 |
| CD1 | PHE | 33 | 15.668 | 83.194 | 9.661 |
| CD2 | PHE | 33 | 14.299 | 84.545 | 8.255 |
| CE1 | PHE | 33 | 15.040 | 83.692 | 10.779 |
| CE2 | PHE | 33 | 13.664 | 85.064 | 9.397 |
| CZ | PHE | 33 | 14.036 | 84.631 | 10.661 |
| N | VAL | 34 | 15.421 | 80.121 | 8.005 |
| CA | VAL | 34 | 14.817 | 79.158 | 8.946 |
| C | VAL | 34 | 14.792 | 79.652 | 10.385 |
| O | VAL | 34 | 15.824 | 80.145 | 10.871 |
| CB | VAL | 34 | 15.603 | 77.860 | 8.945 |
| CG1 | VAL | 34 | 15.195 | 76.937 | 10.125 |
| CG2 | VAL | 34 | 15.430 | 77.129 | 7.611 |
| N | TYR | 35 | 13.618 | 79.811 | 10.941 |
| CA | TYR | 35 | 13.427 | 80.274 | 12.288 |
| C | TYR | 35 | 13.079 | 79.099 | 13.188 |
| O | TYR | 35 | 12.406 | 78.147 | 12.731 |
| CB | TYR | 35 | 12.330 | 81.337 | 12.313 |
| CG | TYR | 35 | 11.870 | 81.698 | 13.742 |
| CD1 | TYR | 35 | 12.758 | 82.213 | 14.672 |
| CD2 | TYR | 35 | 10.537 | 81.529 | 14.090 |
| CE1 | TYR | 35 | 12.316 | 82.567 | 15.958 |
| CE2 | TYR | 35 | 10.082 | 81.920 | 15.351 |
| CZ | TYR | 35 | 10.986 | 82.455 | 16.276 |
| OH | TYR | 35 | 10.533 | 82.900 | 17.569 |
| N | GLY | 36 | 13.843 | 78.988 | 14.257 |
| CA | GLY | 36 | 13.813 | 77.777 | 15.086 |
| C | GLY | 36 | 12.608 | 77.757 | 16.045 |
| O | GLY | 36 | 12.258 | 76.684 | 16.583 |
| N | GLY | 37 | 11.827 | 78.809 | 16.058 |
| CA | GLY | 37 | 10.533 | 78.722 | 16.717 |
| C | GLY | 37 | 10.571 | 79.339 | 18.109 |
| O | GLY | 37 | 9.500 | 79.680 | 18.662 |
| N | CYS | 38 | 11.653 | 79.933 | 18.487 |
| CA | CYS | 38 | 11.521 | 80.813 | 19.692 |
| C | CYS | 38 | 12.516 | 81.957 | 19.703 |
| O | CYS | 38 | 13.609 | 81.759 | 19.130 |
| CB | CYS | 38 | 11.705 | 80.016 | 21.020 |
| SG | CYS | 38 | 13.319 | 79.230 | 21.236 |
| N | ARG | 39 | 12.201 | 82.955 | 20.477 |
| CA | ARG | 39 | 13.042 | 84.091 | 20.782 |
| C | ARG | 39 | 13.345 | 84.908 | 19.525 |
| O | ARG | 39 | 14.479 | 85.415 | 19.364 |
| CB | ARG | 39 | 14.338 | 83.591 | 21.467 |
| CG | ARG | 39 | 14.123 | 83.002 | 22.885 |

TABLE 40-continued

Coordinates of BPTI (1TPA)

| | | | | | |
|---|---|---|---|---|---|
| CD | ARG | 39 | 15.509 | 82.671 | 23.502 |
| NE | ARG | 39 | 15.363 | 82.331 | 24.931 |
| CZ | ARG | 39 | 16.144 | 81.403 | 25.524 |
| NH1 | ARG | 39 | 17.181 | 80.838 | 24.899 |
| NH2 | ARG | 39 | 15.926 | 81.022 | 26.767 |
| N | ALA | 40 | 12.336 | 85.093 | 18.668 |
| CA | ALA | 40 | 12.469 | 85.896 | 17.438 |
| C | ALA | 40 | 13.003 | 87.295 | 17.694 |
| O | ALA | 40 | 12.459 | 87.974 | 18.591 |
| CB | ALA | 40 | 11.082 | 86.134 | 16.840 |
| N | LYS | 41 | 13.780 | 87.825 | 16.770 |
| CA | LYS | 41 | 14.069 | 89.246 | 16.766 |
| C | LYS | 41 | 13.050 | 89.929 | 15.884 |
| O | LYS | 41 | 12.110 | 89.279 | 15.385 |
| CB | LYS | 41 | 15.514 | 89.487 | 16.297 |
| CG | LYS | 41 | 16.414 | 88.775 | 17.308 |
| CD | LYS | 41 | 17.893 | 89.161 | 17.266 |
| CE | LYS | 41 | 18.524 | 88.784 | 18.640 |
| NZ | LYS | 41 | 19.977 | 88.978 | 18.595 |
| N | ARG | 42 | 13.185 | 91.205 | 15.759 |
| CA | ARG | 42 | 12.207 | 91.986 | 14.989 |
| C | ARG | 42 | 12.282 | 91.935 | 13.459 |
| O | ARG | 42 | 11.214 | 91.904 | 12.783 |
| CB | ARG | 42 | 12.066 | 93.440 | 15.465 |
| CG | ARG | 42 | 11.365 | 93.469 | 16.839 |
| CD | ARG | 42 | 11.248 | 94.923 | 17.264 |
| NE | ARG | 42 | 12.630 | 95.393 | 17.419 |
| CZ | ARG | 42 | 13.034 | 96.670 | 17.567 |
| NH1 | ARG | 42 | 12.191 | 97.681 | 17.582 |
| NH2 | ARG | 42 | 14.344 | 96.964 | 17.686 |
| N | ASN | 43 | 13.432 | 91.638 | 12.944 |
| CA | ASN | 43 | 13.534 | 91.297 | 11.513 |
| C | ASN | 43 | 13.074 | 89.873 | 11.164 |
| O | ASN | 43 | 13.896 | 88.965 | 10.939 |
| CB | ASN | 43 | 14.973 | 91.612 | 11.028 |
| CG | ASN | 43 | 14.962 | 91.773 | 9.511 |
| OD1 | ASN | 43 | 13.867 | 91.977 | 8.926 |
| ND2 | ASN | 43 | 16.144 | 91.851 | 8.961 |
| N | ASN | 44 | 11.803 | 89.578 | 11.367 |
| CA | ASN | 44 | 11.254 | 88.237 | 11.328 |
| C | ASN | 44 | 9.754 | 88.326 | 11.025 |
| O | ASN | 44 | 8.985 | 88.836 | 11.875 |
| CB | ASN | 44 | 11.592 | 87.487 | 12.662 |
| CG | ASN | 44 | 10.995 | 86.079 | 12.769 |
| OD1 | ASN | 44 | 9.967 | 85.727 | 12.165 |
| ND2 | ASN | 44 | 11.677 | 85.165 | 13.350 |
| N | PHE | 45 | 9.338 | 88.074 | 9.788 |
| CA | PHE | 45 | 7.939 | 88.332 | 9.277 |
| C | PHE | 45 | 7.255 | 87.073 | 8.777 |
| O | PHE | 45 | 7.934 | 86.052 | 8.515 |
| CB | PHE | 45 | 7.943 | 89.381 | 8.158 |
| CG | PHE | 45 | 8.609 | 90.681 | 8.657 |
| CD1 | PHE | 45 | 9.962 | 90.922 | 8.445 |
| CD2 | PHE | 45 | 7.851 | 91.618 | 9.326 |
| CE1 | PHE | 45 | 10.538 | 92.109 | 8.899 |
| CE2 | PHE | 45 | 8.433 | 92.808 | 9.759 |
| CZ | PHE | 45 | 9.773 | 93.056 | 9.544 |
| N | LYS | 46 | 5.953 | 87.013 | 8.850 |
| CA | LYS | 46 | 5.307 | 85.750 | 8.528 |
| C | LYS | 46 | 4.957 | 85.669 | 7.063 |
| O | LYS | 46 | 4.816 | 84.538 | 6.573 |
| CB | LYS | 46 | 4.008 | 85.607 | 9.317 |
| CG | LYS | 46 | 4.338 | 84.938 | 10.654 |
| CD | LYS | 46 | 3.144 | 85.117 | 11.573 |
| CE | LYS | 46 | 3.348 | 84.392 | 12.912 |
| NZ | LYS | 46 | 2.160 | 84.624 | 13.772 |
| N | SER | 47 | 5.091 | 86.774 | 6.384 |
| CA | SER | 47 | 4.904 | 86.776 | 4.924 |
| C | SER | 47 | 5.754 | 87.843 | 4.273 |
| O | SER | 47 | 6.210 | 88.797 | 4.983 |
| CB | SER | 47 | 3.418 | 87.035 | 4.542 |
| OG | SER | 47 | 3.126 | 88.431 | 4.812 |
| N | ALA | 48 | 6.000 | 87.652 | 2.979 |
| CA | ALA | 48 | 6.785 | 88.690 | 2.344 |
| C | ALA | 48 | 6.089 | 90.062 | 2.370 |
| O | ALA | 48 | 6.728 | 91.153 | 2.416 |
| CB | ALA | 48 | 7.020 | 88.246 | .910 |
| N | GLU | 49 | 4.760 | 90.049 | 2.411 |
| CA | GLU | 49 | 4.004 | 91.319 | 2.332 |
| C | GLU | 49 | 4.141 | 92.115 | 3.621 |
| O | GLU | 49 | 4.288 | 93.368 | 3.569 |
| CB | GLU | 49 | 2.477 | 91.014 | 2.129 |
| CG | CLU | 49 | 2.093 | 90.462 | .742 |
| CD | GLU | 49 | 2.593 | 89.033 | .538 |
| OE1 | GLU | 49 | 2.701 | 88.254 | 1.524 |
| OE2 | GLU | 49 | 2.618 | 88.541 | -.630 |
| N | ASP | 50 | 4.098 | 91.367 | 4.747 |
| CA | ASP | 50 | 4.316 | 92.036 | 6.061 |
| C | ASP | 50 | 5.694 | 92.642 | 6.098 |
| O | ASP | 50 | 5.807 | 93.832 | 6.441 |
| CB | ASP | 50 | 4.244 | 91.148 | 7.311 |
| CG | ASP | 50 | 2.836 | 90.713 | 7.693 |
| OD1 | ASP | 50 | 1.831 | 91.183 | 7.108 |
| OD2 | ASP | 50 | 2.725 | 89.630 | 8.316 |
| N | CYS | 51 | 6.660 | 91.834 | 5.675 |
| CA | CYS | 51 | 8.069 | 92.253 | 5.611 |
| C | CYS | 51 | 8.278 | 93.500 | 4.739 |
| O | CYS | 51 | 8.797 | 94.541 | 5.243 |
| CB | CYS | 51 | 8.955 | 91.080 | 5.141 |
| SG | CYS | 51 | 10.694 | 91.506 | 4.989 |
| N | MET | 52 | 7.678 | 93.467 | 3.554 |
| CA | MET | 52 | 7.777 | 94.629 | 2.704 |
| C | MET | 52 | 7.113 | 95.861 | 3.268 |
| O | MET | 52 | 7.730 | 96.945 | 3.202 |
| CB | MET | 52 | 7.489 | 94.389 | 1.189 |
| CG | MET | 52 | 8.547 | 95.004 | .261 |
| SD | MET | 52 | 9.677 | 93.778 | -.404 |
| CE | MET | 52 | 8.424 | 92.566 | -.868 |
| N | ARG | 53 | 5.939 | 95.729 | 3.847 |
| CA | ARG | 53 | 5.276 | 96.896 | 4.444 |
| C | ARG | 53 | 6.066 | 97.454 | 5.604 |
| O | ARG | 53 | 6.260 | 98.691 | 5.654 |
| CB | ARG | 53 | 3.886 | 96.462 | 4.982 |
| CG | ARG | 53 | 2.861 | 97.572 | 5.264 |
| CD | ARG | 53 | 1.424 | 97.032 | 5.029 |
| NE | ARG | 53 | 1.279 | 95.906 | 5.894 |
| CZ | ARG | 53 | 1.027 | 94.612 | 5.694 |
| NH1 | ARG | 53 | .686 | 94.084 | 4.520 |
| NH2 | ARG | 53 | 1.167 | 93.823 | 6.747 |
| N | THR | 54 | 6.627 | 96.618 | 6.444 |
| CA | THR | 54 | 7.462 | 97.165 | 7.516 |
| C | THR | 54 | 8.830 | 97.720 | 7.119 |
| O | THR | 54 | 9.266 | 98.747 | 7.690 |
| CB | THR | 54 | 7.674 | 96.154 | 8.624 |
| OG1 | THR | 54 | 6.377 | 95.698 | 8.972 |
| CG2 | THR | 54 | 8.395 | 96.794 | 9.843 |
| N | CYS | 55 | 9.580 | 96.927 | 6.394 |
| CA | CYS | 55 | 10.971 | 97.234 | 6.147 |
| C | CYS | 55 | 11.291 | 97.818 | 4.797 |
| O | CYS | 55 | 12.436 | 98.320 | 4.690 |
| CB | CYS | 55 | 11.850 | 96.040 | 6.455 |
| SG | CYS | 55 | 11.943 | 95.674 | 8.255 |
| N | GLY | 56 | 10.514 | 97.479 | 3.790 |
| CA | GLY | 56 | 10.957 | 97.710 | 2.392 |
| C | GLY | 56 | 11.228 | 99.190 | 2.152 |
| O | GLY | 56 | 10.367 | 100.002 | 2.539 |
| N | GLY | 57 | 12.461 | 99.566 | 1.946 |
| CA | GLY | 57 | 12.800 | 100.986 | 2.017 |
| C | GLY | 57 | 13.886 | 101.219 | 3.058 |
| O | GLY | 57 | 14.039 | 102.363 | 3.552 |
| N | ALA | 58 | 14.615 | 100.141 | 3.414 |
| CA | ALA | 58 | 15.722 | 100.266 | 4.422 |
| C | ALA | 58 | 17.104 | 99.977 | 3.828 |
| O | ALA | 58 | 18.036 | 100.786 | 4.093 |
| CB | ALA | 58 | 15.483 | 99.453 | 5.728 |
| OXT | ALA | 58 | 17.207 | 99.280 | 2.788 |

TABLE 50

Places in BPTI where disulfides are plausible
Limit on Ca–Ca is 9.0, on Cb–Cb is 6.5 Limit on Ca–Cb is 7.5

| Res#1 | | Res#2 | | A–A | A1–B2 | A2–B1 | B–B |
|---|---|---|---|---|---|---|---|
| ARG | 1 | GLY | 57 | 4.90 | 4.71 | 5.20 | 4.62 |
| PRO | 2 | CYS | 5 | 5.56 | 4.73 | 6.17 | 5.50 |
| PHE | 4 | ARG | 42 | 6.11 | 5.43 | 4.91 | 4.02 |
| PHE | 4 | ASN | 43 | 5.93 | 5.38 | 5.59 | 5.44 |
| CYS | 5 | TYR | 23 | 5.69 | 4.53 | 5.82 | 4.41 |
| CYS | 5 | CYS | 55 | 5.62 | 4.59 | 4.40 | 3.61 |
| CYS | 5 | ALA | 58 | 6.61 | 5.09 | 5.38 | 3.84 |
| LEU | 6 | ALA | 25 | 5.96 | 4.80 | 6.50 | 5.10 |
| LEU | 6 | ALA | 58 | 7.10 | 5.97 | 7.10 | 6.11 |
| GLU | 7 | ASN | 43 | 6.52 | 5.07 | 6.16 | 4.91 |
| PRO | 9 | PHE | 22 | 6.21 | 4.65 | 5.66 | 4.14 |
| PRO | 9 | PHE | 33 | 7.17 | 5.63 | 5.76 | 4.21 |
| PRO | 9 | ASN | 43 | 6.41 | 5.63 | 7.07 | 6.40 |
| TYR | 10 | LYS | 41 | 6.45 | 5.62 | 5.14 | 4.27 |
| THR | 11 | VAL | 34 | 5.99 | 6.35 | 5.71 | 5.72 |
| THR | 11 | GLY | 36 | 5.18 | 4.80 | 5.31 | 4.75 |
| GLY | 12 | CYS | 14 | 5.88 | 6.43 | 5.56 | 5.75 |
| GLY | 12 | GLY | 36 | 5.68 | 4.66 | 5.29 | 4.55 |
| GLY | 12 | CYS | 38 | 6.34 | 6.80 | 4.90 | 5.49 |
| GLY | 12 | ARG | 39 | 6.17 | 5.49 | 4.83 | 4.35 |
| CYS | 14 | ALA | 16 | 6.13 | 6.47 | 5.95 | 5.93 |
| CYS | 14 | GLY | 36 | 4.65 | 3.79 | 4.68 | 4.25 |
| CYS | 14 | GLY | 37 | 5.54 | 5.42 | 4.48 | 4.32 |
| CYS | 14 | CYS | 38 | 5.57 | 5.08 | 4.47 | 3.92 |
| ALA | 16 | ILE | 18 | 5.88 | 5.79 | 5.30 | 4.86 |
| ALA | 16 | GLY | 37 | 5.46 | 4.38 | 4.48 | 3.27 |
| ARG | 17 | VAL | 34 | 5.77 | 5.23 | 6.39 | 5.57 |
| ILE | 18 | ARG | 20 | 6.34 | 6.36 | 6.44 | 6.18 |
| ILE | 18 | TYR | 35 | 5.01 | 5.09 | 4.90 | 4.68 |
| ILE | 18 | GLY | 37 | 6.53 | 6.42 | 5.35 | 5.33 |
| ILE | 19 | THR | 32 | 6.30 | 5.79 | 6.04 | 5.18 |
| ARG | 20 | TYR | 35 | 6.31 | 5.35 | 5.42 | 4.25 |
| ARG | 20 | ASN | 44 | 6.28 | 6.66 | 5.16 | 5.30 |
| TYR | 21 | CYS | 30 | 6.04 | 5.51 | 5.43 | 4.57 |
| TYR | 21 | PHE | 45 | 4.83 | 4.74 | 4.56 | 4.06 |
| TYR | 21 | ALA | 48 | 6.06 | 6.76 | 4.56 | 5.38 |
| TYR | 21 | CYS | 51 | 6.54 | 5.17 | 5.34 | 3.95 |
| PHE | 22 | PHE | 33 | 7.26 | 6.41 | 6.72 | 5.60 |
| PHE | 22 | ASN | 43 | 5.25 | 5.17 | 5.01 | 4.63 |
| TYR | 23 | ASN | 43 | 6.46 | 5.87 | 6.24 | 5.70 |
| TYR | 23 | CYS | 51 | 6.53 | 5.74 | 6.23 | 5.80 |
| TYR | 23 | CYS | 55 | 6.27 | 4.88 | 4.86 | 3.44 |
| TYR | 23 | ALA | 58 | 8.18 | 7.33 | 6.98 | 6.01 |
| ASN | 24 | ALA | 27 | 5.46 | 5.05 | 4.85 | 4.08 |
| ASN | 24 | GLN | 31 | 6.44 | 5.89 | 5.58 | 4.80 |
| ALA | 25 | ALA | 58 | 6.08 | 6.05 | 5.69 | 5.53 |
| ALA | 27 | LEU | 29 | 5.38 | 5.65 | 4.92 | 5.06 |
| CYS | 30 | ALA | 48 | 6.08 | 6.00 | 4.73 | 4.88 |
| CYS | 30 | CYS | 51 | 6.35 | 5.12 | 4.96 | 3.72 |
| CYS | 30 | MET | 52 | 6.63 | 6.63 | 5.47 | 5.56 |
| TYR | 35 | ASN | 44 | 8.31 | 7.45 | 7.05 | 6.20 |
| ALA | 40 | ASN | 44 | 6.65 | 5.11 | 5.90 | 4.42 |
| LYS | 41 | ASN | 44 | 6.21 | 5.11 | 6.66 | 5.71 |
| PHE | 45 | ASP | 50 | 6.10 | 5.04 | 4.96 | 4.19 |
| PHE | 45 | CYS | 51 | 5.37 | 5.07 | 3.84 | 3.61 |
| LYS | 46 | ASP | 50 | 6.83 | 5.63 | 7.21 | 5.90 |
| SER | 47 | GLU | 49 | 5.31 | 5.63 | 4.86 | 4.75 |
| SER | 47 | ASP | 50 | 5.41 | 5.02 | 5.30 | 5.03 |
| MET | 52 | GLY | 56 | 4.44 | 3.58 | 4.95 | 3.71 |
| CYS | 55 | ALA | 58 | 5.89 | 5.05 | 6.08 | 5.04 |

TABLE 55

Shortened Kunitz domains to bind plasma kallikrein

```
         1111111111222222222233333333334444444444555555555
1234567890123456789012345678901234567890123456789012345678
RPDFCLEPPYTGPCKARIIRYFYNAKAGLCQTFVYGGCRAKRNNFKSAEDCMRTCGGA    BPTI (SEQ ID NO: 1)

MHSFCAFKADDGPCKAIMKRFFFNIFTRQCEEFIYGGCEGNQNRFESLEECKKMCTRD    LACK-K1 (residues 50–107
                                                              of SEQ ID NO: 25)
```

ShpKa #1: Plasma Kallikrein binder from shortened BPTI
```
  111111112222222222333333333
  345678901234567890123456789
  HCKANHQRCFYNAKAGLCEEFSYGGCG      (SEQ ID NO: 17)
```

ShpKa#2: Plasma Kallikrein binder from shortened BPTI
```
  1111111122222222223333333333444444444555
  3456789012345678901234567890123456789012
  HCKANHQRYFYNAKAGLCEEFTYGGCGAKRNNFKSAEDCM    (SEQ ID NO: 18)
```

ShpKa#3: Plasma Kallikrein binder from shortened BPTI
```
  1111111122222222223333333333444444444555
  3456789012345678901234567890123456789012
  HCRANHQCYFYNAKAGLCEEFSCGGCGAKRNNFKSAEDCM    (SEQ ID NO: 19)
```

ShpKa#4: Plasma Kallikrein binder from shortened LACI-K1
```
  111111112222222222333333333
  345678901234567890123456789
  HCKANHQRCFFNIFTRQCEEFSYGGCG
```
(SEQ ID NO: 20)

Convert $F_{21}$ to CYS to allow disulfide to $C_{30}$.

TABLE 55-continued

Shortened Kunitz domains to bind plasma kallikrein

ShpKa#5: Plasma Kallikrein binder from shortened LACI-K1 #2
```
          1111111222222222233333333333
          34567890123456789012345 6789
          HCKANHQRCFFNG-TRQCEEFSYGGCG
```
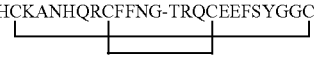

Shorten the loop between 21 and 30.    (SEQ ID NO: 21)

ShpKa#6: Plasma Kallikrein binder from shortened LACI-K1 #3
```
          1111111222222222233333333333
          34567890123456789012345 6789
          HCKANHQCFFNIFTRQCEEFSCGGCG
```
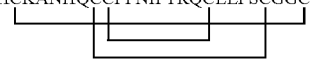

(SEQ ID NO: 22)

R20C and Y35C to allow third disulfide.

ShpKa#7: Plasma Kallikrein binder from shortened LACI0K1 #4
```
          1111111222222222233333333333
          34567890123456789012345 6789
          HCKANHQCFFNPDARQ2CEEFSCGGCG
```

(SEQ ID NO: 23)

Change 24–27 to DVTE (subseq. found in several KuDoms) to reduce positive charge.

ShpKa#8: Plasma Kallikrein binder from shortened LACI-K1 #5
```
          1111111222222222233333333333
          34567890123456789012345 6789
          HCKANHQCCFFNPDARQCEEFSCGGCG
```
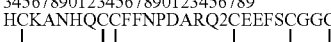

(SEQ ID NO: 24)

Change 24–27 to NPDA (found in *Drosophila funebris* KuDom) to get a proline into loop.

TABLE 100

Sequence of whole LACI:

|     |              |            |            |            |            |
| --- | ------------ | ---------- | ---------- | ---------- | ---------- |
| 1   | MIYTMKKVHA   | LWASVCLLLN | LAPAPLNAds | eedeehtiit | dtelpplklM |
| 51  | HSFCAFKADD   | GPCKAIMKRF | FFNIFTRQCE | EFIYGGCEGN | QNRFESLEEC |
| 101 | KKMCTRDnan   | riikttlqqe | kpdfcfleed | pgicrgyitr | yfynnptkac |
| 151 | erfkyggclg   | nmnnfetlee | cknicedgpn | gfqvdnygtq | lnavnnsltp |
| 201 | qstkvpslfe   | fhgpsweltp | adrglcrane | nrfyynsvig | kcrpfkysgc |
| 251 | ggnennftsk   | qeclrackkg | fiqriskggl | iktkrkrkkq | rvkiayeeif |
| 301 | vknm         |            |            |            |            |

(SEQ ID NO:25)

The signal sequence (1-28) is uppercase and underscored
   LACI-K1 is uppercase
   LACI-K2 is underscored
   LACI-K3 is bold

TABLE 103

LACI-K1 derivatives that bind and inhibit human plasma Kallikrein

|         |              | 13 | 14 | 15 | 16 | 17 | 18 | 19 | 31 | 32 | 34 | 39(a) |
| ------- | ------------ | -- | -- | -- | -- | -- | -- | -- | -- | -- | -- | ----- |
| KKII/3#1  | (SEQ ID NO: 2)  | H | C | K | A | S | L | P | E | E | I | E |
| KKII/3#2  | (SEQ ID NO: 3)  | P | C | K | A | N | H | L | E | E | S | G |
| KKII/3#3  | (SEQ ID NO: 4)  | H | C | K | A | N | H | Q | E | E | T | G |
| KKII/3#4  | (SEQ ID NO: 5)  | H | C | K | A | N | H | Q | E | Q | T | A |
| KKII/3#5  | (SEQ ID NO: 6)  | H | C | K | A | S | L | P | E | E | I | G |
| KKII/3#6  | (SEQ ID NO: 7)  | H | C | K | A | N | H | Q | E | E | S | G |
| KKII/3#7  | (SEQ ID NO: 8)  | H | C | K | A | N | H | Q | E | E | S | G |
| KKII/3#8  | (SEQ ID NO: 9)  | H | C | K | A | N | H | Q | E | E | S | G |
| KKII/3#9  | (SEQ ID NO: 10) | H | C | K | A | N | H | Q | E | E | S | G |
| KKII/3#10 | (SEQ ID NO: 11) | H | C | K | G | A | H | L | E | E | I | E |

TABLE 103-continued

LACI-K1 derivatives that bind and inhibit human plasma Kallikrein

|  | 13 | 14 | 15 | 16 | 17 | 18 | 19 | 31 | 32 | 34 | 39(a) |
|---|---|---|---|---|---|---|---|---|---|---|---|
| Consensus | H | C | K | A | N | H | Q | E | E | S/T | G |
| Fixed |  | C | K |  |  |  |  |  |  |  |  |
| Absolute |  |  |  |  |  |  |  | E |  |  |  |
| Strong preference | H |  |  | A |  | H |  |  | E |  |  |
| Good selection |  |  |  |  | N |  | Q |  |  |  | G |
| Some selection |  |  |  |  |  |  |  |  |  | S/T |  |

TABLE 202 vgDNA for LACI-D1 to vary residues 10, 11, 13, 15, 16, 17, & 19 for pKA in view of previous selections.

```
                                          N|K
  M   H   S   F   C   A   F   K   A   D|E
  1   2   3   4   5   6   7   8   9   10
  5'-t|tcc|ttc|tgc|gcc|ttc|aag|gct|RaS A|T
                                  S|P
   N|S           E                H|N
   I|T           K|D              Y|Q
   A|G           Y|Q       V|D    K|D
   D|V    G   H|N   C   K|R   A|G   N|S   H|L   E   R
   11    12    13   14   15    16    17    18    19  20
   |RNt  |ggt |NcS |tgt |aRa  |gNt  |aRt  |cWt  |NMS |cgt|

F    F    F    N    I    F    T    R        (SEQ ID NO:26)
   21   22   23   24   25   26   27   28
   |ttc|ttc|ttc|aac|atc|ttc|a-3'                 (SEQ ID NO:28)
```

DNA: 131,072
protein: 78,848

TABLE 204

Variation of Residues 31, 32, 34, 39, 40, 41, and 42 for pKA in view of previous selections.

```
           T   R   Q   C
      5'-|acg|ctg|cag|tgc|
           |  MluI |

W   W
        Q|S Q|S
        L|P L|P
        K|R K|R
        M|T M|T
        V|A V|A    T|S
        E|G E|G F A|P Y   G   G   C   Xg  G|A  N|K  Q|R
        31  32  33  34  35  36  37  38  39   40   41   42
       |Nng|Nng|ttc|Nct|tac|ggt|ggt|tgt|NNG|gSc|aaS|cRa|
                                              (| BstEII |)

43  44
        N   R           (SEQ ID NO: 28)
       |aac|cgG|t-3'
             | AgeI |   (SEQ ID NO: 29)
```

There are 131,072 DNA sequences and 70,304 protein sequences.

TABLE 220

Cα—Cα distances in P1 region of BPTI

|  | T11 | G12 | P13 | C14 | K15 | A16 | R17 | I18 | I19 | R20 |
|---|---|---|---|---|---|---|---|---|---|---|
| G12 | 3.8 |  |  |  |  |  |  |  |  |  |
| P13 | 7.0 | 3.8 |  |  |  |  |  |  |  |  |
| C14 | 8.0 | 5.9 | 3.9 |  |  |  |  |  |  |  |
| K15 | 8.9 | 8.2 | 6.5 | 3.7 |  |  |  |  |  |  |
| A16 | 9.5 | 9.9 | 9.4 | 6.1 | 3.8 |  |  |  |  |  |
| R17 | 9.1 | 10.9 | 11.4 | 8.9 | 6.5 | 3.8 |  |  |  |  |
| I18 | 9.2 | 11.3 | 12.7 | 10.3 | 9.0 | 5.9 | 3.8 |  |  |  |
| I19 | 10.0 | 12.9 | 15.1 | 13.4 | 12.2 | 9.5 | 6.6 | 3.8 |  |  |
| R20 | 9.6 | 12.6 | 15.4 | 14.2 | 14.1 | 11.7 | 9.6 | 6.3 | 3.8 |  |
| Y21 | 11.2 | 14.4 | 17.7 | 17.1 | 17.3 | 15.3 | 13.0 | 10.1 | 7.1 | 3.9 |
| Q31 | 13.6 | 17.2 | 20.5 | 20.5 | 20.1 | 18.4 | 15.5 | 13.4 | 9.9 | 8.2 |
| T32 | 11.2 | 14.9 | 18.0 | 17.4 | 16.7 | 14.9 | 11.8 | 9.8 | 6.3 | 5.4 |
| V34 | 6.0 | 9.4 | 11.6 | 10.8 | 9.8 | 8.5 | 5.8 | 5.5 | 5.0 | 6.4 |

|  | Q31 | T32 | V34 |
|---|---|---|---|
| T32 | 3.8 |  |  |
| V34 | 10.4 | 7.1 |  |

TABLE 1017

High specificity plasma Kallikrein inhibitors

LACI-K1

MHSFCAFKADDGPCKAIMKRFFFNIFTRQCEEFIYGGCEGNQNRFESLEECKKMCTRD
(residues 50-107 of SEQ ID NO: 25 (SEQ ID NO: 62))
KKII/3#7 mhsfcafkaddgHckANHQrfffniftrqcEEfSyggcGgnqnrfesleeckkmctrd (SEQ ID NO: 8)
KKII/3#7-K15A mhsfcafkaddgHcaANHQrfffniftrqcEEfSyggcGgnqnrfesleeckkmctrd (SEQ ID NO: 31)

REFERENCES CITED

ANBA88 Biochimie (1988) 70(6)727-733. "Improving the stability of a foreign protein in the periplasmic space of *Escherichia coli*." Anba J; Bernadac A; Lazdunski C; Pages J M AUER88: Auerswald, E-A, D Hoerlein, G Reinhardt, W Schroder, and E Schnabel, "Expression, Isolation, and Characterization of Recombinant [Arg$^{15}$,Glu$^{52}$]Aprotinin", *Bio Chem Hoppe-Seyler* (1988), 369(Supplement): 27-35.

BANE90: J Bacteriol (1990 (January)) 172(1)491-494. "In vivo degradation of secreted fusion proteins by the *Escherichia coli* outer membrane protease OmpT."Baneyx F; Georgiou G BANE91: J Bacteriol (1991 (April)) 173(8)2696-2703. "Construction and characterization of *Escherichia coli* strains deficient in multiple secreted proteases: protease III degrades high-molecular-weight substrates in vivo."Baneyx, F, & G Georgiou BHOO92: Pharmacological Reviews (1992) 44(1)1-80. "Bioregulation of Kinins: Kallikreins, Kininogens, and Kininases", Bhoola, K D, C D Figueroa, and K Worthy.

BROZ90: BROZE G. J. JR., GIRARD T. J. & NOVOTNY W. F. *BIOCHEMISTRY* (1990) 29:7539-7546. MEDLINE identifier: 91104709

COLM87: Colman, R W, J Hirsh, V J Marder, and E W Salzman, Editors, Hemostasis and Thrombosis, Second Edition, 1987, J. B. Lippincott Company, Philadelphia, Pa.

COLM87a: Colman, R W, V J Marder, E W Salzman, and J Hirsh, Chapter 1 of COLM87. "Overview of Hemostasis".

EIGE90: Eigenbrot, C, M Randal, and A A Kossiakoff, "Structural effects induced by removal of a disulfide-bridge: the X-ray structure of the C30A/C51A mutant of basic pancreatic trypsin inhibitor at 1.6 Å", *Protein Engineering* (1990), 3(7)591-598.

GIRA89: Girard, T J, L A Warren, W F Novotny, K M Likert, S G Brown, J P Miletich, and G J Broze Jr, "Functional significance of the Kunitz-type inhibitory domains of lipoprotein-associated coagulation inhibitor", *Nature* (1989), 338:518-20.

GIRA91: GIRARD T. J., EDDY R., WESSELSCHMIDT R. L., MACPHAIL L. A., LIKERT K. M., BYERS M. G., SHOWS T. B. & BROZE G. J. JR. *J. BIOL. CHEM.* (1991) 266:5036-5041. MEDLINE identifier: 91161593

HOOV93: Hoover, G J, N Menhart, A Martin, S Warder, and F J Castellino, "Amino Acids of th Recombinant Kringle 1 Domain of Human Plasminogen That Stabilize Its Interaction with ω-Amino Acids."*Biochemistry* (1993) 32:10936-43.

HYNE90: Hynes, T R, M Randal, L A Kenedy, C Eigenbrot, and A A Kossiakoff, "X-ray crystal structure of the protease inhibitor domain of Alzheimer's amyloid beta-protein precursor", *Biochemistry* (1990), 29:10018-10022.

KIDO90: Kido, H, A Fukutomi, J Schelling, Y Wang, B Cordell, and N Katunuma, "Protease-Specificity of Kunitz Inhibitor Domain of Alzheimer's Disease Amyloid Protein Precursor", *Biochem & Biophys Res Comm* (Mar. 16, 1990), 167(2)716-21.

LASK80: Laskowski, M, Jr, and I Kato, "Protein Inhibitors of Proteases", *Ann Rev Biochem* (1980), 49:593-626.

NEUH89: Neuhaus, P, W O Bechstein, B Lefebre, G Blumhardt, and K Slama, *Lancet* (1989) 2(8668)924-5. "Effect of aprotinin on intraoperative bleeding and fibrinolysis in liver transplantation [letter]."

NOVO89: NOVOTNY W. F., GIRARD T. J., MILETICH J. P. & BROZE G. J. JR. *J. BIOL. CHEM.* (1989) 264:18832-18837. MEDLNE identifier: 90036996

PUTT89: Putterman, C, *Acta Chir Scand* (1989) 155(6-7) 367. "Aprotinin therapy in septic shock [letter; comment]"

SCHE67: Biochem Biophys Res Commun (1967) 27:157-162. "On the size of the active site in proteases. I. Papain" Schechter, I, and A Berger.

SCHE68: Biochem Biophys Res Commun (1968) 32:898-902. "On the active site of proteases. III. Mapping the active site of papain; specific peptide inhibitors of papain."Schechter, I, and A Berger.

SCHM87: Schmaier, A H, M Silverberg, A P Kaplan, and R W Colman, Chapter 2 in COLM87. "Contact Activation and Its Abnormalities".

SCHN86: Schnabel, E, W Schroeder, and G Reinhardt, "[Ala$_2^{14,38}$]Aprotinin: Preparation by Partial Desulphurization of Aprotinin by Means of Raney Nickel and Comparison with other Aprotinin Derivatives", *Biol Chem Hoppe-Seyler* (1986), 367:1167-76.

VAND91: VAN DER LOGT C. P. E., REITSMA P. H. & BERTINA R. M. *BIOCHEMISTRY* (1991) 30:1571-1577. MEDLINE identifier: 91129227

VAND92 EMBO J (1992 (August)) 11(8)2819-2828. "Signal peptidase I of *Bacillus subtilis*: patterns of conserved amino acids in prokaryotic and eukaryotic type I signal peptidases."van Dijl, J M, A de Jong, J Vehmaanpera, G Venema, S Bron WUNT88: WUN T.-C., KRETZMER K. K., G T. J., MILETICH J. P. & BROZE G. J. JR. *J. BIOL. CHEM.* (1988) 263:6001-6004. MEDLINE identifier: 88198127

LEAT91: "Design of a small peptide-based proteinase inhibitor by modeling the active-site region of barley chymotrypsin inhibitor 2."Leatherbarrow R J; Salacinski H J *Biochemistry* (1991) 30(44)10717-21.

KLIN91: "Hirulog peptides with scissile bond replacements resistant to thrombin cleavage. Kline T; Hammond C; Bourdon P; Maraganore J M *Biochem Biophys Res Commun* (Jun. 28, 1991) 177(3)1049-55.

DIMA91: "A new class of potent thrombin inhibitors that incorporates a scissile pseudopeptide bond."DiMaio J; Ni F; Gibbs B; Konishi Y *FEBS Lett* (Apr. 22, 1991) 282(1) 47-52.

ANGL87: "The synthesis of lysylfluoromethanes and their properties as inhibitors of trypsin, plasmin and cathepsin B."Angliker H; Wikstrom P; Rauber P; Shaw E *Biochem J* (1987) 241(3)871-5.

TIAN92: Tian Z; Edwards P; Roeske R W "Synthesis of optically pure C α-methyl-arginine."*Int J Pept Protein Res* (August 1992) 40(2)119-26.

MARC85: Advanced Organic Chemistry, Third Edition March, J, John Wiley and Sons, New York, 1985; ISBN 0-471-88841-9.

CARE90: Advanced Organic Chemistry, Third Edition, Part B, Reactions and Synthesis Carey, F A, and R J Sundberg, Plenum Press, New York, 1990; ISBN 0-306-43456-3.

HORT91: "Allosteric changes in thrombin's activity produced by peptides corresponding to segments of natural inhibitors and substrates."Hortin G L; Trimpe B L *J Biol Chem* (Apr. 15, 1991) 266(11)6866-71.

MCCO90: "New leupeptin analogues: synthesis and inhibition data."McConnell R M; Barnes G E; Hoyng C F; Gunn J M *J Med Chem* (1990) 33(1)86-93.

NAGA85: "Synthesis of a bicyclic dipeptide with the shape of .beta.-turn central part"Nagai, U, and K Sato, *Tetrahedron Lett.* (1985) 26(5)647-50.

NAGA93: "Bicyclic Turned Dipeptide (BTD) as a β-Turn Mimetic: its Design, Synthesis and Incorportaion into Bioactive Peptides"Nagai, U, K Sato, R Nakamura, and R Kato *Tetrahedron* (1993) 49(17)3577-92.

KEMP88b: "Synthesis of Peptide-functionalized diacylaminoepindolidiones as Templates for β-sheet formation" Kemp, D S, and B R Bowen *Tetrahedron Letts* (1988) 29:5077-5080.

FREI82: "Protected lactam-bridged dipeptides for use as conformational constraints in peptides."Freidinger, R M, D S Perlow, and D F Veber, *J Org Chem* (1982) 47(1)104-9.

DIAZ93: "The Design of Water Soluble β-Sheet Structure Based On a Nucleation Strategy."Diaz, H, K Y Tsang, D Choo, and J W Kelly *Tetrahedron* (1993) 49(17)3533-45.

CURR93: "Design and Synthesis of a Bicyclic Non-Peptide β-Bend Mimetic of Enkephalin"Currie, B L, J L Krstenansky, Z-L Lin, J Ungwitayatorn, Y-H Lee, M del Rosario-Chow, W-S Sheu, and M E Johnson *Tetrahedron* (1993) 49(17)3489-3500.

WILS93: "The Calculation of Synthesis of a Template Molecule."Wilson, S R, W K Tam, M J DiGrandi, and W Cui *Tetrahedron* (1993)49(17)3655-63.

The invention claimed is:

1. A method of treating edema in a mammalian subject, comprising:
   administering to the subject a kallikrein inhibiting protein comprising a non-naturally occurring Kunitz domain, said Kunitz domain having disulfide bonds at Cys5-Cys55, Cys14-Cys38, and Cys30-Cys51 and further having:

amino acid number 13 selected from the group consisting of His and Pro;

amino acid number 14 as Cys;

amino acid number 16 selected from the group consisting of Ala and Gly;

amino acid number 17 selected from the group consisting of Ala, Asn, and Ser;

amino acid number 18 selected from the group consisting of His and Leu;
amino acid number 19 selected from the group consisting of Gln, Leu, and Pro,
amino acid number 31 as Glu;
amino acid number 32 selected from the group consisting of Glu and Gln;
amino acid number 34 selected from the group consisting of Ser, Thr, and Ile; and
amino acid number 39 selected from the group consisting of Gly, Glu, and Ala,
wherein the above amino acids are numbered to correspond to the numbering of amino acid residues of bovine pancreatic trypsin inhibitor (BPTI) (SEQ ID NO:1), and wherein the kallikrein inhibiting protein binds plasma kallikrein with a Ki less than 500 pM.

2. The method of claim 1, wherein the edema is angioedema.

3. The method of claim 1, wherein the edema is associated with sepsis.

4. The method of claim 1, wherein the edema is associated with trauma.

5. The method of claim 1, wherein the edema is associated with asthma.

6. The method of claim 1, wherein the edema is hereditary edema.

7. The method of claim 1, wherein the Kunitz domain further has:
amino acid number 15 selected from the group consisting of Lys and Arg;
wherein the above amino acids are numbered to correspond to the numbering of amino acid residues of bovine pancreatic trypsin inhibitor (BPTI) (SEQ ID NO: 1).

8. The method of claim 1, wherein the Kunitz domain is selected from the group consisting of SEQ. ID. NO.2, SEQ. ID. NO.3, SEQ. ID. NO.4, SEQ. ID. NO.5, SEQ. ID. NO.6, SEQ. ID. NO.7, SEQ. ID. NO.8, SEQ. ID. NO.9, SEQ. ID. NO.10, SEQ. ID. NO.11, SEQ ID NO:13, SEQ ID NO:14, SEQ ID NO:17, SEQ ID NO:21, SEQ ID NO:27, SEQ ID NO:28, SEQ ID NO:64, and SEQ ID NO:66.

9. The method of claim 1, wherein the subject is human.

10. The method of claim 1, wherein the kallikrein inhibiting protein is administered as part of a pharmaceutical composition that further comprises a pharmaceutically acceptable carrier.

11. The method of claim 1, wherein the kallikrein inhibiting protein binds plasma kallikrein with a Ki less than 50 pM.

12. The method of claim 1, wherein the kallikrein inhibiting protein is administered parenterally.

13. The method of claim 12, wherein the kallikrein inhibiting protein is administered subcutaneously.

* * * * *

UNITED STATES PATENT AND TRADEMARK OFFICE
CERTIFICATE OF CORRECTION

PATENT NO. : 7,628,983 B2  Page 1 of 1
APPLICATION NO. : 11/365438
DATED : December 8, 2009
INVENTOR(S) : Markland et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 396 days.

Signed and Sealed this

Second Day of November, 2010

David J. Kappos
*Director of the United States Patent and Trademark Office*

```
                       SEQUENCE LISTING

<160> NUMBER OF SEQ ID NOS: 62

<210> SEQ ID NO 1
<211> LENGTH: 58
<212> TYPE: PRT
<213> ORGANISM: Bos taurus

<400> SEQUENCE: 1

Arg Pro Asp Glu Cys Leu Glu Pro Pro Tyr Thr Gly Pro Cys Lys Ala
1               5                   10                  15

Arg Ile Ile Arg Tyr Glu Tyr Asn Ala Lys Ala Gly Leu Cys Gln Thr
            20                  25                  30

Phe Val Tyr Gly Gly Cys Arg Ala Lys Arg Asn Asn Glu Lys Ser Ala
        35                  40                  45

Glu Asp Cys Met Arg Thr Cys Gly Gly Ala
    50                  55

<210> SEQ ID NO 2
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 2

Met His Ser Phe Cys Ala Phe Lys Ala Asp Asp Gly His Cys Lys Ala
1               5                   10                  15

Ser Leu Pro Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55
```

```
<210> SEQ ID NO 3
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 3

Met His Ser Phe Cys Ala Phe Lys Ala Asp Asp Gly Pro Cys Lys Ala
 1               5                  10                  15

Asn His Leu Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 4
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 4

Met His Ser Phe Cys Ala Phe Lys Ala Asp Asp Gly His Cys Lys Ala
 1               5                  10                  15

Asn His Gln Arg Phe Phe Asn Ile Phe Thr Arg Gln Cys Glu Glu
            20                  25                  30

Phe Thr Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 5
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 5

Met His Ser Phe Cys Ala Phe Lys Ala Asp Asp Gly His Cys Lys Ala
 1               5                  10                  15

Asn His Gln Arg Phe Phe Asn Ile Phe Thr Arg Gln Cys Glu Gln
            20                  25                  30

Phe Thr Tyr Gly Gly Cys Ala Gly Asn Gln Asn Arg Phe Glu Ser Leu
            35                  40                  45

Glu Glu Cys Lys Lys Met Cys Thr Arg Asp
    50                  55

<210> SEQ ID NO 6
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 6

Met His Ser Phe Cys Ala Phe Lys Ala Asp Asp Gly His Cys Lys Ala
 1               5                  10                  15

Ser Leu Pro Arg Phe Phe Phe Asn Ile Phe Thr Arg Gln Cys Glu Glu
```

```
                20                  25                  30

Phe Ile Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 7
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 7

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 8
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 8

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 9
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 9

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 10
<211> LENGTH: 58
<212> TYPE: PRT
<213> ORGANISM: Artificial Sequence
```

<220> FEATURE:
<223> OTHER INFORMATION: Synthetically generated peptide

<400> SEQUENCE: 10

Met His Ser Phe Cys Ala Phe Lys Ala Asp Asp Gly His Cys Lys Ala
1               5                   10                  15

Asn His Gln Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 11
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 11

Met His Ser Phe Cys Ala Phe Lys Ala Asp Asp Gly His Cys Lys Gly
1               5                   10                  15

Ala His Leu Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

<210> SEQ ID NO 12
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 12

Met His Ser Phe Cys Ala Phe Lys Ala Asp Asp Gly Arg Cys Lys Gly
1               5                   10                  15

Ala His Leu Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55

<210> SEQ ID NO 13
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 13

Met His Ser Phe Cys Ala Phe Lys Ala Asp Asp Gly Pro Cys Lys Ala
1               5                   10                  15

Ile His Leu Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

```
Glu Glu Cys Lys Lys Met Cys Thr Arg Asp
    50                  55

<210> SEQ ID NO 14
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 14

Met His Ser Phe Cys Ala Phe Lys Ala Asp Asp Gly His Cys Lys Ala
 1               5                  10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 15
<211> LENGTH: 62
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 15
<223> OTHER INFORMATION: Xaa = His or Arg; Leu or Pro
<220> FEATURE:
<221> NAME/KEY: VARIANT
<222> LOCATION: 18
<223> OTHER INFORMATION: Xaa = Ala or Gly
<220> FEATURE:
<221> NAME/KEY: VARIANT
<222> LOCATION: 19
<223> OTHER INFORMATION: Xaa = Gly; Ala or Asp; Asn or Val; Ile or
      Thr; His or Arg; Leu or Pro; Tyr or Cys; Phe or Ser
<220> FEATURE:
<221> NAME/KEY: VARIANT
<222> LOCATION: 20
<223> OTHER INFORMATION: Xaa = Asp or Gly; Ala or Glu; Lys or Val; Met
      or Thr; Gln or Arg; Trp or Pro; Leu or Ser; Phe or Tyr; Cys or
      His; Ile or Asn
<220> FEATURE:
<221> NAME/KEY: VARIANT
<222> LOCATION: 21
<223> OTHER INFORMATION: Xaa = Gly; Ala or Glu; Lys or Val;Met or Thr;
      Gln or Arg; Trp or Pro; Leu or Ser;
<220> FEATURE:
<221> NAME/KEY: VARIANT
<222> LOCATION: 33, 34
<223> OTHER INFORMATION: Xaa = Glu or Gln
<220> FEATURE:
<221> NAME/KEY: VARIANT
<222> LOCATION: 36
<223> OTHER INFORMATION: Xaa = Gly or Trp; Ala or Asp; Asn or Val; Ile
      or Thr; His or Arg; Leu or Pro; Tyr or Cys; Phe or Ser; Met or
      Lys; Gln or Glu
<220> FEATURE:
<221> NAME/KEY: VARIANT
<222> LOCATION: 41
<223> OTHER INFORMATION: Xaa = Gly or Asp; Ala or Glu; Lys or Val; Met
      or Thr; Gln or Arg; Trp or Pro; Leu or Ser; Phe or Tyr; Cys or
      Ile; Asn or His

<400> SEQUENCE: 15

Ala Glu Met His Ser Phe Cys Ala Phe Lys Ala Asp Asp Gly Xaa Cys
 1               5                  10                  15
```

-continued

```
Lys Xaa Xaa Xaa Arg Phe Phe Asn Ile Phe Thr Arg Gln Cys
         20                  25                  30

Xaa Xaa Phe Xaa Tyr Gly Gly Cys Xaa Gly Asn Gln Asn Arg Phe Glu
         35                  40                  45

Ser Leu Glu Glu Cys Lys Lys Met Cys Thr Arg Asp Gly Ala
 50                  55                  60
```

<210> SEQ ID NO 16
<211> LENGTH: 186
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 44, 55, 56, 58, 59, 61-62, 106, 107, 121, 122
<223> OTHER INFORMATION: n = a, t, c or g
<220> FEATURE:
<221> NAME/KEY: CDS
<222> LOCATION: (1)...(186)

<400> SEQUENCE: 16

```
gcc gag atg cat tcc ttc tgc gcc ttc aag gct gat gat ggt cnt tgt      48
Ala Glu Met His Ser Phe Cys Ala Phe Lys Ala Asp Asp Gly Xaa Cys
 1               5                  10                  15 aaa gst nnt nns nng cgt ttc ttc ttc aac atc ttc acg cgt cag tgc     96
Lys Xaa Xaa Xaa Xaa Arg Phe Phe Phe Asn Ile Phe Thr Arg Gln Cys
                 20                  25                  30 sag saa ttc nns tac ggt ggt tgt nns ggt aac cag aac cgg ttc gaa    144
Xaa Xaa Phe Xaa Tyr Gly Gly Cys Xaa Gly Asn Gln Asn Arg Phe Glu
         35                  40                  45 tct cta gag gaa tgt aag aag atg tgc act cgt gac ggc gcc            186
Ser Leu Glu Glu Cys Lys Lys Met Cys Thr Arg Asp Gly Ala
 50                  55                  60
```

<210> SEQ ID NO 17
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 17

```
His Cys Lys Ala Asn His Gln Arg Cys Phe Tyr Asn Ala Lys Ala Gly
 1               5                  10                  15

Leu Cys Glu Glu Phe Ser Tyr Gly Gly Cys Gly
             20                  25
```

<210> SEQ ID NO 18
<211> LENGTH: 40
<212> TYPE: PRT
<213> ORGANISM: Artificial Sequence
<220> FEATURE:
<223> OTHER INFORMATION: Synthetically generated peptide

<400> SEQUENCE: 18

```
His Cys Lys Ala Asn His Gln Arg Tyr Phe Tyr Asn Ala Lys Ala Gly
 1               5                  10                  15

Leu Cys Glu Glu Phe Thr Tyr Gly Gly Cys Gly Ala Lys Arg Asn Asn
             20                  25                  30

Phe Lys Ser Ala Glu Asp Cys Met
         35                  40
```

<210> SEQ ID NO 19

```
<211> LENGTH: 40
<212> TYPE: PRT
<213> ORGANISM: Artificial Sequence
<220> FEATURE:
<223> OTHER INFORMATION: Synthetically generated peptide

<400> SEQUENCE: 19

His Cys Arg Ala Asn His Gln Cys Tyr Phe Tyr Asn Ala Lys Ala Gly
 1               5                  10                  15

Leu Cys Glu Glu Phe Ser Cys Gly Gly Cys Gly Ala Lys Arg Asn Asn
            20                  25                  30

Phe Lys Ser Ala Glu Asp Cys Met
        35                  40

<210> SEQ ID NO 20
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 20

His Cys Lys Ala Asn His Gln Arg Cys Phe Phe Asn Ile Phe Thr Arg
 1               5                  10                  15

Gln Cys Glu Glu Phe Ser Tyr Gly Gly Cys Gly
            20                  25

<210> SEQ ID NO 21
<211> LENGTH: 26
<212> TYPE: PRT
<213> ORGANISM: Artificial Sequence
<220> FEATURE:
<223> OTHER INFORMATION: Synthetically generated peptide

<400> SEQUENCE: 21

His Cys Lys Ala Asn His Gln Arg Cys Phe Phe Asn Gly Thr Arg Gln
 1               5                  10                  15

Cys Glu Glu Phe Ser Tyr Gly Gly Cys Gly
            20                  25

<210> SEQ ID NO 22
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 22

His Cys Lys Ala Asn His Gln Cys Cys Phe Phe Asn Ile Phe Thr Arg
 1               5                  10                  15

Gln Cys Glu Glu Phe Ser Cys Gly Gly Cys Gly
            20                  25

<210> SEQ ID NO 23
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 23

His Cys Lys Ala Asn His Gln Cys Cys Phe Phe Asp Val Thr Glu Arg
 1               5                  10                  15

Gln Cys Glu Glu Phe Ser Cys Gly Gly Cys Gly
```

<210> SEQ ID NO 24
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 24

```
His Cys Lys Ala Asn His Gln Cys Cys Phe Phe Asn Pro Asp Ala Arg
 1               5                  10                  15

Gln Cys Glu Glu Phe Ser Cys Gly Gly Cys Gly
             20                  25
```

<210> SEQ ID NO 25
<211> LENGTH: 304
<212> TYPE: PRT
<213> ORGANISM: Homo sapiens

<400> SEQUENCE: 25

```
Met Ile Tyr Thr Met Lys Lys Val His Ala Leu Trp Ala Ser Val Cys
 1               5                  10                  15

Leu Leu Leu Asn Leu Ala Pro Ala Pro Leu Asn Ala Asp Ser Glu Glu
             20                  25                  30

Asp Glu Glu His Thr Ile Ile Thr Asp Thr Glu Leu Pro Pro Leu Lys
         35                  40                  45

Leu Met His Ser Phe Cys Ala Phe Lys Ala Asp Asp Gly Pro Cys Lys
     50                  55                  60

Ala Ile Met Lys Arg Phe Phe Phe Asn Ile Phe Thr Arg Gln Cys Glu
 65                  70                  75                  80

Glu Phe Ile Tyr Gly Gly Cys Glu Gly Asn Gln Asn Arg Phe Glu Ser
                 85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
    130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270

Gln Arg Ile Ser Lys Gly Gly Leu Ile Lys Thr Lys Arg Lys Arg Lys
        275                 280                 285
```

Lys Gln Arg Val Lys Ile Ala Tyr Glu Glu Ile Phe Val Lys Asn Met
    290                 295                 300

<210> SEQ ID NO 26
<211> LENGTH: 28
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 10
<223> OTHER INFORMATION: Xaa = Asp or Glu; Asn or Lys
<220> FEATURE:
<221> NAME/KEY: VARIANT
<222> LOCATION: 11
<223> OTHER INFORMATION: Xaa = Asp or Val; Ala or Gly; Ile or Thr;
      Asn or Ser
<220> FEATURE:
<221> NAME/KEY: VARIANT
<222> LOCATION: 13
<223> OTHER INFORMATION: Xaa = His or Asn; Tyr or Gln; Lys or Asp; Gly
<220> FEATURE:
<221> NAME/KEY: VARIANT
<222> LOCATION: 15
<223> OTHER INFORMATION: Xaa = Lys or Arg; Val or Asp
<220> FEATURE:
<221> NAME/KEY: VARIANT
<222> LOCATION: 16
<223> OTHER INFORMATION: Xaa = Ala or Gly
<220> FEATURE:
<221> NAME/KEY: VARIANT
<222> LOCATION: 17
<223> OTHER INFORMATION: Xaa = Asn or Ser
<220> FEATURE:
<221> NAME/KEY: VARIANT
<222> LOCATION: 18
<223> OTHER INFORMATION: Xaa = His or Leu
<220> FEATURE:
<221> NAME/KEY: VARIANT
<222> LOCATION: 19
<223> OTHER INFORMATION: Xaa = Glu; Lys or Asp; Tyr or Gln; His or
      Asn; Ser or Pro; Ala or Thr

<400> SEQUENCE: 26

Met His Ser Phe Cys Ala Phe Lys Ala Xaa Xaa Gly Xaa Cys Xaa Xaa
  1               5                  10                  15

Xaa Xaa Xaa Arg Phe Phe Phe Asn Ile Phe Thr Arg
             20                  25

<210> SEQ ID NO 27
<211> LENGTH: 74
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (2)...(74)
<220> FEATURE:
<221> NAME/KEY: misc_feature
<222> LOCATION: 27, 32, 42, 50
<223> OTHER INFORMATION: n = a, t, c, or g

<400> SEQUENCE: 27 t tcc ttc tgc gcc ttc aag gct ras rnt ggt ncs tgt ara gnt art cwt    49
  Ser Phe Cys Ala Phe Lys Ala Xaa Xaa Gly Xaa Cys Xaa Xaa Xaa Xaa
  1               5                  10                  15 nms cgt ttc ttc ttc aac atc ttc a                                    74
Xaa Arg Phe Phe Phe Asn Ile Phe

```
<210> SEQ ID NO 28
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 5
<223> OTHER INFORMATION: Xaa = Glu or Gly; Val or Ala; Met or Thr; lys
      or Arg; Leu or Pro; Gln or Ser; Trp
<220> FEATURE:
<221> NAME/KEY: VARIANT
<222> LOCATION: 6
<223> OTHER INFORMATION: Xaa = Glu or Gly; Val or Ala; Met or Thr; lys
      or Arg; Leu or Pro; Gln or Ser; Trp
<220> FEATURE:
<221> NAME/KEY: VARIANT
<222> LOCATION: 8
<223> OTHER INFORMATION: Xaa = Ala or Pro; Thr or Ser
<220> FEATURE:
<221> NAME/KEY: VARIANT
<222> LOCATION: 13
<223> OTHER INFORMATION: Xaa = any amino acid or Gly
<220> FEATURE:
<221> NAME/KEY: VARIANT
<222> LOCATION: 14
<223> OTHER INFORMATION: Xaa = Gly or Ala
<220> FEATURE:
<221> NAME/KEY: VARIANT
<222> LOCATION: 15
<223> OTHER INFORMATION: Xaa = Asn or Lys
<220> FEATURE:
<221> NAME/KEY: VARIANT
<222> LOCATION: 16
<223> OTHER INFORMATION: Xaa = Gln or Arg

<400> SEQUENCE: 28

Thr Arg Gln Cys Xaa Xaa Phe Xaa Tyr Gly Gly Cys Xaa Xaa Xaa Xaa
 1               5                  10                  15

Asn Arg

<210> SEQ ID NO 29
<211> LENGTH: 55
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(55)
<220> FEATURE:
<221> NAME/KEY: misc_feature
<222> LOCATION: 13, 14, 16, 17, 22, 37, 38
<223> OTHER INFORMATION: n = a, t, c, or g

<400> SEQUENCE: 29 acg cgt cag tgc nng nng ttc nct tac ggt ggt tgt nng gsc aas cra      48
Thr Arg Gln Cys Xaa Xaa Phe Xaa Tyr Gly Gly Cys Xaa Xaa Xaa Xaa
 1               5                  10                  15 aac cgg t                                                            55
Asn Arg

<210> SEQ ID NO 30
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 30
```

```
Gly Pro Thr Val Thr Thr Gly
 1               5
```

<210> SEQ ID NO 31
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 31

```
Met His Ser Phe Cys Ala Phe Lys Ala Asp Asp Gly His Cys Ala Ala
 1               5                  10                  15

Asn His Gln Arg Phe Phe Phe Asn Ile Phe Thr Arg Gln Cys Glu Glu
            20                  25                  30

Phe Ser Tyr Gly Gly Cys Gly Asn Gln Asn Arg Phe Glu Ser Leu
        35                  40                  45

Glu Glu Cys Lys Lys Met Cys Thr Arg Asp
    50                  55
```

<210> SEQ ID NO 32
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 32

```
Gly Pro Gly Glu Cys
 1               5
```

<210> SEQ ID NO 33
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 33

```
His Cys Lys Ala Asn His
 1               5
```

<210> SEQ ID NO 34
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 34

```
Gly His Pro Lys Ala Asn His Gln Leu
 1               5
```

<210> SEQ ID NO 35
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 35

```
His Pro Arg Ala Asn His Gln
 1               5
```

<210> SEQ ID NO 36

```
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 36

Pro Arg Ala Asn His
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = acetylglycine

<400> SEQUENCE: 37

Xaa His Met Lys Ala Asn His Gln Glu
1               5

<210> SEQ ID NO 38
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 38

His Cys Lys Ala Asn His Gln Glu Thr Ile Thr Thr Cys
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 39

His Cys Arg Ala Asn His Gln Glu Glu Thr Thr Val Thr Gly Cys
1               5                   10                  15

<210> SEQ ID NO 40
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 40

Gly His Cys Arg Ala Gln His Gln Gly Pro Thr Gly Cys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 41

His Pro Arg Ala Asn His Gln Gly Glu Thr Val Thr Thr
1               5                   10
```

```
<210> SEQ ID NO 42
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 42

Cys His Cys Lys Ala Asn His Gln Glu Gly Pro Thr Val Thr Gly Cys
1               5                   10                  15

Cys

<210> SEQ ID NO 43
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 43

His Cys Lys Ala Asn His Gln Ala Glu Glu Thr Ile Thr Cys Cys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 44

His Cys Cys Lys Ala Asn His Gln Glu Thr Asp Ile Gly Cys Cys
1               5                   10                  15

<210> SEQ ID NO 45
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 45

Asp Cys His Cys Lys Ala Asn His Gln Glu Gly Pro Thr Val Asp Cys
1               5                   10                  15

Cys Lys

<210> SEQ ID NO 46
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 46

His Lys Lys Ala Asn His Gln Glu Gly Thr Val Glu
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 47
```

```
His Glu Arg Ala Asn His Gln Gln Gly Pro Thr Val Lys
1               5                   10
```

<210> SEQ ID NO 48
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 48

```
His Glu Pro Arg Ala Asn His Gln Glu
1               5
```

<210> SEQ ID NO 49
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 49

```
Lys His Pro Arg Ala Asn His Gln Lys
1               5
```

<210> SEQ ID NO 50
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 8, 16
<223> OTHER INFORMATION: Xaa = an amino acid analogue that forces a beta
      turn

<400> SEQUENCE: 50

```
His Pro Lys Ala Asn His Gln Xaa His Pro Lys Ala Asn His Gln Xaa
1               5                   10                  15
```

<210> SEQ ID NO 51
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 8, 16
<223> OTHER INFORMATION: Xaa = an amino acid analogue that forces a beta
      turn

<400> SEQUENCE: 51

```
His Met Lys Ala Asn His Gln Xaa His Met Lys Ala Asn His Gln Xaa
1               5                   10                  15
```

<210> SEQ ID NO 52
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 5, 10
<223> OTHER INFORMATION: Xaa = an amino acid analogue that forces a beta
      turn

```
<400> SEQUENCE: 52

Pro Asn His Gln Xaa Pro Asn His Gln Xaa
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 5, 10
<223> OTHER INFORMATION: Xaa = an amino acid analogue that forces a beta
      turn

<400> SEQUENCE: 53

Ala Asn His Gln Xaa Ala Asn His Gln Xaa
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 54

His Cys Lys Ala Asn His Gln
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 55

Gly Pro Thr Val Gly
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 56

Gly Pro Thr Ile Thr Gly
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 57

Gly Pro Glu Thr Asp
1               5

<210> SEQ ID NO 58
<211> LENGTH: 5
<212> TYPE: PRT
```

```
<213> ORGANISM: Artificial Sequence
<220> FEATURE:
<223> OTHER INFORMATION: Synthetically generated peptide

<400> SEQUENCE: 58

Gly Pro Thr Gly Glu
 1               5

<210> SEQ ID NO 59
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 59

Gly Thr Val Thr Gly Gly
 1               5

<210> SEQ ID NO 60
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 60

Asp Gly Pro Thr Thr Ser
 1               5

<210> SEQ ID NO 61
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 61

Gly Pro Asp Phe Gly Ser
 1               5

<210> SEQ ID NO 62
<211> LENGTH: 58
<212> TYPE: PRT
<213> ORGANISM: Homo sapiens

<400> SEQUENCE: 62

Met His Ser Phe Cys Ala Phe Lys Ala Asp Asp Gly Pro Cys Lys Ala
 1               5                  10                  15

Ile Met Lys Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55
```